(12) United States Patent
Fischer et al.

(10) Patent No.: US 11,981,737 B2
(45) Date of Patent: May 14, 2024

(54) ANTI-HLA-G ANTIBODIES AND USE THEREOF

(71) Applicant: Hoffmann-La Roche Inc., Little Falls, NJ (US)

(72) Inventors: Jens Fischer, Penzberg (DE); Meher Majety, Penzberg (DE); Stefan Dengl, Penzberg (DE); Georg Tiefenthaler, Penzberg (DE); Stefan Klostermann, Penzberg (DE); Claudia Kirstenpfad, Penzberg (DE); Esther Koenigsberger, Penzberg (DE); Francesca Ros, Penzberg (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 331 days.

(21) Appl. No.: 16/415,979

(22) Filed: May 17, 2019

(65) Prior Publication Data

US 2020/0102389 A1  Apr. 2, 2020

Related U.S. Application Data

(63) Continuation of application No. PCT/EP2017/079429, filed on Nov. 16, 2017.

(30) Foreign Application Priority Data

Nov. 18, 2016  (EP) .................... 16199620

(51) Int. Cl.
*C07K 16/00* (2006.01)
*C07K 16/28* (2006.01)
*G01N 33/574* (2006.01)

(52) U.S. Cl.
CPC ... *C07K 16/2833* (2013.01); *G01N 33/57484* (2013.01); *C07K 2317/33* (2013.01); *C07K 2317/622* (2013.01); *C07K 2317/76* (2013.01); *G01N 2333/70539* (2013.01)

(58) Field of Classification Search
CPC ............ C07K 16/2833; C07K 2317/33; C07K 2317/622; C07K 2317/76; G01N 33/57484; G01N 2333/70539; A61P 35/00
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,208,020 A | 5/1993 | Chari et al. |
| 5,416,064 A | 5/1995 | Chari et al. |
| 5,500,362 A | 3/1996 | Robinson et al. |
| 5,591,828 A | 1/1997 | Bosslet et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,877,296 A | 3/1999 | Hamann et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,630,579 B2 | 10/2003 | Chari et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,189,826 B2 | 3/2007 | Rodman |
| 7,332,581 B2 | 2/2008 | Presta |
| 7,371,826 B2 | 5/2008 | Presta |
| 7,498,298 B2 | 3/2009 | Doronina et al. |

(Continued)

FOREIGN PATENT DOCUMENTS

| CN | 1308675 A | 8/2001 |
|---|---|---|
| CN | 1718588 A | 1/2006 |

(Continued)

OTHER PUBLICATIONS

Riteau etal (Intern Immunology 13: 193-201, 2001) (Year: 2001).*
Gonen-Gross (J. Immunol 175:4866-4874, 2005). (Year: 2005).*
Fournel et al (Tissue Antigens 55:510-518, 2000 (Year: 2000).*
Menier et al (Human Immunolgoy 64:315-26, 2003, IDS filed on Mar. 6, 2020, #7 (Year: 2003).*
Bensussan, A. et al., "Detection of membrane-bound HLA-G translated products with a specific monoclonal antibody" PNAS USA 92(22):10292-10296 (Oct. 24, 1995).
Ding, X-S, et al., "OPL077: Experimental Study of Human Umbilical Cord Blood Cells Transplantation for Treatment of Cerebral Isehemia in rats" J Neurol Sci 238:S65 (Nov. 8, 2005).

(Continued)

*Primary Examiner* — Lei Yao
(74) *Attorney, Agent, or Firm* — Clark & Elbing LLP; Karen L. Elbing

(57) ABSTRACT

The present invention relates to anti-HLA-G antibodies and methods of using the same.

9 Claims, 15 Drawing Sheets

Specification includes a Sequence Listing.

(56) References Cited

U.S. PATENT DOCUMENTS

| | | |
|---|---|---|
| 7,521,541 B2 | 4/2009 | Eigenbrot et al. |
| 7,527,791 B2 | 5/2009 | Adams et al. |
| 7,695,936 B2 | 4/2010 | Carter et al. |
| 2003/0232051 A1 | 12/2003 | Long et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0163770 A1 | 7/2005 | Reiter |
| 2005/0260186 A1 | 11/2005 | Bookbinder et al. |
| 2005/0266000 A1 | 12/2005 | Bond et al. |
| 2006/0025576 A1 | 2/2006 | Miller et al. |
| 2006/0104968 A1 | 5/2006 | Bookbinder et al. |
| 2007/0020703 A1 | 1/2007 | Menier et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0259403 A1 | 11/2007 | Miyagawa et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2011/0142864 A1 | 6/2011 | Dengjel |
| 2014/0051834 A1* | 2/2014 | Hoffman .......... A61P 3/10 530/387.3 |
| 2020/0102389 A1 | 4/2020 | Fischer et al. |
| 2021/0147553 A1 | 5/2021 | Dengl et al. |
| 2021/0147554 A1 | 5/2021 | Dengl et al. |
| 2022/0213199 A1 | 7/2022 | Bujotzek et al. |

FOREIGN PATENT DOCUMENTS

| | | |
|---|---|---|
| CN | 101967191 A | 2/2011 |
| CN | 104203982 A | 12/2014 |
| CN | 106795221 A | 5/2017 |
| EP | 0404097 B1 | 9/1996 |
| EP | 0425235 B1 | 9/1996 |
| EP | 2264067 A1 | 12/2010 |
| EP | 1870459 B1 | 6/2016 |
| JP | 2020-511112 A | 4/2020 |
| RU | 2635537 C2 | 11/2017 |
| WO | WO-93/01161 A1 | 1/1993 |
| WO | WO-93/08829 A1 | 5/1993 |
| WO | WO-93/16185 A2 | 8/1993 |
| WO | WO-93/16185 A3 | 9/1993 |
| WO | WO-94/11026 A2 | 5/1994 |
| WO | WO-94/11026 A3 | 8/1994 |
| WO | WO-94/29351 A2 | 12/1994 |
| WO | WO-94/29351 A3 | 2/1995 |
| WO | WO-96/27011 A1 | 9/1996 |
| WO | WO-98/50431 A2 | 11/1998 |
| WO | WO-98/50431 A3 | 1/1999 |
| WO | WO-99/42128 A1 | 8/1999 |
| WO | WO-00/03016 A1 | 1/2000 |
| WO | WO-01/77342 A1 | 10/2001 |
| WO | WO-02/22784 A2 | 3/2002 |
| WO | WO-2004/056312 A2 | 7/2004 |
| WO | WO-2004/106381 A1 | 12/2004 |
| WO | WO-2005/061547 A2 | 7/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/044908 A2 | 4/2006 |
| WO | WO-2007/042261 A2 | 4/2007 |
| WO | WO-2007/110205 A2 | 10/2007 |
| WO | WO-2007/147901 A1 | 12/2007 |
| WO | WO-2008/024715 A2 | 2/2008 |
| WO | WO-2008/119567 A2 | 10/2008 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/112193 A1 | 10/2010 |
| WO | WO-2010/115589 A1 | 10/2010 |
| WO | WO-2010/115589 A8 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145792 A8 | 12/2010 |
| WO | WO-2010/145793 A1 | 12/2010 |
| WO | WO-2010/150233 A2 | 12/2010 |
| WO | WO-2010/150235 A1 | 12/2010 |
| WO | WO-2010/129304 A3 | 2/2011 |
| WO | WO-2011/034605 A2 | 3/2011 |
| WO | WO-2011/090754 A1 | 7/2011 |
| WO | WO-2011/090762 A1 | 7/2011 |
| WO | WO-2011/117330 A1 | 9/2011 |
| WO | WO-2011/143545 A1 | 11/2011 |
| WO | WO-2012020006 A2 | 2/2012 |
| WO | WO-2012/025525 A1 | 3/2012 |
| WO | WO-2012/025530 A1 | 3/2012 |
| WO | WO-2012/041968 A1 | 4/2012 |
| WO | WO-2012/058768 A1 | 5/2012 |
| WO | WO-2012/058768 A8 | 6/2012 |
| WO | WO-2013/026831 A1 | 2/2013 |
| WO | WO-2013/026833 A1 | 2/2013 |
| WO | WO-2013/026835 A1 | 2/2013 |
| WO | WO-2013/026839 A1 | 2/2013 |
| WO | WO-2013/059885 A2 | 5/2013 |
| WO | WO-2013/096291 A2 | 6/2013 |
| WO | WO-2013/096291 A3 | 6/2013 |
| WO | WO-2013/106586 A2 | 7/2013 |
| WO | WO-2013/120929 A1 | 8/2013 |
| WO | WO-2013/157953 A1 | 10/2013 |
| WO | WO-2013/157954 A1 | 10/2013 |
| WO | WO-2013/164325 A1 | 11/2013 |
| WO | WO-2013/174873 A1 | 11/2013 |
| WO | WO2014072534 * | 5/2014 |
| WO | WO-2015066379 A2 | 5/2015 |
| WO | WO-2015/095539 A1 | 6/2015 |
| WO | WO-2015/150447 A1 | 10/2015 |
| WO | WO-2016/016299 A1 | 2/2016 |
| WO | WO-2016/020309 A1 | 2/2016 |
| WO | WO-2016/062734 A1 | 4/2016 |
| WO | WO-2016/094566 A2 | 6/2016 |
| WO | WO-2016/160622 A2 | 10/2016 |
| WO | WO-2016/172485 A2 | 10/2016 |
| WO | WO-2017060144 A1 | 4/2017 |
| WO | WO-2017/207775 A1 | 12/2017 |
| WO | WO-2019/202040 A1 | 10/2019 |
| WO | WO-2019/202041 A1 | 10/2019 |
| WO | WO-2020/043899 A1 | 3/2020 |

OTHER PUBLICATIONS

Fagerstam, L., et al., "Detection of Antigen-Antibody Interactions by Surface Plasmon Resonance" J Mol Recognit 3(5-6):208-214 (Oct. 1, 1990).

"International Preliminary Report on Patentability—PCT/EP2017/079429" :pp. 1-9 (May 31, 2019).

"International Search Report—PCT/EP2017/079429" :pp. 1-8 (Mar. 20, 2018).

Lin, A., et al., "Human Leukocyte Antigen-G (HLA-G) Expression in Cancers: Roles in Immune Evasion, Metastasis and Target for Therapy" Mol Med 21(1):782-791 (Jan. 1, 2015).

Menier, C., et al., "Characterization of Monoclonal Antibodies Recognizing HLA-G or HLA-E: New Tools to Analyze the Expression of Nonclassical HLA Class I Molecules" Hum Immunol 64(3):315-326 (Mar. 1, 2003).

Menier, C., et al., "MICA Triggering Signal for NK Cell Tumor Lysis is counteracted by HLA-G1-mediated Inhibitory Signal" Int J Cancer 100(1):63-70 (Jul. 1, 2002).

Riteau, B., et al., "HLA-G1 co-expression boosts the HLA class I-mediated NK lysis inhibition" Int Immunol 13(2):193-201 (Feb 1, 2001)

Allan et al., "Tetrameric complexes of HLA-E, HLA-F, and HLA-G," J Immunol Methods. 268(1):43-50 (2002).

Almagro et al., "Humanization of antibodies," Front Biosci. 13:1619-33 (2008).

(56) References Cited

OTHER PUBLICATIONS

Amiot et al., "Biology of HLA-G in cancer: a candidate molecule for therapeutic intervention?," Cell Mol LifeSci. 68(3):417-31 (2011).
Amiot et al., "Immunomodulatory Properties of HLA-G in Infectious Diseases," J Immunol Res. 2014:298569 (2014) (15 pages).
Amodio et al., "New insights into HLA-G mediated tolerance," Tissue Antigens. 84(3):255-63 (2014).
Apps et al., "HLA-G is present on the surface of normal extravillous trophoblast as homodimers with high avidity for the LILR receptors of decidual leukocytes," 4th International Conference on HLA-G, Jul. 10-12, Paris, France. Tissue Antigens. 68(4):359 Abstract 00020 (2006) (1 page).
Atwell et al., "Stable Heterodimers from Remodeling the Domain Interface of a Homodimer using a Phage Display Library," J Mol Biol. 270(1):26-35 (1997).
Baca et al., "Antibody Humanization Using Monovalent Phage Display," J Biol Chem. 272(16):10678-84 (1997).
Bacac et al., "CEA TCB: A novel head-to-tail 2:1 T cell bispecific antibody for treatment of CEA-positive solid tumors," Oncoimmunology. 5(8):e1203498 (2016) (3 pages).
Boerner et al., "Production of antigen-specific human monoclonal antibodies from in vitro-primed human splenocytes," J Immunol. 147(1):86-95 (1991).
Borges et al., "Interactions of LIRs, a Family of Immunoreceptors Expressed in Myeloid and Lymphoid Cells, with Viral and Cellular MHC Class I Antigens." *Immunoreceptor Tyrosine-based Inhibition Motifs*. Marc Daëron and Eric Vivier, 123-136 (1999).
Boyson et al., "Disulfide bond-mediated dimerization of HLA-G on the cell surface," Proc Natl Acad Sci U S A. 99(25):16180-5 (2002).
Brennan et al., "Preparation of Bispecific Antibodies by Chemical Recombination of Monoclonal Immunoglobulin $G_1$ Fragments," Science. 229(4708):81-3 (1985).
Brodeur et al., "Mouse-Human Myeloma Partners for the Production of Heterohybridomas," Monoclonal Antibody Production Techniques and Applications. New York:51-63 (1987).
Brüggemann et al., "Comparison of the Effector Functions of Human Immunoglobulins Using a Matched set of Chimeric Antibodies," J Exp Med. 166(5):1351-61 (1987).
Cantoni et al., "p49, a putative HLA class I-specific inhibitory NK receptor belonging to the immunoglobulin superfamily," Eur J Immunol. 28(6):1980-90 (1998).
Carter, "Bispecific human IgG by design," J Immunol Methods. 248(1-2):7-15 (2001).
Carter et al., "Humanization of an anti-p185$^{HER2}$ antibody for human cancer therapy," Proc Natl Acad Sci U S A. 89(10):4285-9 (1992).
Chang et al., "Tolerization of dendritic cells by $T_s$ cells: the crucial role of inhibitory receptors ILT3 and ILT4," Nat Immunol. 3(3):237-43 (2002).
Chari et al., "Immunoconjugates Containing Novel Maytansinoids: Promising Anticancer Drugs," Cancer Res. 52(1):127-31 (1992).
Charlton, "Expression and Isolation of Recombinant Antibody Fragments in *E. coli.*" *Methods in Molecular Biology, vol. 248: Antibody Engineering: Methods and Protocols.* B. K. C. Lo, 245-54 (2004).
Chen et al., "Selection and Analysis of an Optimized Anti-VEGF Antibody: Crystal Structure of an Affinity-matured Fab in Complex with Antigen," J Mol Biol. 293(4):865-81 (1999).
Chowdhury, "Engineering Hot Spots for Affinity Enhancements of Antibodies," *Methods in Molecular Biology, vol. 207: Recombinant Antibodies for Cancer Therapy: Methods and Protocols.* M. Welschof and J. Krauss, 179-96 (2003).
Clackson et al., "Making antibody fragments using phage display libraries," Nature. 352(6336):624-8(1991).
Clements et al., "Crystal structure of HLA-G: A nonclassical MHC class I molecule expressed at the fetal-maternal interface," Proc Natl Acad Sci U S A. 102(9):3360-5 (2005).
Clynes et al., "Fc receptors are required in passive and active immunity to melanoma," Proc Natl Acad Sci U S A. 95(2):652-6 (1998).
Colonna et al., "A novel family of Ig-like receptors for HLA class I molecules that modulate function of lymphoid and myeloid cells," J Leukoc Biol. 66(3):375-81 (1999).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
Cunningham et al., "High-Resolution Epitope Mapping of hGH-Receptor Interactions by Alanine-Scanning Mutagenesis," Science. 244(2908):1081-85 (1989).
Dall'Acqua et al., "Antibody humanization by framework shuffling," Methods. 36(1):43-60 (2005).
Dubowchik et al., "Doxorubicin Immunoconjugates Containing Bivalent Lysosomally-Cleavable Dipeptide Linkages," Bioorg Med Chem Lett. 12(11):1529-32 (2002).
Duncan et al., "The binding site for C1q on IgG," Nature. 332(6166):738-40 (1988).
Fellouse et al., "Synthetic anitbodies from a four-amino-acid code: A dominant role for tyrosine in antigen recognition," Proc Natl Acad Sci U S A. 101(34):12467-72 (2004).
Gazzano-Santoro et al., "A non-radioactive complement-dependent cytotoxicity assay for anti-CD20 monoclonal antibody," J Immunol Methods. 202(2):163-171 (1997).
Gerngross, "Advances in the production of human therapeutic proteins in yeasts and filamentous fungi,"Nat Biotechnol. 22(11):1409-1414 (2004).
Gonen-Gross et al., "Complexes of HLA-G Protein on the Cell Surface Are Important for Leukocyte Ig-Like Receptor-1 Function," J Immunol. 171(3):1343-1351 (2003).
Graham et al., "Characteristics of a Human Cell Line Transformed by DNA from Human Adenovirus Type 5," J Gen Virol. 36(1):59-74 (1977).
Griffiths et al., "Human anti-self antibodies with high specificity from phage display libraries," EMBO J. 12(2):725-34 (1993).
Gruber et al., "Efficient Tumor Cell Lysis Mediated by a Bispecific Single Chain Antibody Expressed in *Escherichia coli*" J Immunol. 152(11):5368-5374 (1994).
Guyer et al., "Immunoglobulin Binding by Mouse Intestinal Epithelial Cell Receptors," J Immunol. 117(2):587-593(1976).
Hara et al., "Altered Expression of Human Leukocyte Antigen G (HLA-G) on Extravillous Trophoblasts in Preeclampsia: Immunohistological Demonstration With Anti-HLA-G Specific Antibody '87G' and Anti-cytokeratin Antibody 'CAM5.2'," Am J Reprod Immunol. 36(8):349-358 (1996).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-1502 (1985).
Hinman et al., "Preparation and Characterization of Monoclonal Antibody Conjugates of the Calicheamicins: A Novel and Potent Family of Antitumor Antibodies," Cancer Res. 53(14):3336-42 (1993).
Holliger et al., "Diabodies: Small bivalent and bispecific antibody fragments," Proc Natl Acad Sci U S A. 90(14):6444-48(1993).
Holliger et al., "Specific killing of lymphoma cells by cytotoxic T-cells mediated by a bispecific diabody," Protein Eng. 9(3):299-305 (1996).
Hoogenboom et al., "By-passing Immunisation. Human Antibodies from Synthetic Repertoires of Gemline $V_H$ Gene Segments Rearranged in Vitro" J Mol Biol. 227(2):381-88 (1992).
Hoogenboom et al., "Overview of Antibody Phage-Display Technology and Its Applications," Methods Mol Biol. 178:1-37 (2002).
Hudson et al., "Engineered antibodies," Nat Med. 9(1):129-134 (2003).
Hunt et al., "HLA-G and immune tolerance in pregnancy," FASEB J. 19(7):681-693 (2005).
Jeffrey et al., "Dipeptide-based highly potent doxorubicin antibody conjugates," Bioorg Med Chem Lett. 16(2):358-362 (2006).

(56) References Cited

OTHER PUBLICATIONS

Johnson et al., "Effector Cell Recruitment wiht Novel Fv-based Dual-affinity Re-targeting Protein Leads to Potent Tumor Cytolysis and in Vivo B-cell Depletion," J Mol Biol. 399(3):436-449 (2010).
Ju et al., "Immunoglobulin-like transcripts ILT2, ILT3 and ILT7 are expressed by human dendritic cells and down-regulated following activation," Gene. 331:159-164 (2004).
Kam et al., "Carbon nanotubes as multifunctional biological transporters and near-infrared agents for selective cancer cell destruction," Proc Natl Acad Sci U S A. 102(33):11600-605 (2005).
Kashmiri et al., "SDR grafting—a new approach to antibody humanization," Methods. 36(1):25-34 (2005).
Kim et al., "Localization of the site of the murine IgG1 molecule that is involved in binding to the murine intestinal Fc receptor," Eur J Immunol. 24(10):2429-2434 (1994).
King et al., "Monoclonal Antibody Conjugates of Doxorubicin Prepared with Branched Peptide Linkers: Inhibition of Aggregation by Methoxytriethyleneglycol Chains," J Med Chem. 45(19):4336-43 (2002).
Kipriyanov et al., "Bispecific Tandem Diabody for Tumor Therapy with Improved Antigen Binding and Pharmacokinetics," J Mol Biol. 293(1):41-56 (1999).
Klein et al., "The use of CrossMAb technology for the generation of bi- and multispecific anitbodies," MAbs. 8(6):1010-20 (2016).
Klimka et al., "Human anti-CD30 recombinant antibodies by guided phage antibody selection using cell panning," Br J Cancer. 83(2):252-260 (2000).
Kostelny et al., "Formation of a bispecific antibody by the use of leucine zippers," J Immunol. 148(5):1547-1553 (1992).
Kozbor et al., "A Human Hybrid Myeloma for Production of Human Monoclonal Antibodies," J Immunol. 133(6):3001-5 (1984).
Kratz et al., "Prodrugs of Anthracyclines in Cancer Chemotherapy," Curr Med Chem. 13(5):477-523 (2006).
Kuroki et al., "Immune modulation of HLA-G dimer in maternal-fetal interface," Eur J Immunol. 37(7):1727-29 (2007).
Lee et al., "Bivalent antibody phage display mimics natural immunoglobulin," J Immunol Methods. 284(1-2):119-32 (2004).
Lee et al., "High-affinity Human Antibodies from Phage-displayed Synthetic Fab Libraries with a Single Framework Scaffold," J Mol Biol. 340(5):1073-93 (2004).
Li et al., "Human antibodies for immunotherapy development generation via a human B cell hybridoma technology," Proc Natl Acad Sci U S A. 103(10):3557-62 (2006).
Li et al., "Optimization of humanized IgGs in glycoengineered *Pichia pastoris*," Nat Biotechnol. 24(2):210-5 (2006).
Lo et al., "Effector-attenuating Substitutions That Maintain Anitbody Stability and Reduce Toxicity in Mice," J Biol Chem. 292(9):3900-3908 (2017) (10 pages).
Lode et al., "Targeted Therapy with a Novel Enediyene Antibiotic Calicheamicin(I)1 *Effectively Suppresses Growth and Dissemination of Liver Metastases in a Syngeneic Model of Murine Neuroblastoma*," Cancer Res. 58(14):2925-28 (1998).
Lonberg, "Fully human antibodies from transgenic mouse and phage display platforms," Curr Opin Immunol. 20(4):450-459 (2008).
Lonberg, "Human antibodies from transgenic animals," Nat Biotechnol. 23(9):1117-25 (2005).
Lum et al., "Targeting T Cells with Bispecific Antibodies for Cancer Therapy," available in PMC Dec. 1, 2011, published in final edited form as: Biodrugs. 25(6):365-379 (2011).
Maric et al., "Defective Antigen Processing in GILT-Free Mice," Science. 294(5545):1361-5 (2001).
Marks et al., "By-passing Immunization Human Antibodies from V-gene Libraries Displayed on Phage," J Mol Biol. 222(3):581-97 (1991).
Marks et al., "Selection of human antibodies from phage display libraries," Antibody Engineering. Methods Mol Biol. 248:161-176 (2004).
Mather et al., "Culture of Testicular Cells in Hormone-Supplemented Serum-Free Medium," Ann NY Acad Sci. 383:44-68 (1982).
Mather, "Establishment and Characterization of Two Distinct Mouse Testicular Epithelial Cell Lines," Biol Reprod. 23(1):243-252 (1980).
McCafferty et al., "Phage antibodies: filamentous phage displaying antibody variable domains," Nature. 348(6301):552-4 (1990).
Meissner et al., "Transient Gene Expression: Recombinant Protein Production with Suspension-Adapted HEK293-EBNA Cells," Biotechnol Bioeng. 75(2):197-203 (2001).
Milstein et al., "Hybrid hybridomas and their use in immunohistochemistry," Nature. 305(5934):537-40(1983).
Morrison et al., "Chimeric human antibody molecules: Mouse antigen-binding domains with human constant region domains," Proc Natl Acad Sci U S A. 81(21):6851-5 (1984).
Nagorsen et al., "Immunomodulatory therapy of cancer with T cell-engaging BiTE antibody blinatumomab," Exp Cell Res. 317(9):1255-60 (2011).
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc Natl Acad Sci U S A. 97(2):829-34 (2000).
Nakajima et al., "Transcriptional Regulation of ILT Family Receptors," J Immunol. 171(12):6611-20 (2003).
Ni, "Research progress and future perspectives in antibodomics and antibodomic drugs," HCAPLUS Accession No. 2006:1101736. Xiandai Mianyixue. 26(4):265-268 (2006) (Abstract Only) (3 pages).
Osbourn et al., "From rodent reagents to human therapeutics using antibody guided selection," Methods. 36(1):61-8 (2005).
Padlan, "A possible procedure for reducing the immunogenicity of antibody variable domains while preserving their ligand-binding properties," Mol Immunol. 28(4-5):489-98 (1991).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Plückthun, "Chapter 11: Antibodies from *Escherichia coli*" *The Pharmacology of Monoclonal Antibodies*. Martin Rosenberg and Gordon P. Moore, 269-315 (1994) (26 pages).
Polakova et al., "Binding analysis of HLA-G specific antibodies to hematopoietic cells isolated from leukemia patients," Neoplasma. 50(5):331-8 (2003).
Ponte et al., "Inhibitory receptors sensing HLA-G1 molecules in pregnancy: Decidua-associated natural killer cells express LIR-1 and CD94/NKG2A and acquire p49, an HLA-G1-specific receptor," Proc Natl Acad Sci U S A. 96(10):5674-9 (1999).
Presta et al., "Humanization of an Antibody Directed Against IgE," J Immunol. 151(5):2623-32 (1993).
Queen et al., "A humanized antibody that binds to the interleukin 2 receptor," Proc Natl Acad Sci U S A. 86(24):10029-33 (1989).
Rajagopalan et al., "A Human Histocompatibility Leukocyte Antigen (HLA)-G-specific Receptor Expressed on All Natural Killer Cells," J Exp Med. 189(7):1093-99 (1999).
Ridgway et al., "'Knobs-into-holes' engineering of antibody $C_H3$ domains for heavy chain heterodimerization," Protein Eng. 9(7):617-21 (1996).
Riechmann et al., "Reshaping human antibodies for therapy," Nature. 322(6162):323-7 (1988).
Ristich et al., "Tolerization of dendritic cells by HLA-G," Eur J Immunol. 35(4):1133-42 (2005).
Roosnek et al., "T cell activation by a bispecific anti-CD3/anti-major histocompatibility complex class I antibody," Eur J Immunol. 20(6):1393-6 (1990).
Rosok et al., "A Combinatorial Library Strategy for the Rapid Humanization of Anticarcinoma BR96 Fab," J Biol Chem. 271(37):22611-8 (1996).
Ruan et al., "Recent progress of HLA-G in cancer," Chinese Bulletin of Life Sciences. 24(3):242-49 (2012) (English language abstract).
Rudolph et al., "Crystal Structures of Two Rat MHC Class Ia (RT1-A) Molecules that are Associated Differentially with Peptide Transporter Alleles TAP-A and TAP-B" J Mol Biol. 324(5):975-90 (2002).
Sanders et al., "Cell-Cell Adhesion Mediated by CD8 and Human Histocompatibility Leukocyte Antigen G, a Nonclassical Major

(56) References Cited

OTHER PUBLICATIONS

Histocompatibility Complex Class 1 Molecule on Cytotrophoblasts," J Exp Med. 174(3):737-40 (1991).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Selvakumar et al., "NK cell receptor gene of the KIR family with two IG domains but highest homology to KIR receptors with three IG domains," Tissue Antigens. 48(4 Pt 1):285-94 (1996).
Sheu et al., "HLA-G and Immune Evasion in Cancer Cells," J Formos Med Assoc. 109(4):248-57 (2010).
Shields et al., "High Resolution Mapping of the Binding Site on Human IgG1 for FcγRI, FcγRII, FcγRIII, and FcRn and Design of IgG1 Variants with Improved Binding to the FcγR," J Biol Chem. 276(9):6591-604 (2001).
Shiroishi et al., "Efficient Leukocyte Ig-like Receptor Signaling and Crystal Structure of Disulfide-linked HLA-G Dimer," The Journal of Biological Chemistry. 281(15):10439-47 (2006) (10 pages).
Shiroishi et al., "Human inhibitory receptors Ig-like transcript 2 (ILT2) and ILT4 compete with CD8 for MHC class I binding and bind preferentially to HLA-G," Proc Natl Acad Sci U S A. 100(15):8856-61 (2003).
Shore et al., "Chain B, YTS 105.18 Antigen Binding Region Heavy Chain," GenBank, accession No. 2ARJ_B (2020) (3 pages).
Sidhu et al., "Phage-displayed Antibody Libraries of Synthetic Heavy Chain Complementarity Determining Regions," J Mol Biol. 338(2):299-310 (2004).
Sims et al., "A Humanized CD18 Antibody Can Block Function without Cell Destruction," J Immunol. 151(4):2296-308 (1993).
Spiess et al., "Alternative molecular formats and therapeutic applications for bispecific antibodies," Mol Immunol. 67(2 Pt A):95-106 (2015).
Spurny et al., "T cell infiltration into EwiNg sarcomas is associated with local expression of immune-inhibitory HLA-G," Oncotarget. 9(5):6536-49 (2018).
Stoel et al., "Immunoglobulin heavy chain variable region partial [Rattus norvegicus]," GenBank, accession No. CAL25600 (2016) (2 pages).
Suciu-Foca et al., "Molecular characterization of allospecific T suppressor and tolerogenic dendritic cells: review," Int Immunopharmacol. 5(1):7-11 (2005).
Torgov et al., "Generation of an Intensely Potent Anthracycline by a Monoclonal Anitbody-β-Galactosidase Conjugate," Bioconjug Chem. 16(3):717-21 (2005).
Traunecker et al., "Bispecific single chain molecules (Janusins) target cytotoxic lymphocytes on HIV infected cells," EMBO J. 10(12):3655-9 (1991).
Tutt et al., "Trispecific F(ab')₃ derivatives that use cooperative signaling via the TCR/CD3 complex and CD2 to activate and redirect resting cytotoxic T cells," J Immunol. 147(1):60-69 (1991).
Urlaub et al., "Isolation of Chinese hamster cell mutants deficient in dihydrofolate reductase activity," Proc Natl Acad Sci U S A. 77(7):4216-20 (1980).
Valiante et al., "Functionally and Structurally Distinct NK Cell Receptor Repertoires in the Peripheral Blood of Two Human Donors," Immunity. 7(6):739-51 (1997).
Valliere-Douglass et al., "Glutamine-linked and Non-consensus Asparagine-linked Oligosaccharides Present in Human Recombinant Antibodies Define Novel Protein Glycosylation Motifs," J Biol Chem. 285(21):16012-22 (2010).
Van de Bovenkamp et al., "Adaptive antibody diversification through N-linked glycosylation of the immunoglobulin variable region," Proc Natl Acad Sci U S A. 115(8):1901-1906 (2018).
Van Dijk et al., "Human antibodies as next generation therapeutics," Curr Opin Chem Biol. 5(4):368-74 (2001).
Vitetta et al., "Redesigning Nature's Poisons to Create Anit-Tumor Reagents," Science. 238(4830):1098-104 (1987).

Vollmers et al., "Death by Stress: Natural IgM-lnduced Apoptosis," Methods Find Exp Clin Pharmacol. 27(3):185-91 (2005).
Vollmers et al., "The 'early birds': natural IgM antibodies and immune surveillance," Histol and Histopathol. 20(3):927-37 (2005).
Wan et al., "Human Leukocyte Antigen-G Inhibits the Anti-Tumor Effect of Natural Killer Cells via Immunoglobulin-Like Transcript 2 in Gastric Cancer," Cell Physiol and Biochem. 44(5):1828-41 (2017).
Wiendl et al., "The non-classical MHC molecule HLA-G protects human muscle cells from immune-mediated lysis: implications for myoblast transplantation and gene therapy," Brain. 126(Pt. 1):176-85 (2003).
Winter et al., "Making Antibodies by Phage Display Technology," Annu Rev Immunol. 12:433-55 (1994).
Wu et al., "Rescuing lymphocytes from HLA-G immunosuppressive effects mediated by the tumor microenvironment," Oncotarget. 6(35):37385-97 (2015).
Yazaki et al., "Expression of Recombinant Antibodies in Mammalian Cell Lines." *Methods in Molecular Biology, vol. 248: Antibody Engineering: Methods and Procedures*. B. K. C. Lo, 255-68 (2004).
Extended European Search Report for European Patent Application No. 20214951.4, dated Jul. 20, 2021 (13 pages).
International Preliminary Report on Patentability for International Application No. PCT/EP2019/060007, dated Oct. 29, 2020 (11 pages).
International Preliminary Report on Patentability for International Application No. PCT/EP2019/060008, dated Oct. 20, 2020 (7 pages).
International Search Report and Written Opinion for International Application No. PCT/EP2019/060007, dated Jul. 17, 2019 (19 pages).
International Search Report and Written Opinion for International Application No. PCT/EP2019/060008, dated May 27, 2019 (12 pages).
International Search Report and Written Opinion for International Patent Application No. PCT/EP2021/085810, dated Apr. 7, 2022 (20 pages).
Kuznetzova, E. A., "Brackets in text of legal document as a linguistic and cognitive phenomenon," Vestnik MGOU. Series: Russian Philology. 3:37-42 (2015) (12 pages).
Roitt et al., "Different antigen antibody binding is ensured by hypervariable sequences of antigen-recognizing centers," Moscow, Mir: Immunology. 110-1 (2000) (5 pages).
Singer et al., "Genes and Genomes," Moskow "MIR". 1:63-64 (1998) (7 pages).
Lu et al., "Preparation of anti-HLA-G monoclonal antibody G11E5," Chin J Cell Mol Immunol. 22(2) (2006) (3 pages).
Zeng et al., "Effect of overexpression of human leukocyte antigen-G in hepatocellular carcinoma Hep3B cells on killing activity of NK cells in vitro," Chinese Journal of Pathophysiology 28(4):613-618 (2012) (6 pages).
"Annex 4-15E7 Specificity and Blocking Activity," experimental annex cited in opposition to patent EP2917229B1 on Oct. 6, 2020, by Regimbeau (5 pages).
"Immunologists' Toolbox: Immunization." Excerpt from Janeway's Immunobiology, eds. Murphy et al., 7th ed., p. 735 (2008) (3 pages).
Abcam Product Datasheet for "Anti-HLA G antibody [MEM-G/1] ab7759" cited in opposition to patent EP2917229B1 on Oct. 7, 2020 (3 pages).
Agaugue et al., "Role of HLA-G in tumor escape through expansion of myeloid-derived suppressor cells and cytokinic balance in favor of Th2 versus Th1/Th17," Blood. 117(26):7021-31 (Jun. 30, 2011).
Angal et al., "A single amino acid substitution abolishes the heterogeneity of chimeric mouse/human (IgG4) antibody," Mol Immunol. 30(1): 105-8(1993).
Apps et al., "A critical look at HLA-G," Trends Immunol. 29(7):313-21 (2008).
Arns et al., "Structural Modeling and Molecular Dynamics of the Immune Checkpoint Molecule HLA-G," Front. Immunol. 11:575076. doi: 10.3389/fimmu.2020.575076 (Nov. 2020).
Barnstable et al., "Production of monoclonal antibodies to group A erythrocytes, HLA and other human cell surface antigens-new tools for genetic analysis," Cell 14(1) Abstract (1978).

(56) References Cited

OTHER PUBLICATIONS

Barnstable et al., "Production of Monoclonal Antibodies to Group A Erythrocytes, HLA and Other Human Cell Surface Antigens-New Tools for Genetic Analysis," Cell. 14(1):9-20 (1978).
Beers et al., "Type II (tositumomab) anti-CD20 monoclonal antibody out performs type I (rituximab-like) reagents in B-cell depletion regardless of complement activation," Blood 112(10):4170-4177 (2008).
Blaschitz et al., "The soluble pool of HLA-G produced by human trophoblasts does not include detectable levels of the intron 4-containing HLA-G5 and HLA-G6 isoforms," Molecular Human Reproduction 11(10):699-710 (2005).
Carosella et al., "Beyond the increasing complexity of the immunomodulatory HLA-G molecule," Blood. 111(10):4862-70 (May 15, 2008).
Carosella et al., "HLA-G: from biology to clinical benefits," Trends in Immunology. 29(3): 125-32 (2008).
Chaplin, David D., "Overview of the immune response," J Allergy Clin Immunol. 125(2 Suppl 2):S3-23 (2010).
Chua et al., "Chapter 40: Production of Monoclonal Antibody by DNA Immunization with Electroporation," S. Li (ed.), Electroporation Protocols: Preclinical and Clinical Gene Medicine. From Methods in Molecular Biology. 423:509-20 (2008).
Contini et al., "Soluble HLA-A,-B,-C and -G molecules induce apoptosis in T and Nk CD8+ cells and inhibit cytotoxic T cell activity through CD8 ligation," Eur J Immunol. 33:125-34 (2003).
Deng et al., "Enhancing antibody patent protection using epitope mapping information," MABS 10(2):204-209 (2018) (published online: Dec. 7, 2017).
Desai et al., "Structural Relatedness of Distinct Determinants Recognized by Monoclonal Antibody TP25.99 on beta2-Microglobulin-Associated and beta2-Microglobulin-Free HLA Class I Heavy Chains," J Immunol. 165:3275-83 (2000).
Diaz-Lagares et al., "Nitric oxide produces HLA-G nitration and induces metalloprotease-dependent shedding creating a tolerogenic milieu," Immunology. 126(3):436-45 (2008).
Donadi et al., "Implications of the polymorphism of HLA-G on its function, regulation, evolution and disease association," Cell Mol Life Sci. 68:369-95 (2011).
Fioretti et al., "DNA Vaccines: Developing New Strategies against Cancer," J Biomed Biotechnol. 2010:174378 (2010) (16 pages).
Furukawa et al., "Evaluation of the Reactivity and Receptor Competition of HLA-G Isoforms toward Available Antibodies: Implications of Structural Characteristics of HLA-G Isoforms," Int J Mol Sci. 20:5947 (Nov. 26, 2019).
Gauster et al., "Monoclonal antibody HC10 does not bind HLA-G," Rheumatology. 46:892-3 (2007).
Geraghty et al., "A human major histocompatibility complex class I gene that encodes a protein with a shortened cytoplasmic segment," Proc Natl Acad Sci USA. 84(1):9145-9 (Dec. 1987).
Ishitani et al., "Protein Expression and Peptide Binding Suggest Unique and Interacting Functional Roles for Hla-E, F, and G in Maternal-Placental Immune Recognition," J Immunol. 171(3):1376-84 (2003).
Kobayashi et al., "Establishment of a Choriocarcinoma Model from Immortalized Normal Extravillous Trophoblast Cells Transduced with HRASV12," Am J Pathol. 179(3):1471-82 (2011).
Kovats et al., "A Class I Antigen, HLA-G, Expressed in Human Trophoblasts," Science 248:220- 223 (1990).
Kutzler et al., "DNA vaccines: ready for prime time?" Nat Rev Genet. 9(10):776-88 (2008).
Laddy et al., "From Plasmids to Protection: A Review of DNA Vaccines Against Infectious Diseases," International Reviews of Immunology. 25:99-123 (2006) (26 pages).
Le Discorde et al., " HLA-G*0105N Null Allele Encodes Functional HLA-G Isoforms," Biol Reprod. 73(2):280-8 (2005).
Le Gal et al., "HLA-G-mediated inhibition of antigen-specific cytotoxic T lymphocytes," International Immunology. 11(8):1351-6 (1999).
Le Rond et al., "Alloreactive CD4+ and CD8+ T cells express the immunotolerant HLA-G molecule in mixed lymphocyte reactions: in vivo implications in transplanted patients," Eur J Immunol. 34(3):649-60 (2004).
Lee et al., "The Membrane-Bound and Soluble Forms of HLA-G Bind Identical Sets of Endogenous Peptides but Differ with Respect to TAP Association," Immunity. 3:591-600 (1995).
Liang et al., "HLA-G inhibits the functoins of murine dendritic cells via the PIR-B immune inhibitory receptor," Eur J Immunol. 32:2418-26 (2002).
Lin et al., "HLA-G expression in human ovarian carcinoma counteracts NK cell function," Annals of Oncology. 18(11):1804-9 (2007).
Loke et al., "Evaluation of trophoblast HLA-G antigen with a specific monoclonal antibody," Tissue Antigens. 50:135-46 (1997).
Loumagne et al., "In vivo evidence that secretion of HLA-G by immunogenic tumor cells allows their evasion from immunosurveillance," Int J Cancer. 135:2107-17 (2014).
Loustau et al., "HLA-G Neo-Expression on Tumors," Frontiers in Immunology. 11(1685) (Aug. 14, 2020) (15 pages).
Mansfield et al., "Regional immunity in melanoma: immunosuppressive changes precede nodal metastasis," Modern Pathol. 24:487-94 (2011).
Markel et al., "Preclinical Evaluation of Adoptive Cell Therapy for Patients with Metastatic Renal Cell Carcinoma," Anticancer Res. 29:145-54 (2009).
Matsushita et al., "Differential but Competitive Binding of Nogo Protein and Class I Major Histocompatibility Complex (MHCI) to the PIR-B Ectodomain Provides an Inhibition of Cells," J Biol Chem. 286(29):25739-47 (2011).
McMaster et al., "HLA-G Isoforms Produced by Placental Cytotrophoblasts and Found in Amniotic Fluid Are Due to Unusual Glycosylation," J Immunol. 160(12):5922-8 (1998).
Molek et al., "Epitope Mapping of Mono- and Polyclonal Antibodies by Screening Phage-displayed Random Peptide Libraries," Acta Chim Slov. 63:914-9 (2016).
Morales et al., "Placental Cell Expression of HLA-G2 Isoforms Is Limited to the Invasive Trophoblast Phenotype," J Immunol. 171(11): 6215-24 (2003).
Naji et al., "Soluble HLA-G and HLA-G1 Expressing Antigen-Presenting Cells Inhibit T-Cell Alloproliferation through ILT-2/ILT-4/FasL-Mediated Pathways," Hum Immunol. 68(4):233-9 (2007).
Nencioni et al., "Anticancer vaccination strategies," Ann Oncol. 15(Supplement 4):iv153-iv160 (2004).
Nimmerjahn et al., "Fcgamma receptors as regulators of immune responses," Nature Reviews Immunology 8:34-47 (2008).
Nordic-MUbio Product Datasheet for "Mouse anti Human HLA Class I Heavy Chain (Restricted expression)." Catalogue No. MUB2037P (3 pages).
Parish et al., "Immunogenicity of Low-Dose Intradermal Recombinant DNA Hepatitis B Vaccine," Southern Med J. 84(4):426-30 (1991).
Paul et al., "HLA-G expression in melanoma: A way for tumor cells to escape from immunosurveillance," Proc Natl Acad Sci USA. 95(8):4510-5 (1998).
Paul et al., "Hla-G, -E, -F Preworkshop: Tools and Protocols for Analysis of Non-Classical Class I Genes Transcription and Protein Expression," Human Immunology. 61(11): 1177-95 (2000).
Pelanda et al., "Central B-Cell Tolerance: Where Selection Begins," Cold Spring Harb Perspect Biol. 4(4):a007146 (2012) (16 pages).
Pirrone et al., "Applications of Hydrogen/Deuterium Exchange MS from 2012 to 2014," Anal. Chem. 87:99-118 (2015).
Product datasheets for HLA-G monoclonal antibody (MEM-G/4) from GeneTex (catalogue No. GTX21887), ThermoFisher Scientific (catalogue No. MA1-19358), and Abcore (product No. 11-394) (5 pages).
Riteau et al., "HLA-G2, -G3, and -G4 Isoforms Expressed as Nonmature Cell Surface Glycoproteins Inhibit NK and Antigen-Specific CTL Cytosis," J Immunol. 166:5018-26 (2001) (10 pages).
Rouas-Freiss et al., "Expression of tolerogenic HLA-G molecules in cancer prevents antitumor responses," Seminars in Cancer Biol. 17:413-21 (2007).

(56) References Cited

OTHER PUBLICATIONS

Saade et al., "Technologies for enhanced efficacy of DNA vaccines," Expert Rev Vaccines. 11(2):189-209 (2012).

Seitz et al., "The monoclonal antibody HCA2 recognises a broadly shared epitope on a selected classical as well as several nonclassical HLA class I molecules," Mol Immunol. 35:819-27 (1998).

Shiroishi et al., "Structural basis for recognition of the nonclassical MHC molecule HLA-G by the leukocyte Ig-like receptor B2 (LILRB2/LIR2/ILT4/CD85d)," PNAS. 103(44): 16412-7 (2006).

Tanabe et al., "Structural and Functional Analysis of Monomorphic Determinants Recognized by Monoclonal Antibodies Reacting with the HLA Class I alpha$_3$ Domain," Journal of Immunology. 148(13):3202-9 (1992).

Temming et al., "Cross-reactivity of mouse IgG subclasses to human Fc gamma receptors: Antibody deglycosylation only eliminates IgG2b binding," Molecular Immunology 127:79-86 (Sep. 2020).

Tran et al., "The epitope recognized by pan-HLA class I-reactive monoclonal antibody W6/32 and its relationship to unusual stability of the HLA-B27/Beta2-microglobulin complex," Immunogenetics. 53:440-6 (2001).

Tuting et al., "The Immunology of DNA Vaccines," excerpt from "DNA Vaccines: Methods and Protocols." 29:37-8 (2000) (3 pages).

Van Lierop et al., "Detection of HLA-G by a specific sandwich ELISA using monoclonal antibodies G233 and 56B," Mol Hum Reprod. 8(8):776-84 (2002).

Vergati et al., "Strategies for Cancer Vaccine Development," J Biomed Biotechnol. 2010:596432 (2010) (13 pages).

Vlieg et al., "Structure and flexibility of the extracellular region of the PirB receptor," J. Biol. Chem. 294(12): 4634-4643 (Jan. 2019).

Xing et al., "T-Cell Tolerance: Central and Peripheral," Cold Spring Harb Perspect Biol. 4(6):a006957 (2012) (16 pages).

Yari et al., "Production and Characterization of Monoclonal Antibodies with Specificity for Human HLA-G Isoforms," Hybridoma and Hybridomics. 22(5):301-6 (2003).

Ye et al., "Human leukocyte antigen G expression: as a significant prognostic indicator for patients with colorectal cancer," Modern Pathology. 20(3):375-83 (2007).

Zöller et al., "Prophylactic Tumor Vaccination: Comparison of Effector Mechanisms Initiated by Protein Versus DNA Vaccination," J Immunol. 166:3440-50 (2001).

* cited by examiner

Fig. 2A

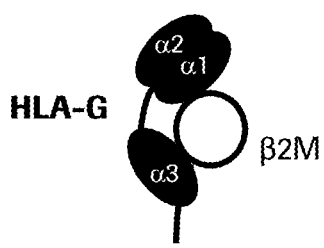

Schematic representation of the HLA-G wt molecule

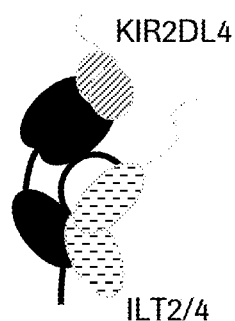

The KIR2DL4 and ILT2/4 interactions are extracted from crystal structures: the HLA-G:ILT4 complex structure (PDB code: 2DYP). The KIR2DL1 structure is taken from PDB code 1IM9 (KIR2DL1:HLA-Cw4 complex structure) and was positioned on HLA-G by superposition of the HLA-Cw4 and HLA-G structures.

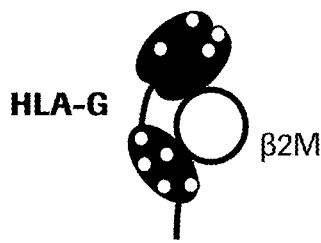

Schematic representation of the HLA-G chimeric molecule that was used as a counter antigen for the identification of specific HLA-G binders. White dots represent surface residues that were identified as unique for HLA-G. These residues were replaced by a HLA consensus sequence in the chimeric molecule.

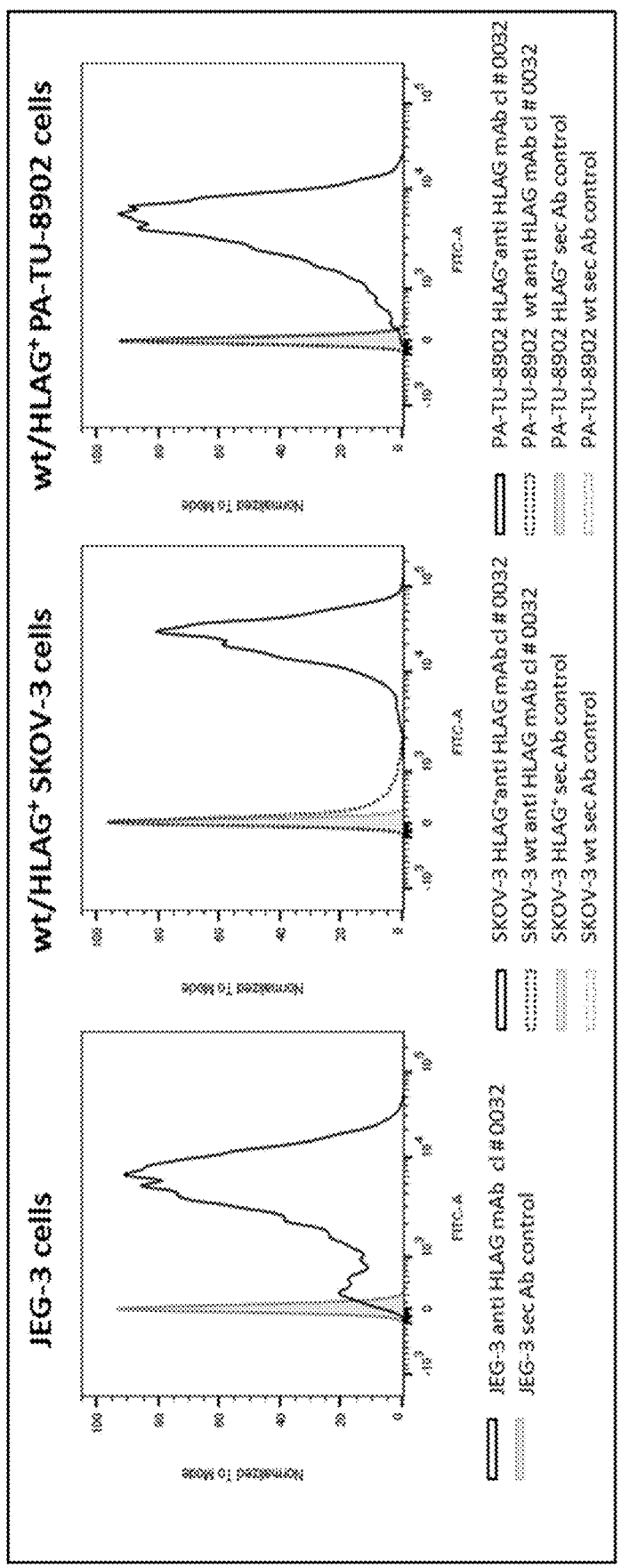

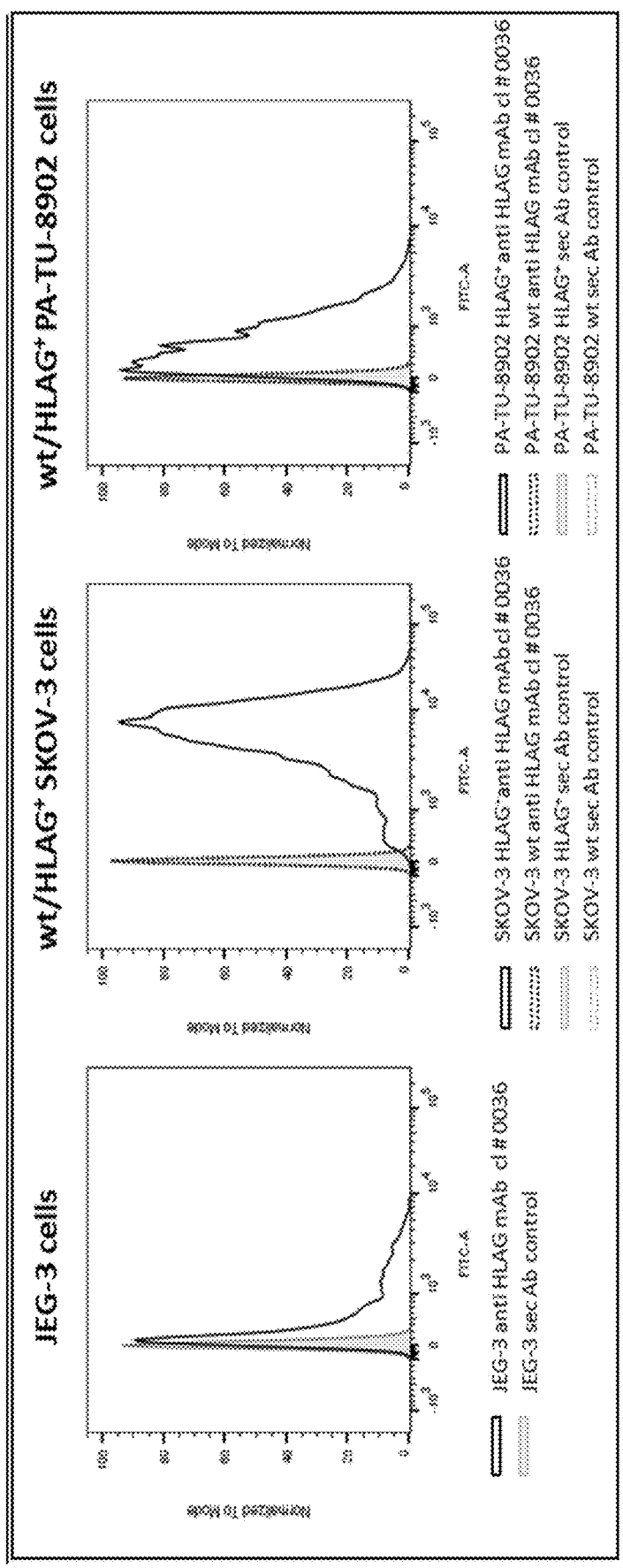

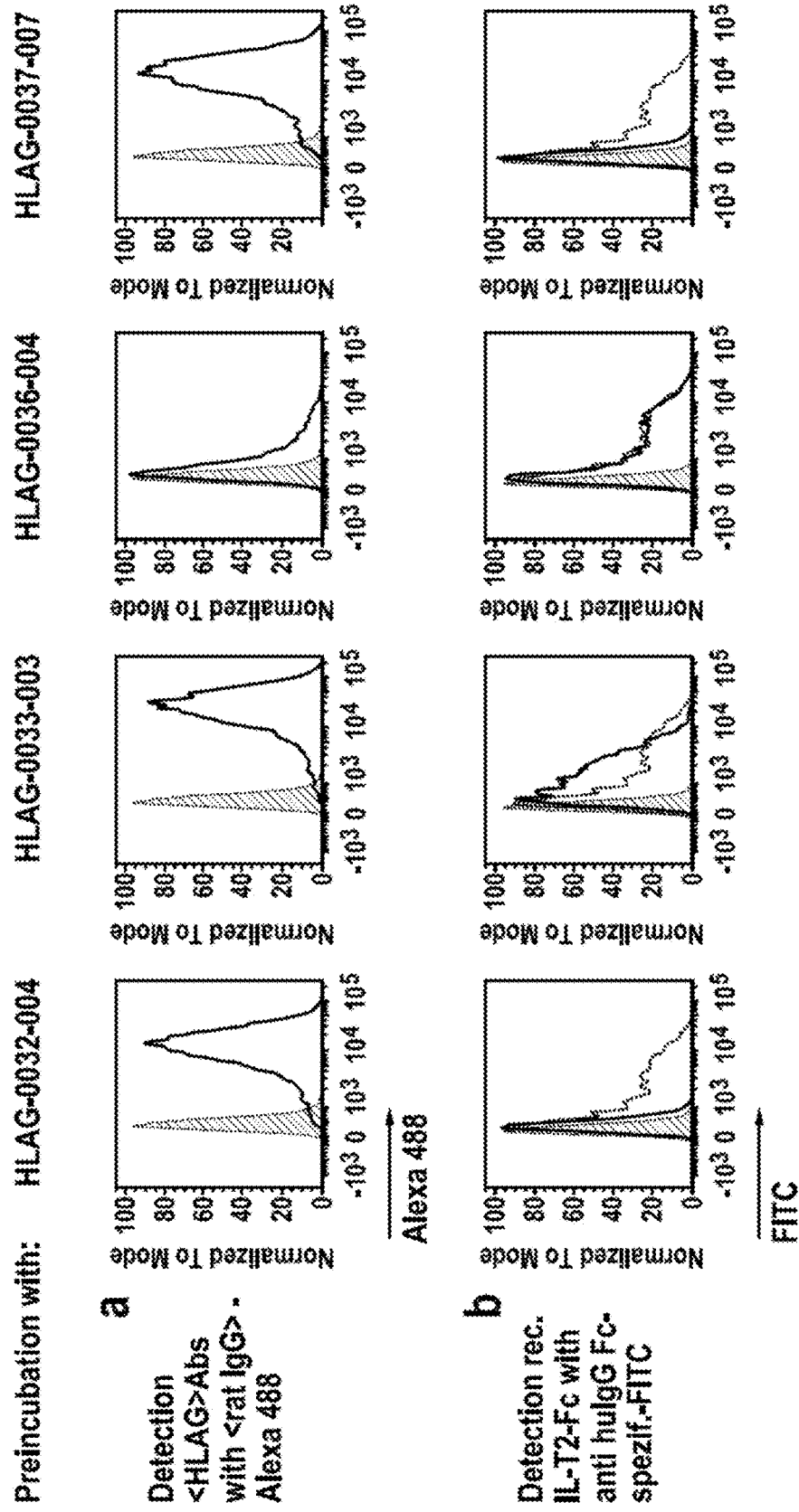

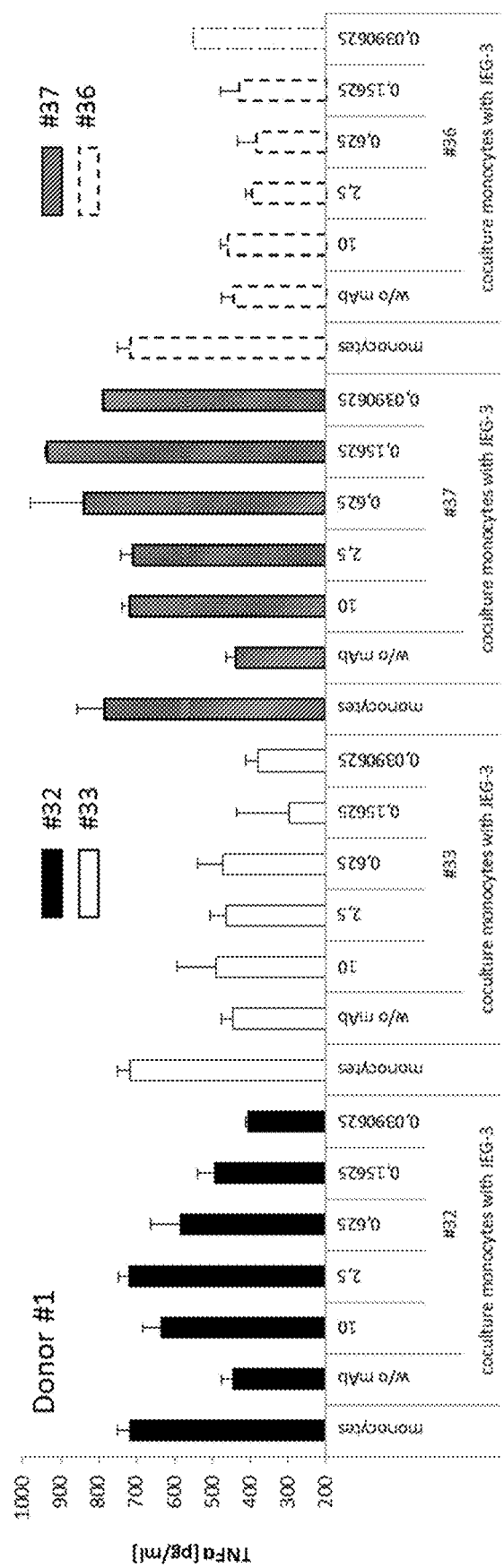

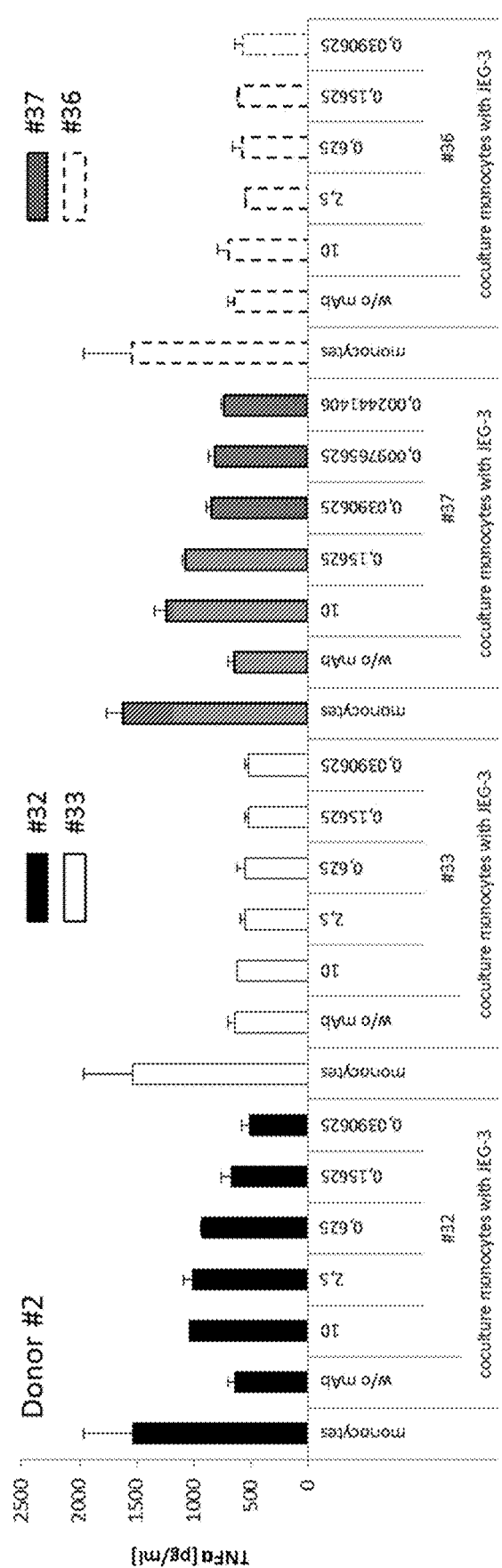

ANTI-HLA-G ANTIBODIES AND USE THEREOF

CROSS-REFERENCE TO RELATED APPLICATIONS

This application is a continuation of International Application No. PCT/EP2017/079429, filed on Nov. 16, 2017, which claims priority from European Patent Application No. 16199620.2 filed on Nov. 18, 2016. The contents of each of the foregoing applications are incorporated herein by reference in their entireties.

SEQUENCE LISTING

The present application contains a Sequence Listing which has been submitted electronically as a text file in ASCII format and is hereby incorporated by reference in its entirety. Said text file, created on May 17, 2019, is named P33980-US_seqlisting.txt and is 62,034 bytes in size.

The present invention relates to anti-HLA-G antibodies and methods of using the same.

BACKGROUND OF THE INVENTION

The human major histocompatability complex, class I, 6, also known as human leukocyte antigen G (HLA-G), is a protein that in humans is encoded by the HLA-G gene. HLA-G belongs to the HLA nonclassical class I heavy chain paralogues. This class I molecule is a heterodimer consisting of a heavy chain and a light chain (beta-2 microglobulin). The heavy chain is anchored in the membrane but can also be shedded/secreted.

The heavy chain consists of three domains: alpha 1, alpha 2 and alpha 3. The alpha 1 and alpha 2 domains form a peptide binding groove flanked by two alpha helices. Small peptides (approximately 9-mers) can bind to this groove akin to other MHC I proteins.

The second chain is beta 2 microglobulin which binds to the heavy chain similar to other MHC I proteins.

For HLA-G there exist 7 isoforms, 3 secreted and 4 membrane bound forms (as schematically shown in FIG. 1).

HLA-G can form functionally active complex oligomeric structures (Kuroki, K et al. Eur J Immunol. 37 (2007) 1727-1729). Disulfide-linked dimers are formed between Cys 42 of two HLA-G molecules. (Shiroishi Metal., J Biol Chem 281 (2006) 10439-10447. Trimers and Tetrameric complexes have also been described e.g. in Kuroki, K et al. Eur J Immunol. 37 (2007) 1727-1729, Allan D. S., et al. J Immunol Methods. 268 (2002) 43-50 and T Gonen-Gross et al., J Immunol 171 (2003)1343-1351).

HLA-G is predominantly expressed on cytotrophoblasts in the placenta. Several tumors (including pancreatic, breast, skin, colorectal, gastric & ovarian) express HLA-G (Lin, A. et al., Mol Med. 21 (2015) 782-791; Amiot, L., et al., Cell Mol Life Sci. 68 (2011) 417-431). The expression has also been reported to be associated with pathological conditions like inflammatory diseases, GvHD and cancer. Expression of HLA-G has been reported to be associated with poor prognosis in cancer. Tumor cells escape host immune surveillance by inducing immune tolerance/suppression via HLA-G expression.

| Overview polymorphisms HLA family | | |
|---|---|---|
| HLA-A: | 2579 seqs | |
| HLA-B: | 3283 seqs | classical class I MHC |
| HLA-C: | 2133 seqs | |
| HLA-E: | 15 seqs | |
| HLA-F: | 22 seqs | non-classical class I MHC |
| HLA-G: | 50 seqs | |

HLA-G shares high homology (>98%) with other MHC I molecules, therefore truly HLA-G specific antibodies with no crossreactivity to other MHC I molecules are difficult to generate.

Certain antibodies which interact in different ways with HLA-G were described previously: Tissue Antigens, 55 (2000) 510-518 relates to monoclonal antibodies e.g. 87G, and MEM-G/9; Neoplasma 50 (2003) 331-338 relates to certain monoclonal antibodies recognizing both, intact HLA-G oligomeric complex (e.g. 87G and MEM-G9) as well as HLA-G free heavy chain (e.g. 4H84, MEM-G/1 and MEM-G/2); Hum Immunol. 64 (2003) 315-326 relates to several antibodies tested on HLA-G expressing JEG3 tumor cells (e.g. MEM-G/09 and -G/13 which react exclusively with native HLA-G1 molecules. MEM-G/01 recognizes (similar to the 4H84 mAb) the denatured HLA-G heavy chain of all isoforms, whereas MEM-G/04 recognizes selectively denatured HLA-G1, -G2, and -G5 isoforms; Wiendl et al Brain 2003 176-85 relates to different monoclonal HLA-G antibodies as e.g. 87G, 4H84, MEM-G/9.

The above publications report antibodies, which bind to human HLA-G or the human HLA-G/ß2M MHC complex. However, due to the high polymorphism and high homology of the HLA family most of the antibodies lack either truly specific HLA-G binding properties and often also bind or crossreact with other HLA family members (either as MHC complex with ß2M or in its ß2M-free form) or they simply do not inhibit binding of HLA-G ß2M MHC complex to its receptors ILT2 and/or ILT4 (and are regarded as non-antagonistic antibodies). Hence there is the need to generate and/or select further improved, truly HLA-G specific antibodies with receptor blocking properties.

SUMMARY OF THE INVENTION

The present invention provides tailor-made chimeric antigens and/or stringent screening assays to identify HLA-G specific antibodies among numerous candidates (avoiding cross-reactivity to other MHC class I complex molecules and at the same time selecting HLA-G receptor (such as ILT2) blocking antibodies).

The invention provides a kit of
  monomeric wildtype human HLA-G ß2M MHC I complex comprising SEQ ID NO: 25; and
  monomeric modified HLA-G ß2M MHC I complex comprising SEQ ID NO: 26 (wherein the HLA-G specific amino acids have been replaced by HLA consensus amino acids of all HLA-As; and
  ILT2
  ILT4
to screen for human HLA-G ß2M MHC complex specific antibodies, which show no crossreactivity with other HLA-A family proteins and inhibit binding of HLA-G to one of its receptors ILT2 and/or ILT4

The invention provides an isolated antibody that binds to human HLA-G, wherein the antibody that specifically binds to human HLA-G, wherein the antibody binds to human HLA-G ß2M MHC I complex comprising SEQ ID NO: 25.

In one preferred embodiment the anti-HLA-G antibody inhibits ILT2 binding to monomeric HLA-G ß2M MHC I complex.

In another preferred embodiment the anti-HLA-G antibody inhibits ILT2 binding to monomeric HLA-G ß2M MHC I complex by more than 50% (when compared to the binding without antibody).

In one embodiment the anti-HLA-G antibody inhibits ILT2 binding to monomeric and/or dimeric and/or trimeric HLA-G ß2M MHC I complex by more than 70% (when compared to the binding without antibody).

In another preferred embodiment the anti-HLA-G antibody of the invention binds to human HLA-G on JEG3 cells inhibits ILT2 binding to HLA-G on JEG3 cells (by more than 50%) (when compared to the binding without antibody).

In one embodiment the anti-HLA-G antibody does not crossreact with (does not specifically bind to) a modified human HLA-G ß2M MHC I complex comprising SEQ ID NO:26; and In one embodiment the anti-HLA-G antibody does not crossreact with (does not specifically bind to) a mouse H2Kd ß2M MHC I complex comprising SEQ ID NO:27 and/or does not crossreact with (does not specifically bind to) rat RT1A ß2M MHC I complex comprising SEQ ID NO:29.

In one embodiment the anti-HLA-G antibody does not crossreact with (does not specifically bind to) human HLA-A2 ß2M MHC I complex comprising SEQ ID NO:21 and SEQ ID NO: 19.

One embodiment of the invention is an isolated antibody that binds to human HLA-G, wherein the antibody comprises A) (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6; or B) (a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.

One embodiment of the invention is an isolated antibody that binds to human HLA-G, wherein the antibody comprises A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14.

One embodiment of the invention is an isolated antibody that binds to human HLA-G, wherein the antibody A)
  i) comprises a VH sequence of SEQ ID NO:7 and a VL sequence of SEQ ID NO:8;
  ii) or humanized variant of the VH and VL of the antibody under i);
or B)
  i) comprises a VH sequence of SEQ ID NO:15 and a VL sequence of SEQ ID NO:16;
  ii) or humanized variant of the VH and VL of the antibody under i);

In one embodiment the anti-HLA-G antibody is of IgG1 isotype.

In one embodiment the anti-HLA-G antibody is of IgG1 isotype with mutations L234A, L235A and P329G (numbering according to the EU index of Kabat).

In one embodiment the anti-HLA-G antibody according to the invention is a monoclonal antibody.

In one embodiment the anti-HLA-G antibody according to the invention is a human, humanized, or chimeric antibody.

In one embodiment the anti-HLA-G antibody according to the invention which is an antibody fragment that binds to HLA-G.

In one embodiment the anti-HLA-G antibody according to the invention which is Fab fragment.

The invention provides an isolated nucleic acid encoding the antibody according to any one of the preceding claims.

The invention provides a host cell comprising such nucleic acid.

The invention provides a method of producing an antibody comprising culturing the host cell so that the antibody is produced.

The invention provides such method of producing an antibody, further comprising recovering the antibody from the host cell.

The invention provides a pharmaceutical formulation comprising the antibody described herein and a pharmaceutically acceptable carrier.

The invention provides the antibody described herein for use as a medicament.

The invention provides the antibody described herein for use in treating cancer.

The invention provides the use of the antibody described herein in the manufacture of a medicament. In one embodiment the medicament is for treatment of cancer.

The invention provides a method of treating an individual having cancer comprising administering to the individual an effective amount of the antibody described herein.

With the screening methods according to the invention the new anti-HLA-G antibodies be selected. These antibodies show highly valuable properties like strong inhibition of ILT2 binding to HLA-G expressed on JEG3 cells or inhibition of ILT2 binding to monomeric and/or dimeric and/or trimeric HLA-G ß2M MHC I complex. Furthermore, the antibodies according to the invention are able to restore a suppressed immune response, i.e. restoration of LPS-induced TNFa production by monocytes in co-culture with HLA-G-expressing cells. In addition, the antibodies are highly specific and to not show cross reactivity with HLA-A MHC I complexes or MHC I complexes from mouse or rat origin.

DESCRIPTION OF THE FIGURES

FIG. 2A: Schematic representation of HLA-G with molecule in association with ß2M

FIG. 3A: HLA-G-0032 and HLA-G-0033):
FIG. 3B: HLA-G-0036 and HLA-G-0037

FIG. 4A: ILT2 inhibition
FIG. 4B: ILT4 inhibition
FIG. 5A, FIG. 5B, FIG. 5C, and FIG. 5D:
Flow cytometric analysis of cell surface expression of HLA-G using HLA-G antibodies on JEG3 (cells naturally expressing HLA-G), SKOV-3 cells (wild-type (wt) versus HLAG transfected cells (HLAG+)), and PA-TU-8902 cells (wild-type (wt) versus HLAG transfected cells (HLAG+)):

FIG. 5A: HLA-G-0032 (#0032); FIG. 5B: HLA-G-0033 (#0033);
FIG. 5C: HLA-G-0036 (#0036): FIG. 5D: HLA-G-0037 (#0037)

FIG. 6A and FIG. 6B:
FIG. 6A: Anti-HLA-G antibodies block/modulate interaction of human ILT2 Fc chimera with HLA-G expressed on JEG3 cells: The staining of cell surface HLA-G with the novel anti-HLA-G antibodies was assessed by using an anti-rat IgG secondary antibody conjugated to Alexa488 (a). Shown in the FACS histograms are cells stained with secondary antibody alone (grey dotted lines) and cell stained with anti-HLA-G antibodies (black solid lines). In the lower row (b) human ILT2-Fc bound to HLA-G on JEG3 cells is depicted (black dotted line) in comparison to cells stained with secondary antibody alone (grey dotted line). The impact of pre-incubating JEG3 cells with HLA-G antibodies on ILT2 Fc chimera binding can been seen (black solid line): HLA-G-0032 and HLA-G-0037 showed nearly complete inhibition of binding of ILT2-Fc chimera to JEG3 cells.

FIG. 6B: Impact of commercial/reference anti-HLA-G antibodies on ILT2 Fc chimera binding to HLA-G on JEG3 cells: The staining of cell surface HLA-G with commercial/reference anti-HLA-G antibodies was assessed by using a species-specific secondary antibody conjugated to Alexa488 (a). Shown in the FACS histograms are cells stained with secondary antibody alone (grey dotted lines) and cell stained with anti-HLA-G antibodies (black solid lines). In the lower row (b) human ILT2 Fc chimera bound to HLA-G on JEG3 cells is depicted (black dotted line) in comparison to cells stained with secondary antibody alone (grey dotted line). The impact of pre-incubating JEG3 cells with reference antibodies on ILT2 Fc chimera binding can been seen (black solid line). None of the tested reference antibodies could block the interaction of ILT2 Fc chimera with cell surface HLA-G on JEG3 cells.

FIG. 7A and FIG. 7B:
The impact of the blockade of HLA-G with inhibitory anti-HLA-G antibodies on the restoration of TNFα production two donors #
FIG. 7A: donors #1
FIG. 7B: donors #2

DETAILED DESCRIPTION OF THE INVENTION

Figure 1:
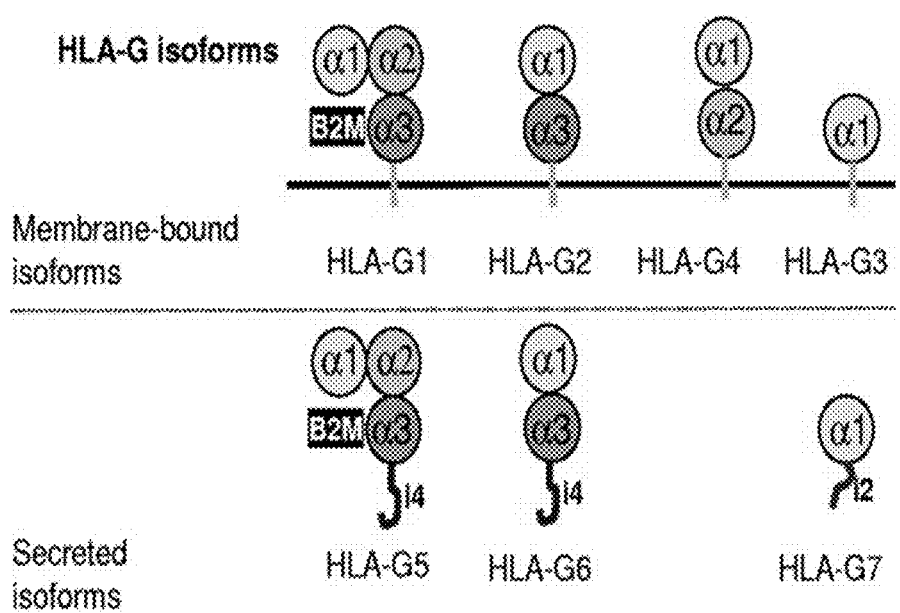
FIG. 1: Different isoforms of HLA-G
FIG. 2A and FIG. 2B.
Figure 2B:
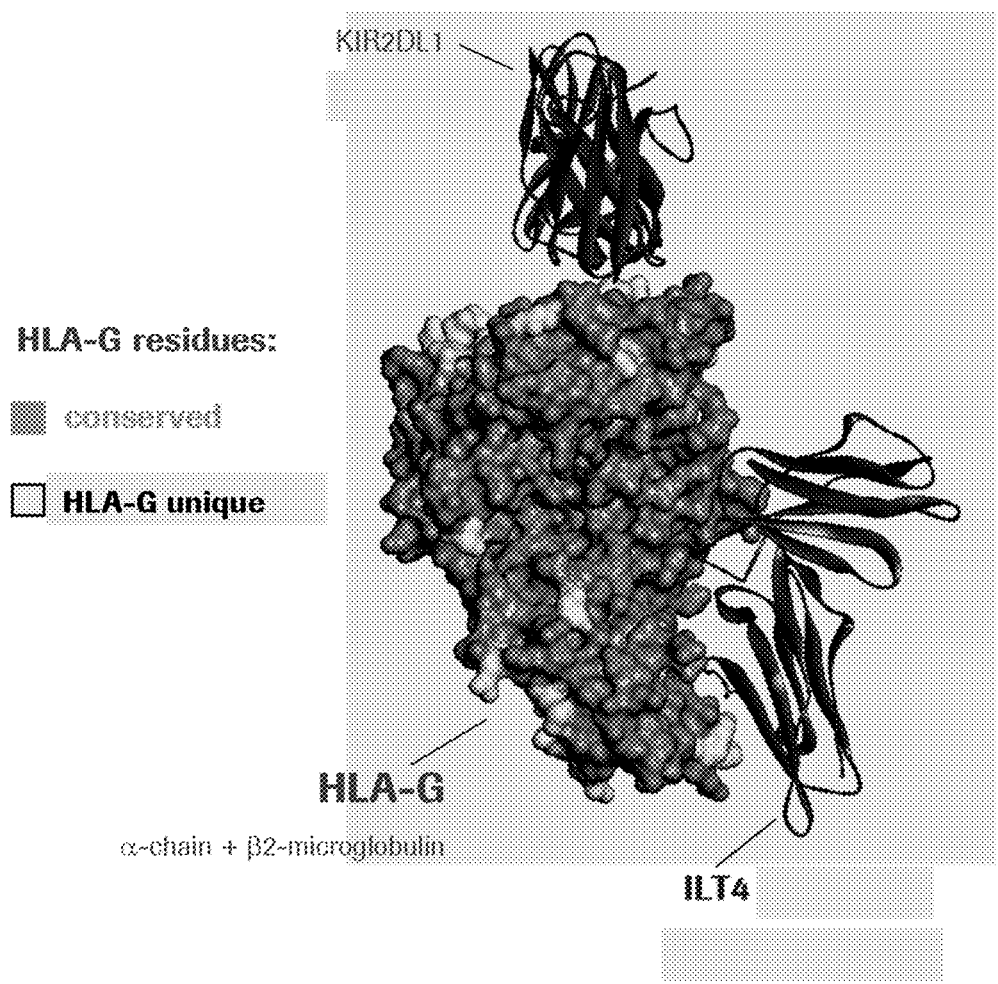
FIG. 2B: Structure of HLA-G molecule in association with certain receptors: HLA-G structure in complex with given receptors such as ILT4 and KIR2DL1. ILT4 structure (PDB code: 2DYP). The KIR2DL1 structure is taken from PDB code 1IM9 (KIR2DL1: HLA-Cw4 complex structure) and was positioned on HLA-G by superposition of the HLA-Cw4 and HLA-G structures. Receptors are shown in a ribbon representation, HLA-G is shown in a molecular surface representation. HLA-G residues that are unique or conserved in other HLA paralogs are colored in white and gray, respectively. Unique surface residues were replaced by a HLA consensus sequence in the chimeric counter antigen.

When used herein, the term "HLA-G", "human HLA-G", refers to the HLA-G human major histocompatability complex, class I, G, also known as human leukocyte antigen G (HLA-G) (exemplary SEQ ID NO: 17). Typically, HLA-G forms a MHC class I complex together with ß2 microglobulin (B2M or ß2m). In one embodiment HLA-G refers to the MHC class I complex of HLA-G and ß2 microglobulin.

As used herein, an antibody "binding to human HLA-G", "specifically binding to human HLA-G", "that binds to human HLA-G" or "anti-HLA-G antibody" refers to an antibody specifically binding to the human HLA-G antigen or its extracellular domain (ECD) with a binding affinity of a $K_D$-value of $5.0\times10^{-8}$ mol/l or lower, in one embodiment of a $K_D$-value of $1.0\times10^{-9}$ mol/l or lower, in one embodiment of a $K_D$-value of $5.0\times10^{-8}$ mol/l to $1.0\times10^{-13}$ mol/l. The binding affinity is determined with a standard binding assay, such as surface plasmon resonance technique (BIAcore®, GE-Healthcare Uppsala, Sweden) e.g. using constructs comprising HLA-G extracellular domain (e.g. in its natural occurring 3 dimensional structure). In one embodiment binding affinity is determined with a standard binding assay using exemplary soluble HLA-G comprising MHC class I complex comprising SEQ ID NO: 25.

HLA-G has the regular MHC I fold and consists of two chains: Chain 1 consists of three domains: alpha 1, alpha 2 and alpha 3. The alpha 1 and alpha 2 domains form a peptide binding groove flanked by two alpha helices. Small peptides (approximately 9mers) can bind to this groove akin to other MHCI proteins. Chain 2 is beta 2 microglobulin which is shared with various other MHCI proteins.

HLA-G can form functionally active complex oligomeric structures (Kuroki, K et al. Eur J Immunol. 37 (2007) 1727-1729). Disulfide-linked dimers are formed between Cys 42 of two HLA-G molecules. (Shiroishi Metal., J Biol Chem 281 (2006) 10439-10447. Trimers and Tetrameric complexes have also been described e.g. in Kuroki, K et al. Eur J Immunol. 37 (2007) 1727-1729, Allan D. S., et al. J Immunol Methods. 268 (2002) 43-50 and T Gonen-Gross et al., J Immunol 171 (2003)1343-1351). HLA-G has several free cysteine residues, unlike most of the other MHC class I molecules. Boyson et al., Proc Nat Acad Sci USA, 99: 16180 (2002) reported that the recombinant soluble form of HLA-G5 could form a disulfide-linked dimer with the intermolecular Cys42-Cys42 disulfide bond. In addition, the membrane-bound form of HLA-G1 can also form a disulfide-linked dimer on the cell surface of the Jeg3 cell line, which endogenously expresses HLA-G. Disulfide-linked dimer forms of HLA-G1 and HLA-G5 have been found on the cell surface of trophoblast cells as well (Apps, R., Tissue Antigens, 68:359 (2006)).

HLA-G is predominantly expressed on cytotrophoblasts in the placenta. Several tumors (including pancreatic, breast, skin, colorectal, gastric & ovarian) express HLA-G (Lin, A. et al., Mol Med. 21 (2015) 782-791; Amiot, L., et al., Cell Mol Life Sci. 68 (2011) 417-431). The expression has also been reported to be associated with pathological conditions like inflammatory diseases, GvHD and cancer. Expression of HLA-G has been reported to be associated with poor prognosis in cancer. Tumor cells escape host immune surveillance by inducing immune tolerance/suppression via HLA-G expression.

For HLA-G there exist 7 isoforms, 3 secreted and 4 membrane bound forms (as schematically shown in FIG. 1). The most important functional isoforms of HLA-G include b2-microglobulin-associated HLA-G1 and HLA-G5. However, the tolerogenic immunological effect of these isoforms is different and is dependent on the form (monomer, dimer) of ligands and the affinity of the ligand-receptor interaction.

HLA-G protein can be produced using standard molecular biology techniques. The nucleic acid sequence for HLA-G isoforms is known in the art. See for example GENBANK Accession No. AY359818.

The HLA-G isomeric forms promote signal transduction through ILTs, in particular ILT2, ILT4, or a combination thereof.

ILTs: ILTs represent Ig types of activating and inhibitory receptors that are involved in regulation of immune cell activation and control the function of immune cells (Borges, L., et al., Curr Top Microbial Immunol, 244:123-136 (1999)). ILTs are categorized into three groups: (i) inhibitory, those containing a cytoplasmic immunoreceptor tyrosine-based inhibitory motif (ITIM) and transducing an inhibitory signal (ILT2, ILT3, ILT4, ILT5, and LIR8); (ii) activating, those containing a short cytoplasmic tail and a charged amino acid residue in the transmembrane domain (ILT1, ILT7, ILT8, and LIR6alpha) and delivering an activating signal through the cytoplasmic immunoreceptor tyrosine-based activating motif (ITAM) of the associated common gamma chain of Fc receptor; and (iii) the soluble molecule ILT6 lacking the transmembrane domain. A number of recent studies have highlighted immunoregulatory roles for ILTs on the surface of antigen presenting cells (APC). ILT2, ILT3, and ILT4 receptors, the most characterized immune inhibitory receptors, are expressed predominantly on myeloid and plasmacytoid DC. ILT3 and ILT4 are upregulated by exposing immature DC to known immunosuppressive factors, including IL-10, vitamin D3, or suppressor CD8 T cells (Chang, C. C., et al., Nat Immunol, 3:237-243 (2002)). The expression of ILTs on DC is tightly controlled by inflammatory stimuli, cytokines, and growth factors, and is down-regulated following DC activation (Ju, X. S., et al., Gene, 331:159-164 (2004)). The expression of ILT2 and ILT4 receptors is highly regulated by histone acetylation, which contributes to strictly controlled gene expression exclusively in the myeloid lineage of cells (Nakajima, H., J Immunol, 171:6611-6620 (2003)).

Engagement of the inhibitory receptors ILT2 and ILT4 alters the cytokine and chemokine secretion profile of monocytes and can inhibit Fc receptor signaling (Colonna, M., et al. J Leukoc Biol, 66:375-381 (1999)). The role and function of ILT3 on DC have been precisely described by the Suciu-Foca group (Suciu-Foca, N., Int Immunopharmacol, 5:7-11 (2005)). Although the ligand for ILT3 is unknown, ILT4 is known to bind to the third domain of HLA class I molecules (HLA-A, HLA-B, HLA-C, and HLA-G), competing with CD8 for MHC class I binding (Shiroishi, M., Proc Natl Acad Sci USA, 100:8856-8861 (2003)). The preferential ligand for several inhibitory ILT receptors is HLA-G. HLA-G plays a potential role in maternal-fetal tolerance and in the mechanisms of escape of tumor cells from immune recognition and destruction (Hunt, J. S., et al., Faseb J, 19:681-693 (2005)). It is most likely that regulation of DC function by HLA-G-ILT interactions is an important pathway in the biology of DC. It has been determined that human monocyte-derived DC that highly express ILT2 and ILT4 receptors, when treated with HLA-G and stimulated with allogeneic T cells, still maintain a stable tolerogenic-like phenotype (CD80low, CD86low, HLA-DRlow) with the potential to induce T cell anergy (Ristich, V., et al., Eur J Immunol, 35:1133-1142 (2005)). Moreover, the HLA-G interaction with DC that highly express ILT2 and ILT4 receptors resulted in down-regulation of several genes involved in the MHC class II presentation pathway. A lysosomal thiol reductase, IFN-gamma inducible lysosomal thiol reductase (GILT), abundantly expressed by professional APC, was greatly reduced in HLA-G-modified DC. The repertoire of primed CD4+ T cells can be influenced by DC expression of GILT, as in vivo T cell responses to select antigens were reduced in animals lacking GILT after targeted gene disruption (Marie, M., et al., Science, 294:1361-1365 (2001)). The HLA-G/ILT interaction on DC interferes with the assembly and transport of MHC class II molecules to the cell surface, which might result in less efficient presentation or expression of structurally abnormal MHC class II molecules. It was determined that HLA-G markedly decreased the transcription of invariant chain (CD74), HLA-DMA, and HLA-DMB genes on human monocyte-derived DC highly expressing ILT inhibitory receptors (Ristich, V., et al; Eur J Immunol 35:1133-1142 (2005)).

Another receptor of HLA-G is KIR2DL4 because KIR2DL4 binds to cells expressing HLA-G (US2003232051; Cantoni, C. et al. Eur J Immunol 28 (1998) 1980; Rajagopalan, S. and E. O. Long. [published erratum appears in J Exp Med 191 (2000) 2027] J Exp Med 189 (1999) 1093; Ponte, M. et al. PNAS USA 96 (1999) 5674). KIR2DL4 (also referred to as 2DL4) is a KIR family member (also designated CD158d) that shares structural features with both activating and inhibitory receptors (Selvakumar, A. et al. Tissue Antigens 48 (1996) 285). 2DL4 has a cytoplasmic ITIM, suggesting inhibitory function, and a positively charged amino acid in the transmembrane region, a feature typical of activating KIR. Unlike other clonally distributed KIRs, 2DL4 is transcribed by all NK cells (Valiante, N. M. et al. Immunity 7 (1997) 739; Cantoni, C. et al. Eur J Immunol 28 (1998) 1980; Rajagopalan, S. and E. O. Long. [published erratum appears in J Exp Med 191 (2000) 2027] J Exp Med 189 (1999) 1093).

As used herein an anti-HLA-G antibody that "does not crossreact with" or that "does not specifically bind to" a modified human HLA-G ß2M MHC I complex comprising SEQ ID NO:26; a mouse H2Kd ß2M MHC I complex comprising SEQ ID NO:27 rat RT1A ß2M MHC I complex comprising SEQ ID NO:29, human HLA-A2 ß2M MHC I complex comprising SEQ ID NO:21 and SEQ ID NO: 19 refers to an anti-HLA-G antibody that does substantially not bind to any of these counterantigens. In one embodiment an anti-HLA-G antibody that "does not crossreact with" or that "does not specifically bind to" a modified human HLA-G ß2M MHC I complex comprising SEQ ID NO:26; a mouse H2Kd ß2M MHC I complex comprising SEQ ID NO:27, a rat RT1A ß2M MHC I complex comprising SEQ ID NO:29, and/or a human HLA-A2 ß2M MHC I complex comprising SEQ ID NO:21 and SEQ ID NO: 19 refers to an anti-HLA-G antibody that shows only unspecific binding with a binding affinity of a $K_D$-value of $5.0 \times 10^{-6}$ mol/l or higher (until no more binding affinity is detectable). The binding affinity is determined with a standard binding assay, such as surface plasmon resonance technique (BIAcore®, GE-Healthcare Uppsala, Sweden) with the respective antigen: a modified human HLA-G ß2M MHC I complex comprising SEQ ID NO:26; a mouse H2Kd ß2M MHC I complex comprising SEQ ID NO:27 rat RT1A ß2M MHC I complex comprising SEQ ID NO:29, and/or a human HLA-A2 ß2M MHC I complex comprising SEQ ID NO:21 and SEQ ID NO: 19. The assay setup as well as the construction/preparation of the antigens is described in the Examples.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence. (define germlines if appropriate)

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu);

chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447), or the C-terminal glycine (Gly446) and the C-terminal lysine (Lys447), of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity see, e.g., Flatman, S. et al., *J. Chromatogr. B* 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HLA-G antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

I. Compositions and Methods

In one aspect, the invention is based, in part, on the finding that the selected anti-HLA-G antibodies of the invention bind to certain epitopes of HLA-G, and have ability to inhibit ILT2 and or ILT4 binding to HLA-G. They inhibit e.g. ILT2 binding to HLA-G and revert HLA-G mediated immune suppression by increased secretion of immunomodulatory cytokines like TNF alpha upon appropriate stimulation.

In certain embodiments, antibodies that bind to HLA-G are provided. Antibodies of the invention are useful, e.g., for the diagnosis or treatment of cancer.

A. Exemplary Anti-HLA-G Antibodies

In one aspect, the invention provides isolated antibodies that bind to human HLA-G (anti-HLA-G antibody).

In certain embodiments, an isolated antibody that specifically binds to human HLA-G is provided wherein the antibody binds to human HLA-G ß2M MHC I complex comprising SEQ ID NO: 25 (see Example 3).

In certain embodiments, an isolated antibody that specifically binds to human HLA-G is provided wherein the antibody binds to human HLA-G ß2M MHC I complex comprising SEQ ID NO: 25, and wherein the antibody inhibits ILT2 binding to monomeric HLA-G ß2M MHC I complex (see e.g Example 4a and 4b).

In certain embodiments, an isolated antibody that specifically binds to human HLA-G is provided wherein the antibody binds to human HLA-G ß2M MHC I complex (comprising SEQ ID NO: 25), and wherein the antibody inhibits ILT2 binding to monomeric HLA-G ß2M MHC I complex by more than 50% (when compared to the binding without antibody) (see e.g Example 4b).

In certain embodiments, an isolated antibody that specifically binds to human HLA-G is provided wherein the antibody binds to human HLA-G ß2M MHC I complex (comprising SEQ ID NO: 25), and wherein the antibody inhibits ILT2 binding to monomeric and/or dimeric and/or trimeric HLA-G ß2M MHC I complex by more than 50% (in one embodiment by more than 70%) (when compared to the binding without antibody) (see e.g Example 4b).

In certain embodiments, an isolated antibody that specifically binds to human HLA-G is provided wherein the antibody binds to human HLA-G ß2M MHC I complex (comprising SEQ ID NO: 25), and wherein the antibody inhibits ILT2 binding to monomeric and/or dimeric and/or trimeric HLA-G ß2M MHC I complex by more than 60% (when compared to the binding without antibody) inhibits ILT4 binding to dimeric and/or trimeric HLA-G ß2M MHC I complex by more than 50% (when compared to the binding without antibody) (see e.g Example 4b).

In certain embodiments, an isolated antibody that specifically binds to human HLA-G is provided wherein the antibody binds to human HLA-G ß2M MHC I complex comprising SEQ ID NO: 25; and wherein the antibody inhibits ILT2 and ILT4 binding to HLA-G ß2M MHC I complex (see Example 4).

In certain embodiments, an isolated antibody that specifically binds to human HLA-G is provided wherein the antibody binds to human HLA-G ß2M MHC I complex (comprising SEQ ID NO: 25), and wherein the antibody inhibits ILT2 binding to (HLA-G on) JEG3 cells (ATCC No. HTB36) (by more than 50% (in one embodiment by more than 80%)) (when compared to the binding without antibody) (see Example 6).

In certain embodiments, an isolated antibody that specifically binds to human HLA-G is provided wherein the antibody binds to (HLA-G on) JEG3 cells (ATCC No. HTB36) (see Example 5), and wherein the antibody inhibits ILT2 binding to HLA-G on JEG3 cells (ATCC No. HTB36) (by more than 50% (in one embodiment by more than 80%)) (when compared to the binding without antibody) (see Example 6).

In certain embodiments the anti-HLA-G antibody described herein does not crossreact with (does not specifically bind to) a modified human HLA-G ß2M MHC I complex comprising SEQ ID NO:26.

In certain embodiments the anti-HLA-G antibody described herein does not crossreact with (does not specifically bind to) a mouse H2Kd ß2M MHC I complex comprising SEQ ID NO:27 and/or does not crossreact with (does not specifically bind to) rat RT1A ß2M MHC I complex comprising SEQ ID NO:29.

In certain embodiments the anti-HLA-G antibody described herein does not crossreact with (does not specifically bind to) human HLA-A2 ß2M MHC I complex comprising SEQ ID NO:21 and SEQ ID NO: 19.

One embodiment of the invention is an isolated antibody that binds to human HLA-G, wherein the antibody comprises A) (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6; or B) (a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.

One embodiment of the invention is an isolated antibody that binds to human HLA-G, wherein the antibody comprises A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14.

One embodiment of the invention is an isolated antibody that binds to human HLA-G, wherein the antibody
A)
i) comprises a VH sequence of SEQ ID NO:7 and a VL sequence of SEQ ID NO:8;
ii) or humanized variant of the VH and VL of the antibody under i);
or B)
i) comprises a VH sequence of SEQ ID NO:15 and a VL sequence of SEQ ID NO:16;
ii) or humanized variant of the VH and VL of the antibody under i);

One embodiment of the invention is the anti-HLA-G antibody as described herein wherein the antibody is characterized independently by the following properties: the anti-HLA-G antibody
a) competes for binding to HLA-G with an anti-HLA-G antibody comprising the VH with the amino acid sequence of SEQ ID NO:7 and VL with the amino acid sequence of SEQ ID NO:8, and/or
b) binds to the same epitope as an anti-HLA-G antibody comprising the VH with the amino acid sequence of SEQ ID NO:7 and VL with the amino acid sequence of SEQ ID NO:8, and/or
c) binds to human HLA-G ß2M MHC I complex comprising SEQ ID NO: 25; and/or
d) does not crossreact with (does not specifically bind to) a modified human HLA-G ß2M MHC I complex comprising SEQ ID NO:26; and/or
e) does not crossreact with (does not specifically bind to) human HLA-A2 ß2M MHC I complex comprising SEQ ID NO:21 and SEQ ID NO: 19; and/or
f) does not crossreact with (does not specifically bind to) a mouse H2Kd ß2M MHC I complex comprising SEQ ID NO:27; and/or
g) does not crossreact with (does not specifically bind to) rat RT1A ß2M MHC I complex comprising SEQ ID NO:29; and/or
h) inhibits ILT2 binding to monomeric HLA-G ß2M MHC I complex (comprising SEQ ID NO: 25); and/or
i) inhibits ILT2 binding to monomeric HLA-G ß2M MHC I complex (comprising SEQ ID NO: 25), by more than 50% (in on embodiment by more than 70%) (when compared to the binding without antibody); and/or j) inhibits ILT2 binding to monomeric and/or dimeric and/or trimeric HLA-G ß2M MHC I complex (comprising SEQ ID NO: 25), by more than 50% (in on embodiment by more than 70%) (when compared to the binding without antibody); and/or k) inhibits ILT2 binding to (HLA-G on) JEG3 cells (ATCC No. HTB36) (by more than 50% (in one embodiment by more than 80%)) (when compared to the binding without antibody) (see Example 6); and/or l) wherein the antibody binds to (HLA-G on) JEG3 cells (ATCC No. HTB36) (see Example 5), and wherein the antibody inhibits ILT2 binding to (HLA-G on) JEG3 cells (ATCC No. HTB36) (by more than 50% (in one embodiment by more than 80%)) (when compared to the binding without antibody) (see Example 6); and/or m) wherein the antibody binds to human HLA-G ß2M MHC I complex (comprising SEQ ID NO: 25), and wherein the antibody inhibits ILT2 binding to monomeric and/or dimeric and/or trimeric HLA-G ß2M MHC I complex by more than 60% (when compared to the binding without antibody) inhibits ILT4 binding to dimeric and/or trimeric HLA-G ß2M MHC I complex by more than 50% (when compared to the binding without antibody) (see e.g Example 4b).

One embodiment of the invention is an isolated antibody that binds to human HLA-G, wherein the antibody comprises A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14;

and wherein the antibody under A) or B) is characterized independently by the following properties: the anti-HLA-G antibody a) binds to human HLA-G ß2M MHC I complex comprising SEQ ID NO: 25; and/or b) does not crossreact with (does not specifically bind to) a modified human HLA-G ß2M MHC I complex comprising SEQ ID NO:26; and/or c) does not crossreact with (does not specifically bind to) human HLA-A2 ß2M MHC I complex comprising SEQ ID NO:21 and SEQ ID NO: 19; and/or d) does not crossreact with (does not specifically bind to) a mouse H2Kd ß2M MHC I complex comprising SEQ ID NO:27; and/or e) does not crossreact with (does not specifically bind to) rat RT1A ß2M MHC I complex comprising SEQ ID NO:29; and/or f) inhibits ILT2 binding to monomeric HLA-G ß2M MHC I complex (comprising SEQ ID NO: 25); and/or g) inhibits ILT2 binding to monomeric HLA-G ß2M MHC I complex (comprising SEQ ID NO: 25), by more than 50% (in on embodiment by more than 70%) (when compared to the binding without antibody); and/or h) inhibits ILT2 binding to monomeric and/or dimeric and/or trimeric HLA-G ß2M MHC I complex (comprising SEQ ID NO: 25), by more than 50% (in on embodiment by more than 70%) (when compared to the binding without antibody); and/or i) inhibits ILT2 binding to HLA-G on JEG3 cells (ATCC No. HTB36) (by more than 50% (in one embodiment by more than 80%)) (when compared to the binding without antibody) (see Example 6); and/or j) wherein the antibody binds to human HLA-G on JEG3 cells (ATCC No. HTB36) (see Example 5), and wherein the antibody inhibits ILT2 binding to HLA-G on JEG3 cells (ATCC No. HTB36) (by more than 50% (in one embodiment by more than 80%)) (when compared to the binding without antibody) (see Example 6); and/or k) wherein the antibody binds to human HLA-G ß2M MHC I complex (comprising SEQ ID NO: 25), and wherein the antibody inhibits ILT2 binding to monomeric and/or dimeric and/or trimeric HLA-G ß2M MHC I complex by more than 60% (when compared to the binding without antibody) inhibits ILT4 binding to dimeric and/or trimeric HLA-G ß2M MHC I complex by more than 50% (when compared to the binding without antibody) (see e.g Example 4b).

In one embodiment of the invention the antibody is of IgG1 isotype. In one embodiment of the invention the antibody is of IgG1 isotype with mutations L234A, L235A and P329G (numbering according to the EU index of Kabat)

In a further aspect, an anti-HLA-G antibody according to any of the above embodiments may incorporate any of the features, singly or in combination, as described in Sections 1-7 below:

1. Antibody Affinity

In certain embodiments, an antibody provided herein has a dissociation constant KD of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one preferred embodiment, KD is measured using surface plasmon resonance assays using a BIACORE®) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$ or ka) and dissociation rates ($k_{off}$ or kd) are calculated using a simple one-to-one Langmuir binding model (BIACORE® Evaluation Software version 3.2) by simultaneously fitting the association and dissociation sensorgrams. The equilibrium dissociation constant KD is calculated as the ratio kd/ka ($k_{off}/k_{on}$) See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci.

USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HLA-G and the other is for any other antigen. In certain embodiments, bispecific antibodies may bind to two different epitopes of HLA-G. Bispecific antibodies may also be used to localize cytotoxic agents to cells which express HLA-G. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, Metal., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to HLA-G as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793, WO2011/117330, WO2012/025525, WO2012/025530, WO2013/026835, WO2013/026831, WO2013/164325, or WO 2013/174873.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In one embodiment the invention such antibody is a IgG1 with mutations L234A and L235A or with mutations L234A, L235A and P329G. In another embodiment or IgG4 with mutations S228P and L235E or S228P, L235E or and P329G (numbering according to EU index of Kabat et al, Kabat et al., Sequences of Proteins of Immunological Interest, 5th Ed. Public Health Service, National Institutes of Health, Bethesda, Md., 1991)

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

d) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-HLA-G antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell, a HEK293 cell or lymphoid cell (e.g., Y0, NS0, Sp20 cell). In one embodiment, a method of making an anti-HLA-G antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HLA-G antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-HLA-G antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with HLA-G-0032 (comprising a VH sequence of SEQ ID NO:7 and a VL sequence of SEQ ID NO:8) for binding to HLA-G. One embodiment of the invention is an antibody which competes for binding to human HLA-G with an anti-HLA-G antibody comprising all 3 HVRs of VH sequence of SEQ ID NO:7 and all 3 HVRs of VL sequence of SEQ ID NO:8. In certain embodiments, such a competing antibody binds to the same epitope (e.g., a linear or a conformational epitope) that is bound by anti-HLA-G antibody HLA-G-0032. In one embodiment an anti-HLA-G antibody is provide which binds to the same epitope on HLA-G as an antibody comprising a VH sequence of SEQ ID NO:7 and a VL sequence of SEQ ID NO:8. In another aspect, competition assays may be used to identify an antibody that competes with HLA-G-0037 (comprising a VH sequence of SEQ ID NO:15 and a VL sequence of SEQ ID NO:16) for binding to HLA-G. One embodiment of the invention is an antibody which competes for binding to human HLA-G with an anti-HLA-G antibody comprising all 3 HVRs of VH sequence of SEQ ID NO:15 and all 3 HVRs of VL sequence of SEQ ID NO:16. In certain embodiments, such a competing antibody binds to the same epitope (e.g., a linear or a conformational epitope) that is bound by anti-HLA-G antibody HLA-G-0037. In one embodiment an anti-HLA-G antibody is provide which binds to the same epitope on HLA-G as an antibody comprising a VH sequence of SEQ ID NO:15 and a VL sequence of SEQ ID NO:16. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996).

In an exemplary competition assay, immobilized HLA-G is incubated in a solution comprising a first labeled antibody that binds to HLA-G (e.g., anti-HLA-G antibody HLA-G-0032 or HLA-G.0037) and a second unlabeled antibody that is being tested for its ability to compete with the first antibody for binding to HLA-G. The second antibody may be present in a hybridoma supernatant. As a control, immobilized HLA-G is incubated in a solution comprising the first labeled antibody but not the second unlabeled antibody. After incubation under conditions permissive for binding of the first antibody to HLA-G, excess unbound antibody is removed, and the amount of label associated with immobilized HLA-G is measured. If the amount of label associated with immobilized HLA-G is substantially reduced in the test sample relative to the control sample, then that indicates that the second antibody is competing with the first antibody for binding to HLA-G. See Harlow, E. and Lane, D., Antibodies: A Laboratory Manual, Chapter 14, Cold Spring Harbor Laboratory, Cold Spring Harbor, N.Y. (1988). For another exemplary competition assay see Example 2 (Epitope mapping ELISA/Binding competition assay).

2. Activity Assays

In one aspect, assays are provided for identifying anti-HLA-G antibodies thereof having biological activity. Biological activity may include, e.g., the ability to enhance the activation and/or proliferation of different immune cells including T-cells. E.g. they enhance secretion of immunomodulating cytokines (e.g. interferon-gamma (IFN-gamma) and/or tumor necrosis factor alpha (TNF alpha)). Other immunomodulating cytokines which are or can be enhance are e.g IL1B, IL6, IL12, Granzyme B etc. binding to different cell types. Antibodies having such biological activity in vivo and/or in vitro are also provided.

In certain embodiments, an antibody of the invention is tested for such biological activity as described e.g. in Examples below.

D. Immunoconjugates (Cancer Only or Modify for Target)

The invention also provides immunoconjugates comprising an anti-HLA-G antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med.

Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-HLA-G antibodies provided herein is useful for detecting the presence of HLA-G in a biological sample. The term "detecting" as used herein encompasses quantitative or qualitative detection. In certain embodiments, a biological sample comprises a cell or tissue, such as immune cell or T cell infiltrates and or tumor cells.

In one embodiment, an anti-HLA-G antibody for use in a method of diagnosis or detection is provided. In a further aspect, a method of detecting the presence of HLA-G in a biological sample is provided. In certain embodiments, the method comprises contacting the biological sample with an anti-HLA-G antibody as described herein under conditions permissive for binding of the anti-HLA-G antibody to HLA-G, and detecting whether a complex is formed between the anti-HLA-G antibody and HLA-G. Such method may be an in vitro or in vivo method. In one embodiment, an anti-HLA-G antibody is used to select subjects eligible for therapy with an anti-HLA-G antibody, e.g. where HLA-G is a biomarker for selection of patients.

In certain embodiments, labeled anti-HLA-G antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-HLA-G antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-HLA-G antibodies (or antigen binding proteins) provided herein may be used in therapeutic methods.

In one aspect, an anti-HLA-G antibody for use as a medicament is provided. In further aspects, an anti-HLA-G antibody or use in treating cancer is provided. In certain embodiments, an anti-HLA-G antibody for use in a method of treatment is provided. In certain embodiments, the invention provides an anti-HLA-G antibody for use in a method of treating an individual having cancer comprising administering to the individual an effective amount of the anti-HLA-G antibody.

In further embodiments, the invention provides an anti-HLA-G antibody for use as immunomodulatory agent/to directly or indirectly induce proliferation, activation e.g. by secretion of immunostimulatory cytokines like TNFalpha (TNFa) and IFNgamma (IFNg) or further recruitment of immune cells. In certain embodiments, the invention provides an anti-HLA-G antibody for use in a method of immunomodulatory agent/to directly or indirectly induce proliferation, activation e.g. by secretion of immunostimulatory cytokines like TNFa and IFNgamma or further recruitment of immune cells in an individual comprising administering to the individual an effective of the anti-HLA-G antibody for immunomodulation/or directly or indirectly induce proliferation, activation e.g. by secretion of immunostimulatory cytokines like TNFa and IFNgamma or further recruitment of immune cells.

In further embodiments, the invention provides an anti-HLA-G antibody for use as immunostimmulatory agent/or stimulating tumor necrosis factor alpha (TNF alpha) secretion. In certain embodiments, the invention provides an anti-HLA-G antibody for use in a method of immunomodulation to directly or indirectly induce proliferation, activation e.g. by secretion of immunostimulatory cytokines like TNFa and IFNg or further recruitment of immune cells in an individual comprising administering to the individual an effective of the anti-HLA-G antibodyimmunomodulation to directly or indirectly induce proliferation, activation e.g. by secretion of immunostimulatory cytokines like TNFa and IFNg or further recruitment of immune cells.

An "individual" according to any of the above embodiments is preferably a human. In a further aspect, the invention provides for the use of an anti-HLA-G antibody in the manufacture or preparation of a medicament. In one embodiment, the medicament is for treatment of cancer. In a further embodiment, the medicament is for use in a method of treating cancer comprising administering to an individual having cancer an effective amount of the medicament. In a further embodiment, the medicament is for inducing cell mediated lysis of cancer cells In a further embodiment, the medicament is for use in a method of inducing cell mediated lysis of cancer cells in an individual suffering from cancer comprising administering to the individual an amount effective of the medicament to induce apoptosis in a cancer cell/or to inhibit cancer cell proliferation. An "individual" according to any of the above embodiments may be a human.

In a further aspect, the invention provides a method for treating cancer. In one embodiment, the method comprises administering to an individual having cancer an effective amount of an anti-HLA-G. An "individual" according to any of the above embodiments may be a human.

In a further aspect, the invention provides a method for inducing cell mediated lysis of cancer cells in an individual suffering from cancer. In one embodiment, the method comprises administering to the individual an effective amount of an anti-HLA-G to induce cell mediated lysis of cancer cells in the individual suffering from cancer. In one embodiment, an "individual" is a human.

In a further aspect, the invention provides pharmaceutical formulations comprising any of the anti-HLA-G antibodies provided herein, e.g., for use in any of the above therapeutic methods. In one embodiment, a pharmaceutical formulation comprises any of the anti-HLA-G antibodies provided herein and a pharmaceutically acceptable carrier.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-HLA-G antibody.

It is understood that any of the above formulations or therapeutic methods may be carried out using an immunoconjugate of the invention in place of or in addition to an anti-HLA-G antibody.

II. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples and figures are provided to aid the understanding of the present invention, the true scope of which is set forth in the appended claims. It is understood that modifications can be made in the procedures set forth without departing from the spirit of the invention.

Description of the Amino Acid Sequences

SEQ ID NO: 1 heavy chain HVR-H1, HLA-G-0032
SEQ ID NO: 2 heavy chain HVR-H2, HLA-G-0032
SEQ ID NO: 3 heavy chain HVR-H3, HLA-G-0032
SEQ ID NO: 4 light chain HVR-L1, HLA-G-0032
SEQ ID NO: 5 light chain HVR-L2, HLA-G-0032
SEQ ID NO: 6 light chain HVR-L3, HLA-G-0032
SEQ ID NO: 7 heavy chain variable domain VH, HLA-G-0032
SEQ ID NO: 8 light chain variable domain VL, HLA-G-0032
SEQ ID NO: 9 heavy chain HVR-H1, HLA-G-0037
SEQ ID NO: 10 heavy chain HVR-H2, HLA-G-0037
SEQ ID NO: 11 heavy chain HVR-H3, HLA-G-0037
SEQ ID NO: 12 light chain HVR-L1, HLA-G-0037
SEQ ID NO: 13 light chain HVR-L2, HLA-G-0037
SEQ ID NO: 14 light chain HVR-L3, HLA-G-0037
SEQ ID NO: 15 heavy chain variable domain VH, HLA-G-0037
SEQ ID NO: 16 light chain variable domain VL, HLA-G-0037
SEQ ID NO: 17: exemplary human HLA-G
SEQ ID NO: 18: exemplary human HLA-G extracellular domain (ECD)
SEQ ID NO: 19: exemplary human ß2M
SEQ ID NO: 20: modified human HLA-G (wherein the HLA-G specific amino acids have been replaced by HLA-A consensus amino acids (=degrafted HLA-G see also FIG. 1) ECD)
SEQ ID NO: 21: exemplary human HLA-A2
SEQ ID NO: 22: exemplary human HLA-A2 ECD
SEQ ID NO: 23: exemplary mouse H2Kd ECD SEQ ID NO: 24: exemplary rat RT1A ECD
SEQ ID NO: 25: exemplary human HLA-G ß2M MHC class I complex
SEQ ID NO: 26: exemplary modified human HLA-G ß2M MHC class I complex (wherein the HLA-G specific amino acids have been replaced by HLA-A consensus amino acids (=degrafted HLA-G) see also FIG. 1)
SEQ ID NO: 27: exemplary mouse H2Kd ß2M MHC class I complex
SEQ ID NO: 28: exemplary human HLA-G/mouse H2Kd ß2M MHC class I complex wherein the positions specific for human HLA-G are grafted onto the mouse H2Kd framework
SEQ ID NO: 29: exemplary rat RT1A ß2M MHC class I complex
SEQ ID NO: 30: exemplary human HLA-G/rat RT1A ß2M MHC class I complex wherein the positions specific for human HLA-G are grafted onto the rat RT framework
SEQ ID NO: 31 linker and his-Tag
SEQ ID NO: 32 peptide
SEQ ID NO: 33 human kappa light chain constant region
SEQ ID NO: 34 human lambda light chain constant region
SEQ ID NO: 35 human heavy chain constant region derived from IgG1
SEQ ID NO: 36 human heavy chain constant region derived from IgG1 with mutations L234A, L235A and P329G
SEQ ID NO: 37 human heavy chain constant region derived from IgG4
SEQ ID NO: 38 heavy chain variable domain VH, HLA-G-0033
SEQ ID NO: 39 light chain variable domain VL, HLA-G-0033

In the following specific embodiments of the invention are listed:

1. An isolated antibody that specifically binds to human HLA-G, wherein the antibody binds to human HLA-G ß2M MHC I complex comprising SEQ ID NO: 25.
2. The antibody according to embodiment 1, wherein the antibody inhibits ILT2 binding to monomeric HLA-G ß2M MHC I complex.
3. The antibody according to embodiment 2, wherein the antibody inhibits ILT2 binding to monomeric HLA-G ß2M MHC I complex by more than 50% (when compared to the binding without antibody).
4. The antibody according to embodiment 2, wherein the antibody inhibits ILT2 binding to monomeric and/or dimeric and/or trimeric HLA-G ß2M MHC I complex by more than 50% (in one embodiment by more than 70%) (when compared to the binding without antibody).
5. The antibody according to any one of embodiments 1 to 4, wherein the antibody inhibits ILT2 binding to (human HLA-G on) JEG3 cells (ATCC No. HTB36) (by more than 50% (in one embodiment by more than 80%) (as measured in a flow cytometry assay (using Fluorescence-activated cell sorting) (FACS assay)) (when compared to the binding without antibody).
6. An isolated antibody that specifically binds to human HLA-G, wherein the antibody binds to (human HLA-G on) JEG3 cells (ATCC No. HTB36), and wherein the antibody inhibits ILT2 binding to (human HLA-G on) on JEG3 cells (ATCC No. HTB36) by more than 50% (in one embodiment by more than 80%)) (as measured in a flow cytometry assay (using Fluorescence-activated cell sorting) (FACS assay) when compared to the binding without antibody.
7. The antibody according to any one of embodiments 1 to 6, wherein the antibody does not crossreact with (does not specifically bind to) a modified human HLA-G ß2M MHC I complex comprising SEQ ID NO:26; and
8. The antibody according to any one of embodiments 1 to 7, wherein the antibody does not crossreact with (does not specifically bind to) a mouse H2Kd ß2M MHC I complex comprising SEQ ID NO:27 and/or does not crossreact with (does not specifically bind to) rat RT1A ß2M MHC I complex comprising SEQ ID NO:29.
9. The antibody according to any one of embodiments 1 to 8, wherein the antibody does not crossreact with (does not specifically bind to) human HLA-A2 ß2M MHC I complex comprising SEQ ID NO:21 and SEQ ID NO: 19.
10. An isolated antibody that binds to human HLA-G, wherein the antibody comprises
A) (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6; or
B) (a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.
11. An isolated antibody that binds to human HLA-G, wherein the antibody comprises
A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or
B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14.
12. An isolated antibody that binds to human HLA-G, wherein the antibody
A)
  i) comprises a VH sequence of SEQ ID NO:7 and a VL sequence of SEQ ID NO:8;
  ii) or humanized variant of the VH and VL of the antibody under i);
or B)
  i) comprises a VH sequence of SEQ ID NO:15 and a VL sequence of SEQ ID NO:16;
  ii) or humanized variant of the VH and VL of the antibody under i).
13. An isolated antibody that binds to human HLA-G, wherein the antibody
  a) binds to the same epitope as an antibody which comprises a VH sequence of SEQ ID NO:7 and a VL sequence of SEQ ID NO:8;

or b) binds to the same epitope as an antibody which comprises a VH sequence of SEQ ID NO:15 and a VL sequence of SEQ ID NO:16;

14. The anti-HLA-G antibody according to any one of embodiments 10 to 13 wherein the antibody is characterized independently by the following properties: the anti-HLA-G antibody
    a) does not crossreact with (does not specifically bind to) a modified human HLA-G ß2M MHC I complex comprising SEQ ID NO:26; and/or
    b) does not crossreact with (does not specifically bind to) human HLA-A2 ß2M MHC I complex comprising SEQ ID NO:21 and SEQ ID NO: 19; and/or
    c) does not crossreact with (does not specifically bind to) a mouse H2Kd ß2M MHC I complex comprising SEQ ID NO:27; and/or
    d) does not crossreact with (does not specifically bind to) rat RT1A ß2M MHC I complex comprising SEQ ID NO:29; and/or
    e) inhibits ILT2 binding to monomeric HLA-G ß2M MHC I complex (comprising SEQ ID NO: 25); and/or
    f) inhibits ILT2 binding to monomeric HLA-G ß2M MHC I complex (comprising SEQ ID NO: 25), by more than 50% (in on embodiment by more than 70%) (when compared to the binding without antibody); and/or
    g) inhibits ILT2 binding to monomeric and/or dimeric and/or trimeric HLA-G ß2M MHC I complex (comprising SEQ ID NO: 25), by more than 50% (in on embodiment by more than 70%) (when compared to the binding without antibody); and/or
    h) inhibits ILT2 binding to (human HLA-G on) JEG3 cells (ATCC No. HTB36) (by more than 50% (in one embodiment by more than 80%)) (when compared to the binding without antibody) (see Example 6); and/or
    i) wherein the antibody binds to (human HLA-G on) JEG3 cells (ATCC No. HTB36) (see Example 5), and wherein the antibody inhibits ILT2 binding to (human HLA-G on) JEG3 cells (ATCC No. HTB36) (by more than 50% (in one embodiment by more than 80%)) (when compared to the binding without antibody) (see Example 6); and/or
    j) wherein the antibody binds to human HLA-G ß2M MHC I complex (comprising SEQ ID NO: 25), and wherein the antibody inhibits ILT2 binding to monomeric and/or dimeric and/or trimeric HLA-G ß2M MHC I complex by more than 60% (when compared to the binding without antibody) inhibits ILT4 binding to dimeric and/or trimeric HLA-G ß2M MHC I complex by more than 50% (when compared to the binding without antibody) (see e.g Example 4b).

15. The antibody according to any one of the preceding embodiments, wherein the antibody is of IgG1 isotype.
16. The antibody according embodiment 15, wherein the antibody is of IgG1 isotype with mutations L234A, L235A and P329G (numbering according to the EU index of Kabat).
17. Isolated nucleic acid encoding the antibody according to any one of the preceding embodiments.
18. A host cell comprising the nucleic acid of embodiment 17.
19. A method of producing an antibody comprising culturing the host cell of embodiment 18 so that the antibody is produced.
20. The method of embodiment 19, further comprising recovering the antibody from the host cell.
21. A pharmaceutical formulation comprising the antibody according any one of embodiments 1 to 16 and a pharmaceutically acceptable carrier.
22. The antibody according any one of embodiments 1 to 16 for use as a medicament.
23. The antibody according any one of embodiments 1 to 16 for use in treating cancer.
24. Use of the antibody according any one of embodiments 1 to 16 in the manufacture of a medicament.
25. The use of embodiment 24, wherein the medicament is for treatment of cancer.
26. A method of treating an individual having cancer comprising administering to the individual an effective amount of the antibody of embodiment 1, 6 or 10 to 13.
27. A method for selecting anti-HLAG antibodies (e.g. according to embodiments 1 to 4) comprising the following steps:
    a) determining the binding of anti-HLAG antibodies to human HLA-G ß2M MHC I complex comprising SEQ ID NO: 25 by a Surface Plasmon Resonance assay;
    b) determining the inhibition of ILT2 binding to monomeric and/or dimeric and/or trimeric HLA-G ß2M MHC I complex by the respective anti-HLAG antibodies; and
    c) selecting anti-HLAG antibodies which inhibit ILT2 binding to monomeric HLA-G ß2M MHC I complex by more than 50% (in one embodiment by more than 80%) (when compared to the binding without antibody), or selecting anti-HLAG antibodies which inhibit ILT2 binding to monomeric and/or dimeric and/or trimeric HLA-G ß2M MHC I complex by more than 50% (in one embodiment by more than 70%) (when compared to the binding without antibody).
28. A method for selecting anti-HLAG antibodies (e.g. according to embodiment 6) comprising the following steps:
    a) determining the binding of anti-HLAG antibodies to JEG3 cells ((ATCC No. HTB36) in a flow cytometry assay (using Fluorescence-activated cell sorting) (FACS assay).
    b) determining the inhibition of ILT2 binding to JEG3 cells ((ATCC No. HTB36) by the respective anti-HLAG antibodies a flow cytometry assay (using Fluorescence-activated cell sorting) (FACS assay); and
    c) selecting anti-HLAG antibodies which bind to JEG3 (ATCC No. HTB36) cells, and which inhibit ILT2 binding to JEG3 cells (ATCC No. HTB36) by more than 50% (in one embodiment by more than 80%) when compared to the binding without antibody.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany)

Description of the Basic/Standard Mammalian Expression Plasmid

For the expression of a desired gene/protein (e.g. full length antibody heavy chain, full length antibody light chain, or an MHC class I molecule, e.g. HLA-G, or an MHC class I molecule fused to peptide and beta-2 microglobulin, e.g. HLA-G fused to HLA-G binding peptide and or beta-2 microglobulin) a transcription unit comprising the following functional elements is used:

- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain or MHC class I molecule), and
- the bovine growth hormone polyadenylation sequence (BGH pA).

Beside the expression unit/cassette including the desired gene to be expressed the basic/standard mammalian expression plasmid contains

- an origin of replication from the vector pUC18 which allows replication of this plasmid in *E. coli*, and
- a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of HLA-G Chimeric Molecules for Screening and Counterscreening

Due to high homology (>98%) with other MHC I molecules, immunisation with HLA-G molecules results in generation of polyclonal sera, composed of a mixture of MHC-I crossreactive antibodies as well as truly HLA-G specific antibodies.

So far no tools have been provided to select truly HLA-G specific antibodies without crossreactivity to other human MHC-I (e.g. HLA-A), and to further select those with receptor blocking function.

We identified unique HLA-G positions in combination to positions necessary for structural conformity and receptor interaction (ILT2/4 and KIR2DL4.)

Unique and proximal positions of human HLA-G were then "grafted" on MHC class I complex molecules from different rodent species (such as rat RT1A and mouse H2kd) to generate "chimeric" immunogen/screening antigens.

Antibodies generated were subjected to stringent screening for binding/specificity, (and no binding/specificity to counterantigens, respectively)

Screening Antigens:
  rec. HLA-G expressed as human HLA-G ß2M MHC complex comprising SEQ ID NO: 25
  HLA-G specific sequences grafted onto rat RT-1 and mouse H2kd (SEQ ID NO: 28: human HLA-G/mouse H2Kd ß2M MHC class I complex wherein the positions specific for human HLA-G are grafted onto the mouse H2Kd framework and SEQ ID NO: 30: human HLA-G/rat RT1A ß2M MHC class I complex wherein the positions specific for human HLA-G are grafted onto the rat RT1A framework)
  Natural HLA-G MHC class I complex expressing cells (e.g. Jeg3 cells), or human HLA-G transfected cell lines SKOV3 HLA-G+ and PA-TU-8902 HLA-G+

Screening Counter Antigens:
  Counter antigens (MHC class I complexes) with other HLA-A sequences (HLA-A2 and HLA-G$^{degrafted\ with\ HLA-A\ consensus\ sequence}$) combined with different peptides) (see e.g. SEQ ID NO 22 (HLA-A2) and SEQ ID NO: 26 HLA-A consensus sequence on HLA-G framework)
  Counter antigens (MHC class I complexes) from other species such as rat RT-1 and mouse H2kd (SEQ ID NO: 27 and SEQ ID NO: 29)
  Unmodified tumor cell lines SKOV3 and PA-TU-8902, which are characterized by absence of HLA-G expression.

Design of Chimeric HLA-G Antigens for Use in Immunization and Screening for the Generation of HLA-Specific Antibodies (See FIG. 1):

Design of a chimeric rat MHC I molecule (RT1-A) carrying HLA-G unique positions (SEQ ID NO: 30) for use in immunization of wildtype (wt) and transgenic rats, or rabbits and mice etc., and/or for use screening assays:

HLA-G unique positions were identified by the alignment of 2579 HLA-A, 3283 HLA-B, 2133 HLA-C, 15 HLA-E, 22 HLA-F, and 50 HLA-G sequences from IMGT (as available on 6. Feb. 2014). Those residues of HLA-G that occur in less than 1% (mostly ~0%) of the sequences of any of the 3 sequence sets HLA-A, HLA-B, and a combined set of HLA-C+HLA-E+HLA-F are called HLA-G unique positions.

The 4 core HLA-G unique positions (2 in alpha-1 and 2 in alpha-3) show no polymorphism in the set of HLA-G sequences and none of the other HLA genes contain the HLA-G specific residues at these positions (except 1×HLA-A for M100, 1×HLA-B for Q103, and 1×HLA-C for Q103).

The crystal structure of rat RT1-A (Rudolph, M. G. et al. J. Mol. Biol. 324: 975-990 (2002); PDB code: 1KJM) was superimposed on the crystal structure of human HLA-G (Clements, C. S. et al. PROC. NATL. ACAD. SCI. USA 102: 3360-3365 (2005); PDB code: 1YDP). The overall structure of the alpha-chain and the associated beta-2-microglobulin is conserved.

HLA-G unique positions were identified in the RT1-A structure by comparison of the sequence and structural alignments. In a first step, unique HLA-G positions were identified that are exposed on the molecular surface of HLA-G and RT1-A and thus accessible for an antibody. Unique positions that are buried within the protein fold were excluded for engineering. In a second step, structurally proximal residues were identified, that also need to be exchanged to make the corresponding region "HLA-G-like", i.e. to generate real HLA-G epitopes containing the unique positions rather than generating HLA-G/rat RT1-A chimeric epitopes that would be artificial. All the positions that were thus selected for mutation were analyzed for structural fit of the respective residue from HLA-G to avoid possible local disturbances of the molecular structure upon mutation.

A chimeric mouse MHC I molecule (H2Kd) carrying HLA-G unique positions (SEQ ID NO: 28) for use in immunization and/or for use screening assays was generated analogously.

Design of HLA-A Based Counter Antigens by "De-Grafting" of HLA-G Unique Positions Towards a HLA-A Consensus Sequence for Use as a Counter-Antigen in Screening (SEQ ID NO:26)

Unique positions derived from the multiple sequence alignment were analyzed in a crystal structure of human HLA-G (PDB code: 1YDP). First, positions that are not exposed on the HLA-G surface and are thus not accessible for an antibody were excluded for engineering. Second, the surface exposed residues were analyzed for feasibility of amino acid exchange (i.e. exclusion of possible local disturbances of the molecular structure upon mutation of the relevant position). In total, 14 positions were validated for exchange. The amino acids in the validated positions were mutated towards a HLA-A consensus sequence derived from a multiple sequence alignment of 2579 HLA-A sequences downloaded from IMGT (as available on 6. Feb. 2014).

Generation of Expression Plasmids for Soluble Classical and Non-Classical MHC Class I Molecules The recombinant MHC class I genes encode N-terminally extended fusion molecules consisting of a peptide know to be bound by the respective MHC class I molecule, beta-2 microglobulin, and the respective MHC class I molecule.

The expression plasmids for the transient expression of soluble MHC class I molecules comprised besides the soluble MHC class I molecule expression cassette an origin of replication from the vector pUC18, which allows replication of this plasmid in E. coli, and a beta-lactamase gene which confers ampicillin resistance in E. coli.

The transcription unit of the soluble MHC class I molecule comprised the following functional elements:
the immediate early enhancer and promoter from the human cytomegalovirus (P-CMV) including intron A,
a human heavy chain immunoglobulin 5'-untranslated region (5'UTR),
a murine immunoglobulin heavy chain signal sequence,
an N-terminally truncated S. aureus sortase A encoding nucleic acid, and
the bovine growth hormone polyadenylation sequence (BGH pA).

The amino acid sequences of the mature soluble MHC class I molecules derived from the various species are:
SEQ ID NO: 25: exemplary human HLA-G ß2M MHC class I complex
SEQ ID NO: 26: exemplary modified human HLA-G ß2M MHC class I complex (wherein the HLA-G specific amino acids have been replaced by HLA consensus amino acids (=degrafted HLA-G see also FIG. 1)
SEQ ID NO: 27: exemplary mouse H2Kd ß2M MHC class I complex
SEQ ID NO: 28: exemplary human HLA-G/mouse H2Kd ß2M MHC complex wherein the positions specific for human HLA-G are grafted onto the mouse H2Kd framework
SEQ ID NO: 29: exemplary rat RT1A ß2M MHC class I complex
SEQ ID NO: 30: exemplary human HLA-G/rat RT1A ß2M MHC complex wherein the positions specific for human HLA-G are grafted onto the rat RT1A framework For the exemplary HLA-A2 ß2M MHC class I complex used in screening the following components were used and the complex was expressed in E. coli and purified.
MHCI complex HLA-A2/b2M (SEQ ID NOs 22 and 19) (both with an additional N-terminal methionine)+VLD-FAPPGA peptide (SEQ ID NO: 32)+linker and his-Tag (SEQ ID NO: 31)

Example 2

Immunization Campaigns a. Chimeric Proteins (for Tolerance Against Unspecific MHC-I/HLA and Direction to Unique HLA-G Positions)

Balb/C mice obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2531-19-10 and 55.2-1-54-2532-51-11) and performed according to the German Animal Welfare Act and the Directive 2010/63 of the European Parliament and Council.

Balb/C mice (n=5), 6-8 week old, received five rounds of immunization with a chimeric H2Kd/HLA-G molecule (SEQ ID NO: 28 ("HLA-G-0006")) over a course of 4 weeks. Before each immunization, mice were anesthetized with a gas mixture of oxygen and isoflurane. For the first immunization, 15 µg protein dissolved in 20 mM His/HisCl, 140 mM NaCl, pH 6.0, were mixed with an equal volume of CFA (BD Difco, #263810) and administered subcutaneously (s.c.) to six sites proximal to draining lymph nodes, along the back of the mice, with two sites at the nape of the neck and two sites bilaterally to the groin and calf. Another 15 µg of protein emulsified in RIBI adjuvant (Sigma-Aldrich, #S6322) was administered to six juxtaposed sites along the abdomen, with two sites each bilaterally to the axilla, groin, and thigh. Descending antigen doses of booster immunizations were given on days 7 (10 µg), 14 (5 µg), 21 (5 µg), and 28 (5 µg) in a similar fashion except RIBI adjuvant was used throughout, and only along the abdomen. Three days after the final immunization, mice were euthanized and the bilateral popliteal, superficial inguinal, axillary, and branchial lymph nodes were isolated aseptically and prepared for hybridoma generation. Serum was tested for recombinant human HLA-G and immunogen-specific total IgG antibody production by ELISA after the third and fifth immunization.

Another set of Balb/C mice (n=5), 6-8 week old, received three immunizations with the chimeric H2Kd/HLA-G molecule (HLA-G-0006) over a course of 3 months. For the first immunization, 100 µg protein dissolved in 20 mM His/HisCl, 140 mM NaCl, pH 6.0, were mixed with an equal volume of CFA (BD Difco, #263810) and administered intraperitoneally (i.p.). Booster immunizations were given on days 28 and 56 in a similar fashion, except that incompletes Freund's adjuvant (IFA from BD Difco, #DIFC263910) was used. Four to five weeks after the final immunization, mice received approximately 25 µg of the immunogen intravenously (i.v.) in sterile PBS and 72 h later, spleens were aseptically harvested and prepared for hybridoma generation. Serum was tested for recombinant human HLA-G (SEQ ID NO: 25 ("HLA-G-0003")), and immunogen-specific chimeric H2Kd/HLA-G molecule (SEQ ID NO: 28 ("HLA-G-0006")) and counterscreened with"degrafted" human HLA-G with consensus HLA-A specific positions (SEQ ID NO: 26 ("HLA-G-0007")) and murine H2kd protein (SEQ ID NO: 27 "HLA-G-0009")) total IgG antibody production by ELISA after the third immunization.

b. wt HLA-G Protein

CD rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2532-51-11) and performed according to the German Animal Welfare Act and the Directive 2010/63 of the European Parliament and Council.

CD rats (n=4), 6-8 week old, received four immunizations with recombinant human HLA-G protein (SEQ ID NO: 25 ("HLA-G-0003")) over a course of 4 months. For the first immunization, 100 µg protein dissolved in 20 mM His/HisCl, 140 mM NaCl, pH 6.0, were mixed with an equal volume of CFA (BD Difco, #263810) and administered intraperitoneally. Booster immunizations were given on days 28, 56 and 84 in a similar fashion, except that incompletes Freund's adjuvant (IFA from BD Difco, #DIFC263910) was used throughout. Three to four weeks after the final immunization, rats received approximately 75 µg of the immunogen i.v. in sterile PBS; and 72 h later, spleens were aseptically harvested and prepared for hybridoma generation. Serum was tested for recombinant HLA-G (SEQ ID NO: 25 ("HLA-G-0003")) -specific IgG1, IgG1a, IgG2b and IgG2c antibody production by ELISA after the third and fourth immunization and counterscreened with "degrafted" human HLA-G with consensus HLA-A specific positions (SEQ ID NO: 26 ("HLA-G-0007")).

c. JEG3 Cells (ATCC No. HTB36) (Naturally Expressing HLA-G)

CD rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number AZ. 55.2-1-54- 2531-83-13) and performed according to the German Animal Welfare Act and the Directive 2010/63 of the European Parliament and Council.

Two groups of CD rats (n=2), 6-8 week old, received either five (group A) or seven (group B) immunizations using JEG-3 cells (ATCC HTB36) over a course of five (A) to seven (B) months, respectively. For the first immunization, $1\times10^7$ cells dissolved in sterile PBS, were mixed with an equal volume of CFA (BD Difco, #263810) and administered intraperitoneally. Booster immunizations were given to A and B on days 28, 56, 84, 112, 140 (B only) and 168 (B only) in a similar fashion, except that incompletes Freund's adjuvant (IFA from BD Difco, #DIFC263910) was used throughout. Three weeks after the final immunization, rats received 100 µg of recombinant human HLA-G protein (SEQ ID NO: 25 ("HLA-G-0003")) i.v. in sterile PBS; and 72 h later, spleens were aseptically harvested and prepared for hybridoma generation. Serum was tested for for recombinant HLA-G (SEQ ID NO: 25 ("HLA-G-0003")) -specific IgG1, IgG1a, IgG2b and IgG2c antibody production-specific IgG1, IgG2a, IgG2b and IgG2c antibody production by ELISA after the third, fifth and seventh immunization, respectively and counterscreened with "degrafted" human HLA-G with consensus HLA-A specific positions (SEQ ID NO: 26 ("HLA-G-0007")).

d. JEG3/DNA IMS (for Boosting Effect)

CD rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number AZ. 55.2-1-54- 2531-83-13) and performed according to the German Animal Welfare Act and the Directive 2010/63 of the European Parliament and Council.

CD rats (n=5), 6-8 week old, received plasmid DNA and cell-based immunizations in an alternating regime over a course of three months. The plasmid DNA HLA-G-0030 (p17747) encoding for human HLA-G as a single chain molecule as well as the naturally HLA-G expressing JEG-3 cells (ATCC HTB36) were used for this purpose, respectively.

For the first immunization, animals were isoflurane-anesthetized and intradermally (i.d.) immunized with 100 µg plasmid DNA in sterile H2O applied to one spot at the shaved back, proximal to the animal's tail. After i.d. application, the spot was electroporated using following parameters on an ECM 830 electroporation system (BTX Harvard Apparatus): two times 1000 V/cm for 0.1 ms each, separated by an interval of 125 ms, followed by four times 287.5 V/cm for 10 ms, separated also by intervals of 125 ms. For the second immunization on day 14, animals received $1\times10^7$ cells dissolved in sterile PBS, that were mixed with an equal volume of CFA (BD Difco, #263810) and, after generation of a stable emulsion, administered intraperitoneally. Booster immunizations were given on days 28 (DNA), 42 (cells), 56 (DNA), 70 (cells) in a similar fashion, except that incompletes Freund's adjuvant (IFA from BD Difco, #DIFC263910) was used for cell immunizations throughout. Four weeks after the final immunization, rats received 100 µg of soluble recombinant human HLA-G MHC class I protein (SEQ ID NO: 25 ("HLA-G-0003")) i.v. in sterile PBS; and 72 h later, spleens were aseptically harvested and prepared for hybridoma generation. Serum was tested for soluble recombinant human HLA-G MHC class I protein (SEQ ID NO: 25 ("HLA-G-0003"))-specific IgG1, IgG2a, IgG2b and IgG2c antibody production by ELISA after the third, fifth and sixth immunization, respectively and counterscreened with "degrafted" human HLA-G with consensus HLA-A specific positions (SEQ ID NO: 26 ("HLA-G-0007")).

In all immunization strategies a highly polyreactive humoral immune response was induced, recognizing HLA-G, as well as proteins used for counterscreening (e.g. recombinant "degrafted" human HLA-G, chimeric H2Kd/HLA-G molecule or related human HLA-A2 molecules) as analyzed in an ELISA format using polyclonal sera from immunized animals (no data shown)

Binding properties of the obtained anti-HLA-G specific antibodies and biological activities were determined as described in the following Examples and compared to known reference antibodies Example 3

A) Binding of Anti HLA-G Antibodies to Soluble Human HLA-G, Soluble Degrafted Human HLA-G with HLA-A Specific Sequence, Human HLA-A2, and/Rat Mouse H2-Kd Antibodies obtained from immunisation were screened for their binding properties to human, rat and mouse HLA-G, chimeric, degrafted HLA-G and HLA-A. The respective assays are described below. For the testing of human HLA-G either monomeric, as well as dimeric and trimeric forms were used (see preparation below)

Dimerization/Trimerization of Human HLA-G MHC Class I Protein

Supernatant containing monomeric His tagged soluble human HLA-G MHC class I protein (SEQ ID NO: 23) was loaded on to a HisTrap HP column (GE Healthcare #17-

5248-02) with 5 ml Ni-Sepharose at the flow rate of 0.2 ml/min overnight at room temperature using an AKTA-FPLC. Column was then washed with 2% DPBS containing 0.5M Imidazole (Merck #8.14223.025) until baseline was reached. Column was then equilibrated with 10 mM DTT in 2% DPBS containing 0.5M Imidazole and incubated for 30 min at room temperature. DTT was washed out from the column with PBS/10 mM Imidazole and the protein was eluted at a gradient of 2-100% DPBS with 0.5 mM Imidazole. After concentrating the eluate using Amicon-Ultra 15 M/Ultracel 10K, the protein was incubated for 24 hours at room temperature followed by 48 hours at 4° C. to allow dimer/multimerization. Separation of the dimers and trimers was then performed using SEC in Superdex 200 HiLoad 16/60 (GE Healthcare #17-5175-01) and washed with 0.5M NaOH overnight. The column was equilibrated with PBS followed by saturation with 10 mg/ml BSA. The dimers (fraction A9) and the trimers (fraction A8) were then collected, aliquoted and stored at −80° C. till further use.

Human wt HLA-G Binding ELISA

Streptavidin coated plates (Nunc, MicroCoat #11974998001) were coated with 25 µl/well biotinylated human wt HLA-G at a concentration of 250 ng/ml and incubated at 4° C. overnight. After washing (3×90 µl/well with PBST-buffer) 25 µl anti-HLA-G samples (1:3 dilution in OSEP buffer) or reference antibody (G233, Thermo/Pierce #MA1-19449, 500 ng/ml) were added and incubated 1 h at RT. After washing (3×90 µl/well with PBST-buffer) 25 µl/well goat-anti-mouse H+L-POD (Biorad #170-6561, 1:2000 in OSEP) or donkey-anti-rabbit IgG POD (GE #NA9340V, 1:5000 in OSE) was added and incubated at RT for 1 h on shaker. For detection of rat IgGs a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan Safire 2 instrument at 370/492 nm.

Human Degrafted HLA-G with HLA-A Specific Sequences Binding ELISA

Streptavidin coated plates (Nunc, MicroCoat #11974998001) were coated with 25 µl/well biotinylated human degrafted HLA-G at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan Safire 2 instrument at 370/492 nm.

Rat MHC I (RT1-A) Binding ELISA

Streptavidin coated plates (Nunc, MicroCoat #11974998001) were coated with 25 µl/well biotinylated rat MHC I (RT1-A) at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan Safire 2 instrument at 370/492 nm.

HLA-A2 Binding ELISA

Streptavidin coated plates (Nunc, MicroCoat #11974998001) were coated with 25 µl/well biotinylated human HLA-A2 at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan Safire 2 instrument at 370/492 nm.

Binding Kinetics of Anti-HLA-G Antibodies

Binding kinetics of anti-HLA-G antibodies to human HLA-G, human HLA-G degrafted and human HLA-A2 were investigated by surface plasmon resonance using a BIACORE T200 instrument (GE Healthcare). All experiments were performed at 25° C. using PBS Buffer (pH 7.4+0.05% Tween20) as running buffer and PBS Buffer (+0.1% BSA) as dilution buffer. Anti-human Fc (JIR009-005-098, Jackson) or anti-rat Fc (JIR112-005-071, Jackson) or anti-Mouse Fc (JIR115-005-071, Jackson) antibodies were immobilized on a Series S CM5 Sensor Chip (GE Healthcare) at pH 5.0 by using an amine coupling kit supplied by GE Healthcare. Anti-HLA-G antibodies were captured on the surface leading to a capturing response of 50-200 RU. HLA-G molecules were injected for 180 s at 30 µl/min with concentrations from 2.5 up to 800 nM (2×1:2 and 4×1:3 dilution series) onto the surface (association phase). The dissociation phase was monitored for 300-600 sec by washing with running buffer. The surface was regenerated by injecting H3PO4 (0.85%) for 60+30 seconds for anti-human Fc capturing antibodies, glycine pH1.5 for 60 seconds and glycine pH2.0 for 60 seconds for anti-rat Fc capturing antibodies, H3PO4 (0.85%) for 80+60 seconds for anti-mouse Fc capturing antibodies. Bulk refractive index differences were corrected by subtracting the response obtained from a mock surface. Blank injections were subtracted (double referencing). The derived curves were fitted to a 1:1 Langmuir binding model using the BIAevaluation software.

Cross-Blocking of Anti-HLA-G Antibodies

Cross-blocking experiments of anti-HLA-G antibodies binding to human HLA-G were investigated by surface plasmon resonance using a BIACORE T200 or B4000 instrument (GE Healthcare). All experiments were performed at 25° C. using PBS Buffer (pH 7.4+0.05% Tween20) as running buffer.

Anti-human Fab (GE-Healthcare, 28-9583-25) antibodies were immobilized on a Series S CM5 Sensor Chip (GE Healthcare) according to the protocol of the provider, to capture antibodies from OMT rats that contain a human Ck Domain. Anti-HLA-G antibodies were captured for 70s at a concentration of 15 Wt HLA-G was injected (30 µl/min) at a concentration of 500 or 1000 nM for 60 seconds. Wt rat-antibody was then injected for 90 seconds at a concentration of 30 µg/ml. The dissociation phase was monitored for 60 or 240 sec by washing with running buffer. The surface was regenerated by injecting Glycine pH 1.5 for 60 seconds and an additional stabilization period of 90 sec.

In another assay setup, Anti-human Fab (GE-Healthcare, 28-9583-25) antibodies were immobilized on a Series S CM5 Sensor Chip (GE Healthcare) according to the protocol of the provider, to capture antibodies from OMT rats that contain a human Ck Domain. Anti-HLA-G antibodies were captured for 90 s at a concentration of 30 µg/ml. Unoccupied binding sites on the capture antibodies were blocked by 4×120 sec. injection of human IgG (JIR009-000-003) at a concentration of 500 µg/ml and a flow rate of 30 µl/min. Wt HLA-G was injected (30 µl/min) at a concentration of 500 nM for 90 seconds. The second antibody from OMT rats (human Ck Domain) was then injected for 90 seconds at a concentration of 30 µg/ml. The dissociation phase was monitored for 240 sec by washing with running buffer. The surface was regenerated by injecting Glycine pH 1.5 for 60 seconds and an additional a stabilization period of 90 sec.

TABLE

Binding of HLA-G antibodies to recombinant soluble HLA-G MHC class 1 complex, in its monomeric, dimeric and trimeric form (ELISA)

| antibody | HLA-G Monomer EC50 [nM] | HLA-G Dimer EC50 [nM] | HLA-G Trimer EC50 [nM] |
|---|---|---|---|
| HLA-G-0032 | 3.59 | 1.36 | 1.76 |
| HLA-G-0033 | 4.94 | 1.98 | 1.54 |
| HLA-G-0036 | 6.33 | 4.74 | 5.66 |
| HLA-G-0037 | 4.95 | 2.01 | 2.50 |

The above table summarizes the binding of different rat anti-human HLA-G monoclonal antibodies, derived from wt protein IMS. Shown are the relative EC50 values [ng/ml] of the respective binding to rec. wt monomeric, dimeric and trimeric HLA-G proteins as assessed by ELISA. The ELISA was set up by coating the biotinylated wt HLA-G antigen to strepdavidin plates. After incubation and washing steps, the respective antibodies were bound in a concentration range from 10-0 µg in 1:2 dilution steps. Detection of bound antibodies was carried out by anti-Fc-antibody-POD conjugates. EC50 values were determined from the resulting binding curves at the antibody concentrations generating the half-maximal signal. In case of the non-biotinylated HLA-G dimer and trimer antigens, immobilization was carried out by random coating on assay plates.

Binding affinities for HLA-G antibodies to recombinant HLA-G (SEQ ID NO:25) and control modified human HLA-G ß2M MHC class I complex (wherein the HLA-G specific amino acids have been replaced by HLA-A consensus amino acids (=degrafted HLA-G SEQ ID NO: 26:) ("-" indicates no detectable binding)

| Antibody | wt HLA-G (SEQ ID NO: 25) (monomer) | | | | HLA-A consensus on HLA-G degraft (SEQ ID NO: 26) | | | |
|---|---|---|---|---|---|---|---|---|
| | ka (1/Ms) | kd (1/s) | t½ (min) | KD (M) | ka (1/Ms) | kd (1/s) | t½ (min) | KD (M) |
| HLA-G-0032 | 5.12E+04 | 7.60E−04 | 15 | 1.49E−08 | — | — | — | — |
| HLA-G-0033 | 5.23E+04 | 1.65E−03 | 7 | 3.15E−08 | 9.54E+06 | 3.45E−02 | 0.3 | 3.62E−09 |
| HLA-G-0036 | 5.60E+04 | 1.95E−02 | 1 | 3.48E−07 | — | — | — | — |
| HLA-G-0037 | 1.31E+05 | 8.82E−04 | 13 | 6.75E−09 | 5.47E+04 | 1.16E−01 | 0.1 | 2.12E−06 |

The above table summarizes the antibody affinities and t1/2 values against wt and degrafted HLA-G as assessed by Surface plasmon resonance (Biacore) analysis. Binding kinetics of anti-HLA-G antibodies to human HLA-G, human HLA-G degrafted and human HLA-A2 were investigated by surface plasmon resonance using a BIACORE T200 instrument (GE Healthcare). All experiments were performed at 25° C. using PBS Buffer (pH 7.4+0.05% Tween20) as running buffer and PBS Buffer (+0.1% BSA) as dilution buffer. Anti-human Fc (JIR009-005-098, Jackson) or anti-rat Fc (JIR112-005-071, Jackson) or anti-Mouse Fc (JIR115-005-071, Jackson) antibodies were immobilized on a Series S CM5 Sensor Chip (GE Healthcare) at pH 5.0 by using an amine coupling kit supplied by GE Healthcare. Anti-HLA-G antibodies were captured on the surface leading to a capturing response of 50-200 RU. HLA-G molecules were injected for 180 s at 30 µl/min with concentrations from 2.5 up to 800 nM (2×1:2 and 4×1:3 dilution series) onto the surface (association phase). The dissociation phase was monitored for 300-600 sec by washing with running buffer. The surface was regenerated by injecting H3PO4 (0.85%) for 60+30 seconds for anti-human Fc capturing antibodies, glycine pH1.5 for 60 seconds and glycine pH2.0 for 60 seconds for anti-rat Fc capturing antibodies, H3PO4 (0.85%) for 80+60 seconds for anti-mouse Fc capturing antibodies. Bulk refractive index differences were corrected by subtracting the response obtained from a mock surface. Blank injections were subtracted (double referencing). The derived curves were fitted to a 1:1 Langmuir binding model using the BIAevaluation software (- in the table above indicates that no binding could be detected).

Figure 3A:
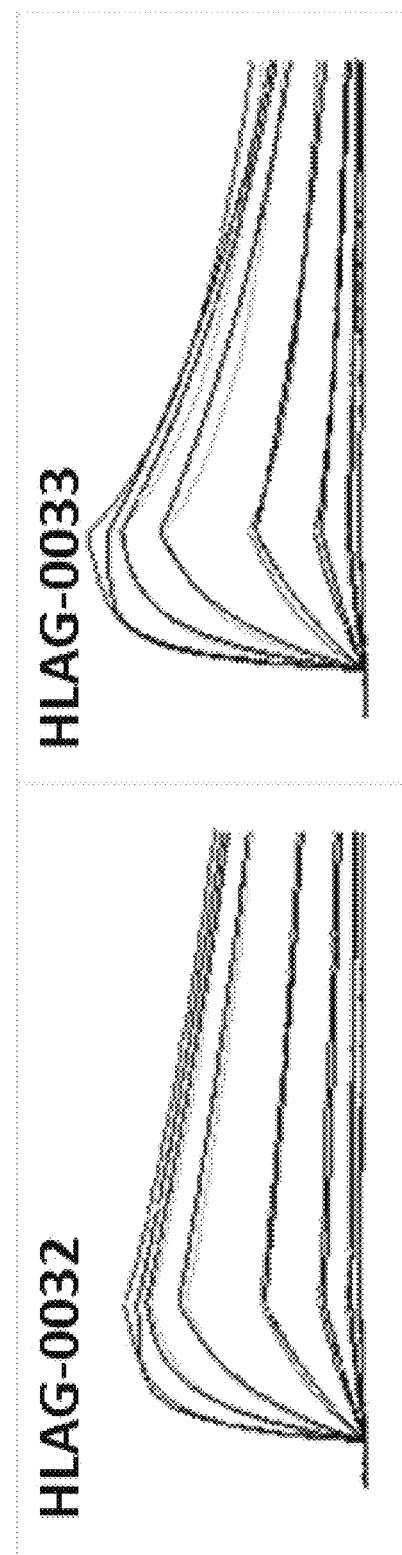
FIG. 3A and FIG. 3B:
The SPR sensorgrams for binding of HLA-G antibodies HLA-G-0032—HLA-G-0037 to recombinant HLA-G (SEQ ID NO: 25) and control modified human HLA-G ß2M MHC class I complex (wherein the HLA-G specific amino acids have been replaced by HLA-A consensus amino acids (=degrafted HLA-G SEQ ID NO: 26)
Figure 3B:
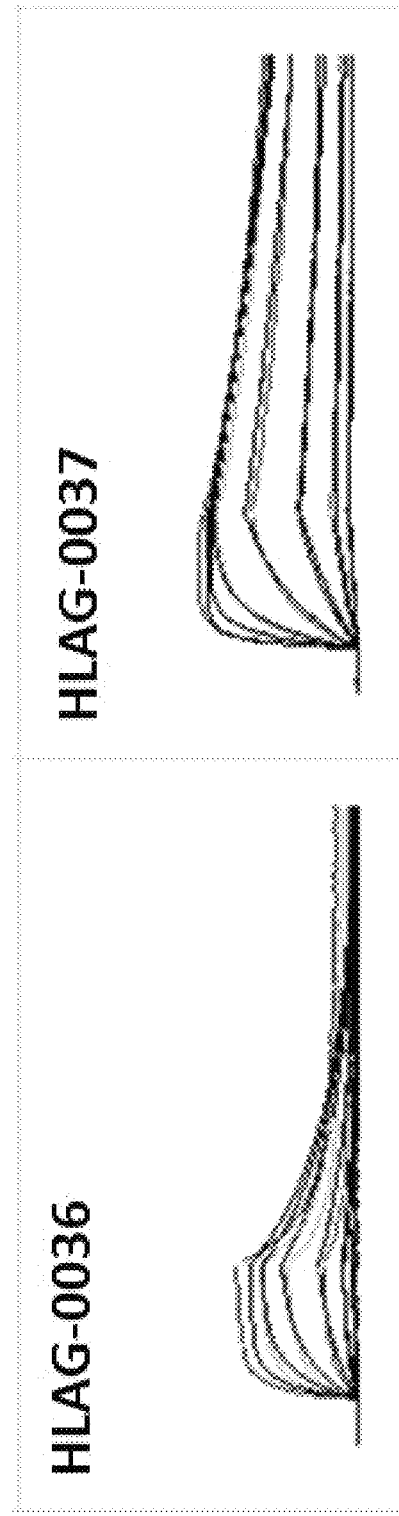
Figure 4A:
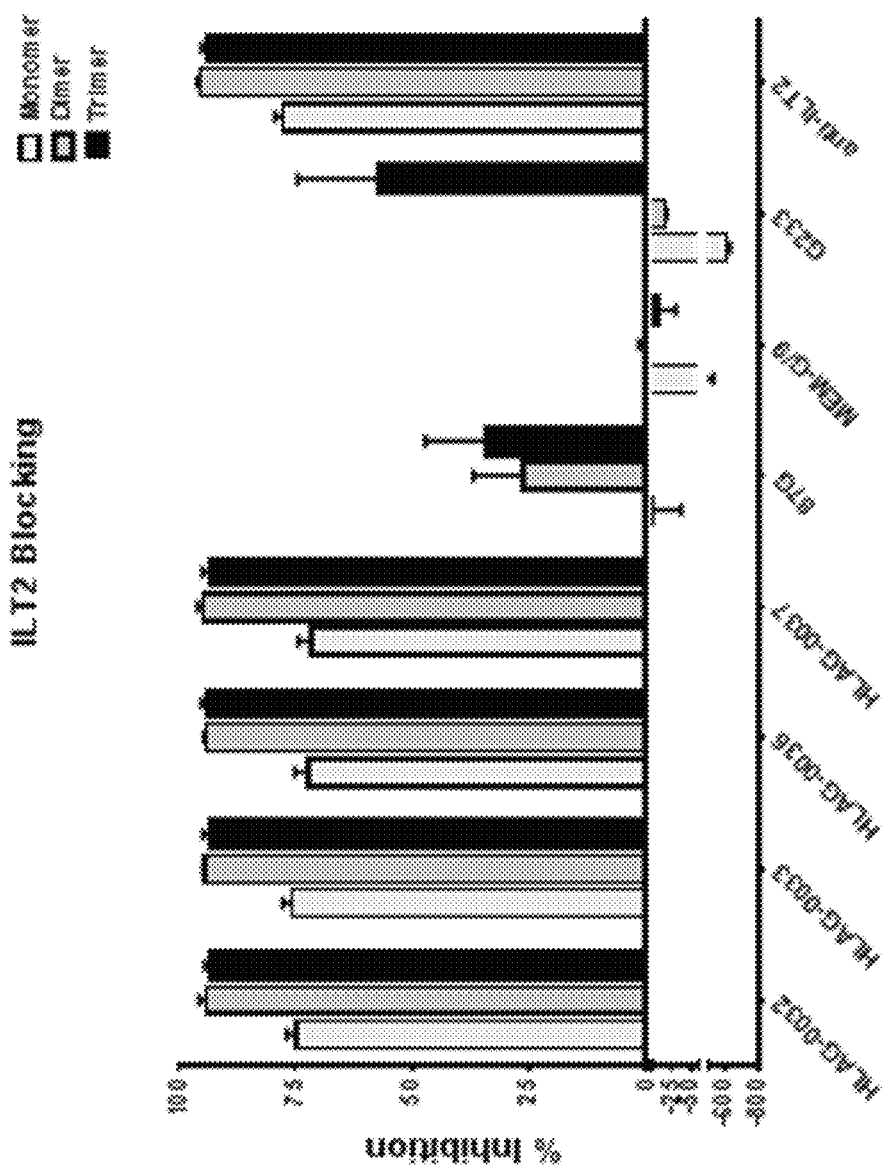
FIG. 4A and FIG. 4B:
HLA-G antibodies which inhibit (or stimulate) HLA-G interaction/binding with ILT2 and ILT4.
Figure 4B:
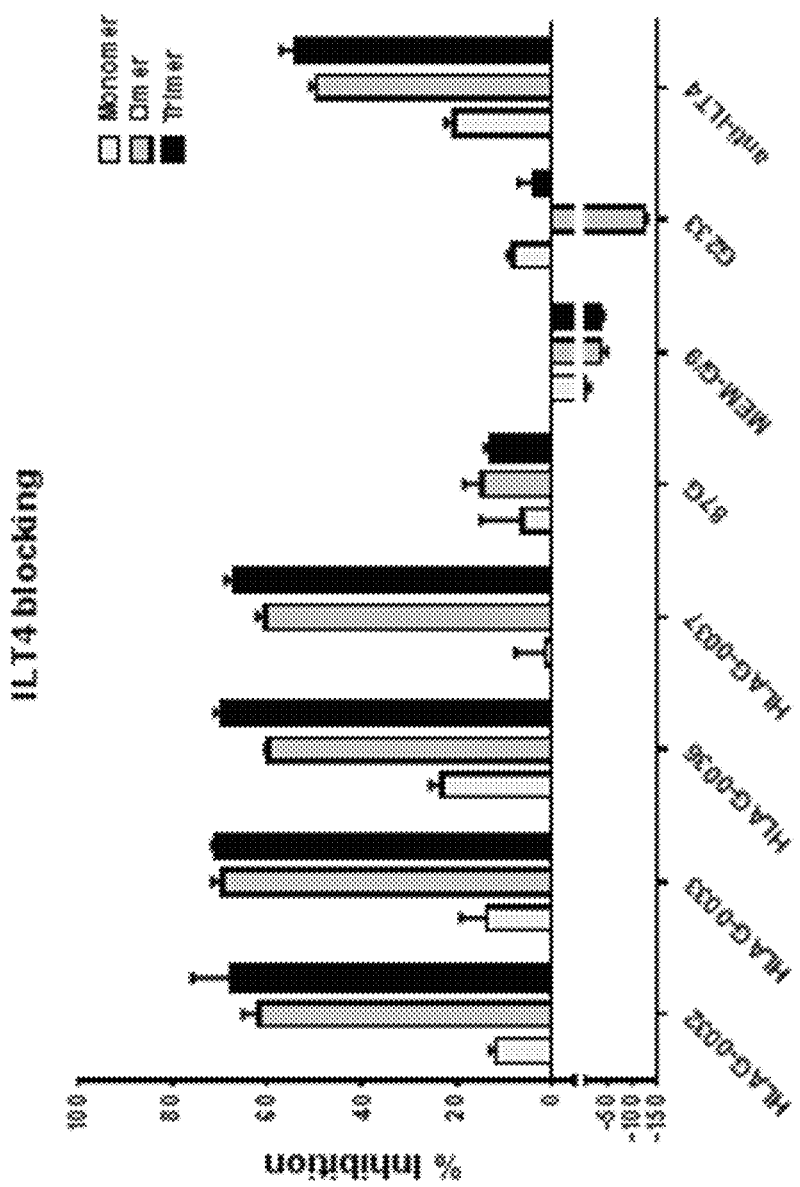
Figure 5B:
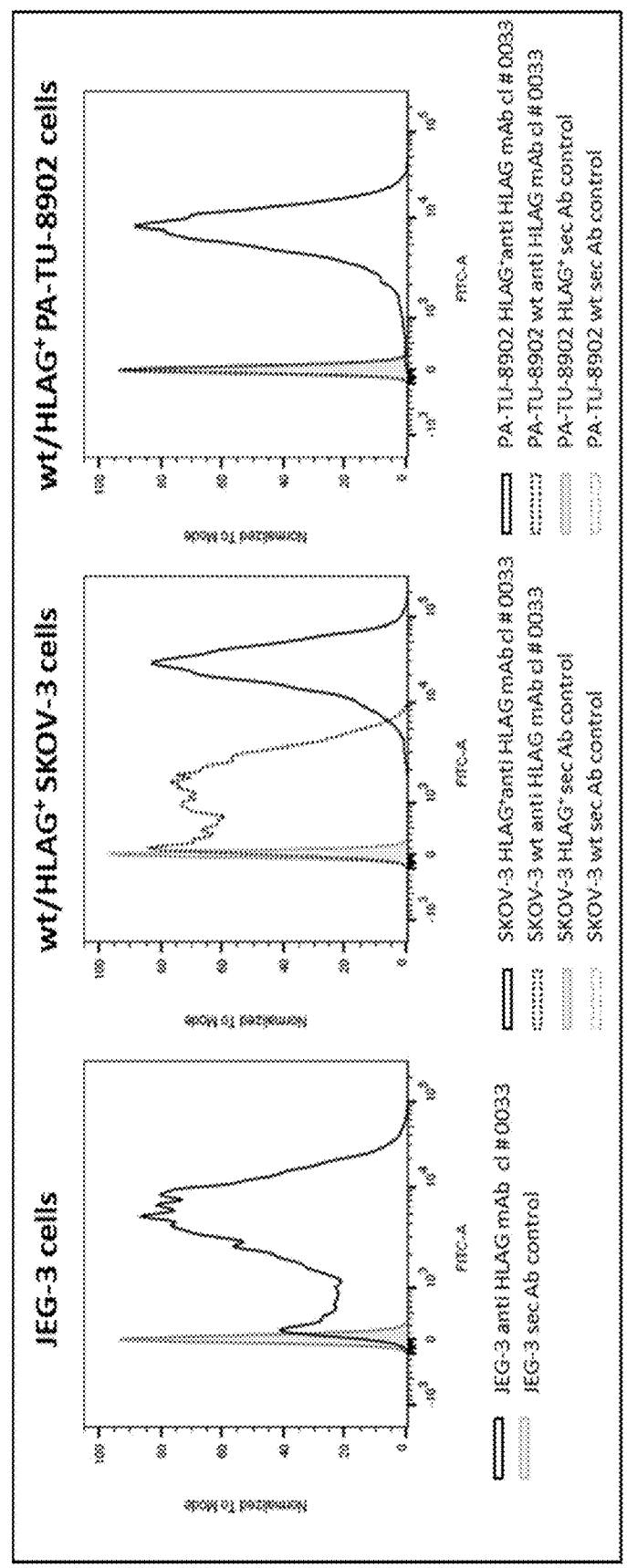
Figure 5D:
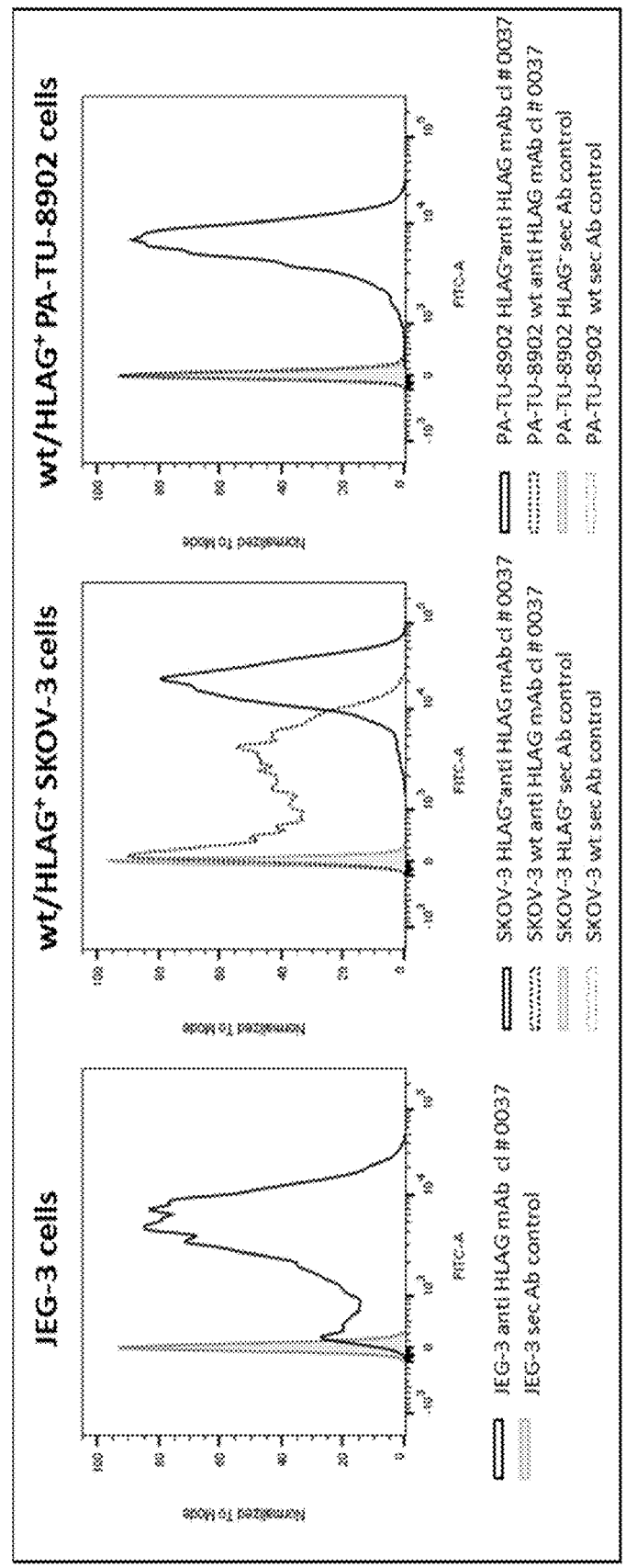

The corresponding SPR sensograms are in FIG. 3A and FIG. 3B.

In a further experiment the following reference antibodies (obtained from different commercial vendors) were compared for binding to monomeric human HLA-G MHC I (SEQ ID NO: 23 ("HLA-G-0003")) and "degrafted" human HLA-G with consensus HLA-A specific positions (SEQ ID NO: 24 ("HLA-G-0007")):

MEM/G9, 87G, G233, 2A12, 4H84, 5A6G7, 6D463, 9-1F10, MEM-G/1, MEM-G/11, MEM-G/2 and MEM-G/4 ("-" indicates no detectable binding).

| Antigen | Antibody | ka (1/Ms) | kd (1/s) | t½ (Min) | KD (M) |
|---|---|---|---|---|---|
| wt HLA-G (SEQ ID NO: 25) (monomer) | MEM/G9 | 1.5E+05 | 1.1E−03 | 10 | 7.7E−09 |
| | 87G | — | — | — | — |
| | G233 | 1.8E+05 | 3.7E−03 | 3 | 2.0E−08 |
| | 2A12 | — | — | — | — |

-continued

| Antigen | Antibody | ka (1/Ms) | kd (1/s) | t½ (Min) | KD (M) |
|---|---|---|---|---|---|
| | 4H84 | — | — | — | — |
| | 5A6G7 | — | — | — | — |
| | 6D463 | — | — | — | — |
| | 9-1F10 | — | — | — | — |
| | MEM-G/1 | — | — | — | — |
| | MEM-G/11 | 7.4E+04 | 8.5E−04 | 14 | 1.2E−08 |
| | MEM-G/2 | — | — | — | — |
| | MEM-G/4 | — | — | — | — |
| HLA-A consensus on HLA-G degraft (SEQ ID NO: 26) | MEM/G9 | 1.2E+05 | 3.6E−02 | 0.3 | 3.0E−07 |
| | 87G | — | — | — | — |
| | G233 | — | — | — | — |
| | 2A12 | — | — | — | — |
| | 4H84 | — | — | — | — |
| | 5A6G7 | — | — | — | — |
| | 6D463 | — | — | — | — |
| | 9-1F10 | — | — | — | — |
| | MEM-G/1 | — | — | — | — |
| | MEM-G/11 | 8.9E+04 | 1.2E−03 | 10 | 1.3E−08 |
| | MEM-G/2 | — | — | — | — |
| | MEM-G/4 | — | — | — | — |

Interestingly, most of the measured antibodies did not show any specific binding to monomeric human HLA-G MHC I (SEQ ID NO: 25 ("HLA-G-0003")) including also antibody 87G. The binding to oligomeric forms of HLA-G as described in literature might be avidity driven due to the increased binding sites of oligomeric forms.

Only antibody MEM/G9 with a KD value of the binding affinity of $7.7E^{-09}$ M, antibody G233 with a KD value of $2.0E^{-08}$ M and MEM-G/11 with a KD value of the binding affinity of $1.2E^{-08}$ M showed binding to monomeric wt human HLA-G MHC I complex. However, one of these antibodies MEM-G/11 also showed some binding/crossreactivity to HLA-A consensus on HLA-G degraft (SEQ ID NO:26). In addition, another antibody (MEM/G9) also showed stronger unspecific binding to HLA-A consensus on HLA-G degraft (SEQ ID NO:26).

Example 4

Receptor Blocking (with Mono-, Di- and Trimeric HLA-G)

a) Biochemical Comparison of Anti-HLA-G Antibodies for Their ILT2 and -4 Blocking Properties Streptavidin coated plates (Nunc, MicroCoat #11974998001) were coated with 25 µl/well biotinylated human wt HLA-G at a concentration of 500 ng/ml and incubated at 4° C. overnight. After washing (3×90 µl/well with PB ST-buffer) 25 µl anti-HLA-G samples were added in decreasing concentrations starting at 8 µg/ml, then diluted in 1:3 steps and incubated 1 h at RT. After washing (3×90 µl/well with PBST-buffer) 25 µl/well c-myc-tagged recombinant ILT-2 receptor was added at a concentration of 150 ng/ml and incubated for 1 h at room temperature. After washing (3×90 µl/well with PBST-buffer) 25 µl/well goat-anti-c-myc-POD (Bethyl #A190-104P 1:7000 in OSE) was added and incubated at RT for 1 h on a shaker. After washing (6×90 µl/well with PBST-buffer), 25 µl/well TMB substrate (Roche, 11835033001) was added and incubated until OD 2-3. Measurement took place on a Tecan Safire 2 instrument at 370/492 nm HLA-G Antibodies Neutralize HLA-G-ILT2/4 Receptor Engagement (IC50 [nM])

| Candidate | % inh. ILT2 (3 µg/ml antibody) | $IC_{50}$ ILT2 [nM] | | | % inh. ILT4 | $IC_{50}$ ILT4 [nM] | | |
|---|---|---|---|---|---|---|---|---|
| | | M | D | T | | M | D | T |
| HLA-G-0032 | 86.84 | 8.4 | 1.3 | 0.4 | 42.99 | n.d. | 50.3 | 71.3 |
| HLA-G-0033 | 85.28 | 8 | 1.2 | 0.5 | 44.62 | n.d. | 31.3 | 61.5 |
| HLA-G-0036 | 84.23 | 3.3 | 1.5 | 0.4 | 40.52 | n.d. | 61.9 | 51.3 |
| HLA-G-0037 | 82.91 | 13 | 0.8 | 0.1 | 41.05 | n.d. | n.d. | >200 |

The above table summarizes the blocking of interaction between rec. HLA-G proteins (monomer and oligomers) to its receptors ILT2 and ILT4 as assessed by ELISA. Shown are the % inhibition of the HLA-G/receptor interaction (for ILT2 and ILT4) as well as the relative IC50 values [nM] for the neutralization of the HLA-G/receptor interaction (in case the monomeric (M), dimeric (D) or trimeric (T) HLA-G proteins were used. The less pronounced ILT4 inhibition depends on the major ß-2M dependent interaction of this receptor.

The ELISA was set up by coating the biotinylated antigen wt HLA-G to strepdavidin plates. After incubation and washing steps, the respective antibodies were bound in a concentration range from 8-0 µg in 1:3 dilution steps. C-myc tagged ILT-2 or -4 receptor was added to the HLA-G-antibody complexes. After incubation and washing steps, detection of bound receptor was carried out by anti-cmyc-antibody-POD conjugates. IC50 values were determined from the resulting inhibition curves at the antibody concentrations generating the half-maximal inhibition. In case of the non-biotinylated HLA-G dimer and trimer antigens, immobilization was carried out by random coating on assay plates.

b) Biochemical Comparison of Anti-HLA-G Antibodies for Their ILT2 and -4 Blocking Properties Using a Different Assay Set-Up The ELISA was set up by coating the Fc tagged ILT2 and ILT4 respectively to Maxisorp microtiter plates. After incubation and washing steps, the respective antibodies were added at a concentration of 100 nM. Soluble His tagged monomeric, dimeric or trimeric HLA-G was added to the wells. After incubation and washing steps, detection of bound receptor was carried out by anti-His-antibody-POD conjugates. Percentage inhibition (%) was calculated in comparison to values obtained from wells with ILT2/4+ HLA-G (mono-, di-, or Trimer) without anti HLA-G or ILT2/4 antibodies (100% binding=0% inhibition).

| Candidate | % inh. ILT2 | | | % inh. ILT4 | | |
|---|---|---|---|---|---|---|
| | M | D | T | M | D | T |
| HLA-G-0032 | 75 | 95 | 93 | 12 | 62 | 68 |
| HLA-G-0033 | 75 | 95 | 93 | 14 | 70 | 71 |
| HLA-G-0036 | 71 | 94 | 93 | 23 | 60 | 70 |
| HLA-G-0037 | 73 | 96 | 93 | 1 | 61 | 67 |

The above table summarizes the blocking of interaction between rec. HLA-G proteins (monomer and oligomers) to its receptors ILT2 and ILT4 as assessed by ELISA. Shown are the % inhibitions of the HLA-G/receptor interaction (for ILT2 and ILT4). The less pronounced ILT4 inhibition depends on the major ß2M dependent interaction of this receptor.

The bar graph below shows % inhibition achieved by the described anti-HLA-G antibody in comparison to commercially available antibodies as shown in the graph. Commercially available HLA-G antibodies 87G, MEM/G09 and G233 do not block HLA-G/ILT2 or ILT4 interaction as efficiently as the described antibodies. Further, the commercially available antibodies lead to increased binding of HLA-G to ILT2 or ILT4 upon binding in some cases.

Example 5

Binding of Anti HLA-G Antibodies to Cells
a) Cell-Surface HLA-G Binding ELISA

25 µl/well of JEG3 cells (naturally expressing HLA-G, 20000 cells/well), Skov-3 cells or Skov-3 cells expressing recombinant HLA-G on the cell surface (both 10000 cells/well) were seeded into tissue culture treated 384-well plates (Corning, 3701) and incubated at 37° C. overnight. The next day 12.5 µl of anti-HLA-G samples (final dilution 1:3) were added and incubated for 2 h at 4° C. Cells were fixed by addition of 50 µl/well glutaraldehyde to a final concentration of 0.05% (Sigma Cat.No: G5882; Lot No.: 056K5318). After washing (3×90 µl/well with PBST-buffer) 25 µl/well goat-anti-mouse H+L-POD (Biorad #170-6561 1:2000 in OSEP) or donkey-anti-rabbit IgG POD (GE #NA9340V, 1:5000 in OSE) was added and incubated at RT for 1 h on shaker. For detection of rat IgGs a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (4×90 µl/well with PBST-buffer) 25 µl/well TMB substrate (Roche, 11835033001) was added and incubated until OD 2-3. Measurement took place on a Tecan Safire 2 instrument at 370/492 nm.

| Antibody | Jeg3 | wt Skov3 | HLA-G+ Skov3 | wt PA-TU-8902 | HLA-G+ PA-TU-8902 |
|---|---|---|---|---|---|
| HLA-G-0032 | +++ | − | +++ | − | +++ |
| HLA-G-0033 | +++ | + | +++ | − | +++ |
| HLA-G-0036 | + | − | ++ | − | + |
| HLA-G-0037 | +++ | + | +++ | − | +++ |

The above table summarizes the binding of different rat anti-human HLA-G monoclonal antibodies to HLA-G expressed on different cells and cell lines as assessed by FACS analysis. Either the binding to naturally HLA-G expressing JEG3 tumor cells or Skov3 or PA-TU-8902 transfectants and respective parental, untransfected cells is described.

b) Binding of HLA-G Antibodies to Natural or Recombinant HLA-G Expressed on Cells (as Assessed by FACS Analysis)

For flow cytometry analysis, cells were stained with anti HLA-G mAbs at 4° C. Briefly, 25 µl/well of each cell suspension (5×10⁴ cells/well) was transferred into a polypropylene 96-Well V-bottom plate and prechilled in the fridge at 5° C. for 10 min. Anti-HLA-G samples were diluted in staining buffer to a 2-fold starting concentration of 80 µg/ml. A 4-fold serial dilution of the antibodies was performed and 25 µl/well of the antibody solution was added to the prepared cells and incubated for 1 h at 5° C. Cells were washed twice with 200 µl/well staining buffer and centrifugation at 300 g for 3 min. For detection fluorescent labeled anti-species antibody (goat anti rat IgG (H+L) conjugated to Alexa 488, Life technologies #A11006; or goat anti-mouse IgG (H+L), Life technologies #A11001) was diluted to 20 µg/ml in staining buffer and cell pellets were resuspended in 50 µl/well detection antibody. After a 1 hour incubation at 5° C. cells were again washed twice with staining buffer, resuspended in 70 µl of staining buffer and measured at a FACS Canto II.

An exemplary FACS staining for clones HLA-G#0032-0037 is given in the FACS overlays of FIG. 5A, FIG. 5B, FIG. 5C, and FIG. 5D:

Example 6

Anti HLA-G Antibodies Inhibit/Modulate the Interaction of Recombinant ILT2 with HLA-G Naturally Expressed on JEG3 Cells For analysis, JEG3 cells (ATCC HTB36) were stained with ILT2-Fc fusion proteins (control=no inhibition) with or without pre-incubation with different anti-HLA-G antibodies. For the pre-incubation with anti-HLA-G antibodies 25 µl/well of the cell suspension was transferred into a polypropylene 96-Well V-bottom plate and prechilled in the at 4° C. for 10 min. Anti HLA-G antibodies or reference antibodies (G233, MEM-G/9 or 87G) were diluted in staining buffer to a 2-fold concentration of 20 µg/ml and 25 µl/well of the antibody solution was added to the prepared cells and incubated for 1 h at 5° C. Cells were washed twice with 200 µl/well staining buffer with centrifugation at 300 g for 3 min and finally resuspended in 25 µl/well staining buffer.

The detection of human ILT2-Fc Chimera protein (RD #2017-T2-050) to a) JEG3 cells pre-incubated anti HLA-G mAb or b) untreated JEG3 cells as reference was determined as follows: Briefly, the ILT2-Fc or control human IgG (Jackson-Immuno-Research #009-000-003) were diluted in staining buffer to a 2-fold concentration of 20 µg/ml (ILT2) and 25 µl/well of the ILT2-Fc protein solution was added to the prepared cells and incubated for 2 h at 5° C. Cells were again washed twice with 200 µl/well staining buffer the human ILT2-Fcprotein was detected with fluorescent labeled anti human IgG Fc-gamma specific antibody (F(ab')$_2$ Fragment Goat Anti-Human IgG, Fcγ fragment specific-FITC, Jackson-Immuno-Research #109-096-008) at a dilution of 10 µg/ml in staining buffer. Cell pellets were resuspended in 50 µl/well detection antibody. After a 1-hour incubation at 5° C. cells were washed twice with staining buffer, resuspended in 70 µl and measured at a FACS Canto II to determine ILT2 binding to JEG 3 cells.

As control, the anti-HLA-G antibodies bound to JEG-3 pre-incubated cells were detected by using anti-species antibody (goat anti-rat IgG (H+L) conjugated to Alexa 488, (Life technologies #A11006), or goat-anti mouse IgG (H+L)-Alexa 488, (Life technologies, #A11001) at a concentration of 10 µg/ml.

Figure 6B:
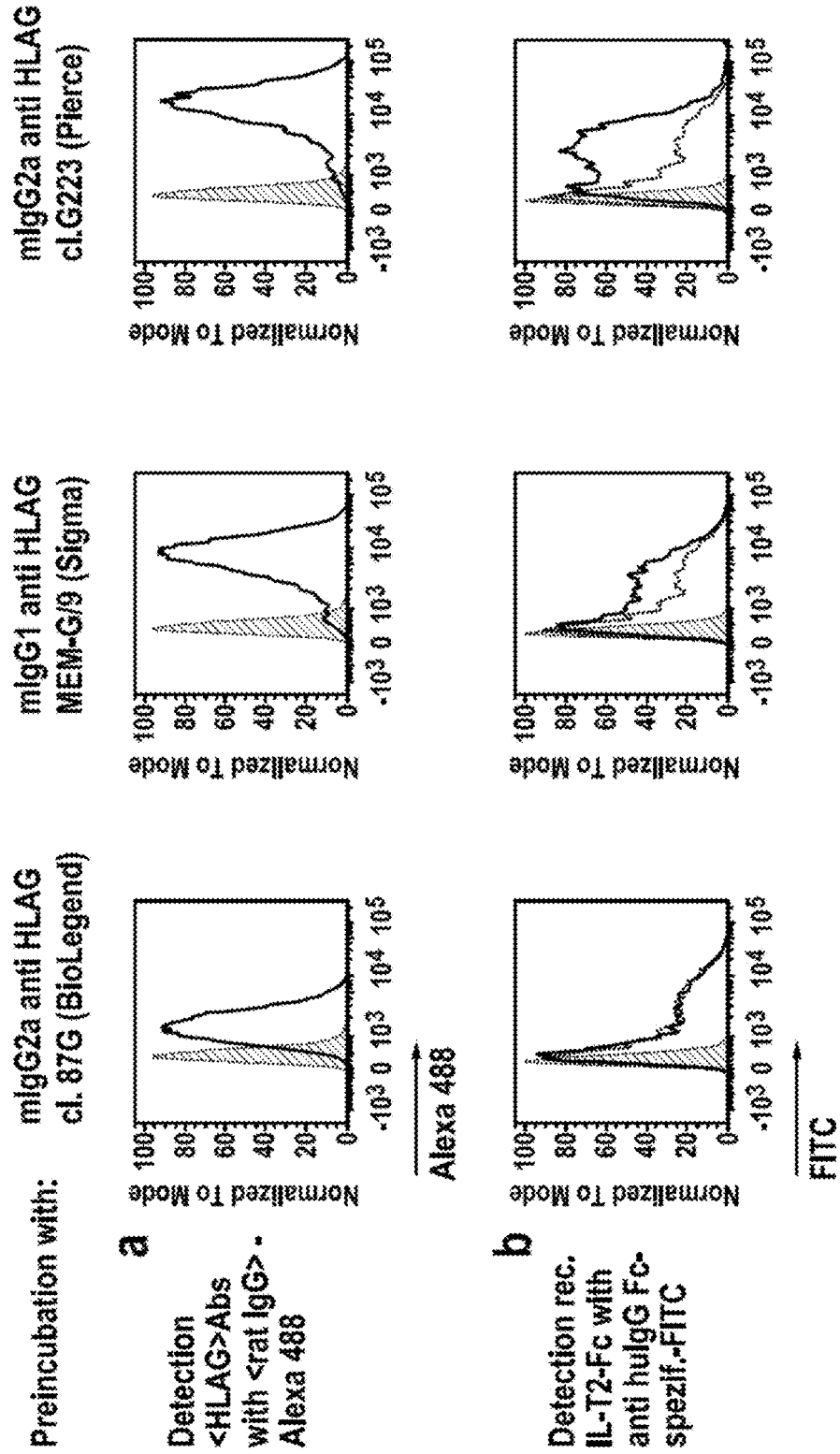

The graph in FIG. 6A and FIG. 6B shows the respective ability of different HLA-G antibodies to modify the interaction and binding of recombinant ILT2 to HLA-G naturally expressed on JEG3 tumor cells.

The following table summarizes the results from the experiments. The binding of the anti-HLA-G antibodies to JEG3 cells is depicted as +=weak binding –+++=strong binding. The ability of the anti-HLA-G antibodies either to inhibit/block or increase the binding of ILT2 to the HLA-G expressing JEG3 cells. In the last column, the binding of the recombinant ILT2 to the cells or the inhibition/blockade thereof is shown/quantified (staining of ILT2-Fc in the absence of an anti-HLA-G antibody was set to 100% binding which 0% inhibition, a negative value indicates an even increased binding; staining signal differences below 5% were not significant as categorizes with no effect):

| Antibody | Binding on JEG-3 cells | HLA-G:ILT2 interaction | Inhibition of ILT2 binding to Jeg3 cells |
|---|---|---|---|
| no mAb (ctrl) | – | — | 0% inhibition = 100% binding |
| HLA-G-0032 | +++ | inhibits binding of ILT2 | 98.1% inhibition |
| HLA-G-0033 | +++ | slightly increased binding of ILT2 | –9.3% (=increase/stimulation of ILT2 binding) |
| HLA-G-0036 | + | no significant effect | 2.3% inhibition |
| HLA-G-0037 | +++ | inhibits binding of ILT2 | 96.5% inhibition |
| 87G | ++ | no significant effect | 2.3% inhibition |
| MEM-G/9 | +++ | inhibits binding of ILT2 | –27.9% (=increase/stimulation of ILT2 binding) |
| G223 | +++ | inhibits binding of ILT2 | –55.8% (=increase/stimulation of ILT2 binding) |

Example 7

Monocyte Cytokine Restoration Assay (After HLA-G Mediated Suppression)

The following co-culture assay of HLA-G-expressing cells with Monocytes was used for the functional characterization of the different rat anti-human HLA-G monoclonal antibodies. Peripheral human Monocytes were isolated from blood of healthy donors. Briefly, blood was collected in tubes containing an anticoagulant agent and diluted 1:2 in PBS. To isolate peripheral blood mononuclear cells (PBMCs) 30 ml of the mixture was transferred to each Leucosep tube with prefilled separation medium. The PBMC specific band was collected after 12 min centrifugation (1200×g without brake), washed three times with PBS and centrifuged for 10 min at 300×g. Finally, cell pellets were resuspended in MACS buffer from Miltenyi and human monocytes were isolated from the PBMCs via magnetic separation with the human Monocyte Isolation Kit II from Miltenyi (#130-091-153) according to the manufacturer's instructions (negative selection). The isolated monocytes were resuspended in primary cell culture medium (RPMI 1640, PAN #P04-17500 supplemented with 10% FCS, Gibco #10500; 2 mM L-glutamine, Sigma #G7513; 1 mM Sodium Pyruvate, Gibco #11360; MEM Non-Essential Amino Acids, Gibco #11140; 0.1 mM 2-Mercaptoethanol, Gibco #31350; MEM Vitamins, Gibco #11120; Penicillin Streptomycin, Gibco #15140) at a density of 5×10e5 cells/ml. The enrichment of $CD14^+CD16^+$ cells was monitored by flow cytometry and ILT2 and ILT4 expression of the cells was analyzed. For the co-culture assay of the enriched monocytes with HLA-G-expressing cells, JEG-3 cells were seeded one day prior to the assay in a 96-well-flat bottom tissue culture plate with 8×10e3 cells/well in 100 µl in JEG-3 culture medium (MEM Eagle with EBSS and L-glutamine, PAN #P04-00509 supplemented with 10% FCS, Gibco #10500; 1 mM Sodium Pyruvate, Gibco #11360; MEM Non-Essential Amino Acids Gibco #11140) to form a confluent layer on the day of the assay. The adherent JEG-3 cells were pre-incubated with a 4 fold serial dilution of anti HLA-G antibodies in primary cell culture medium. Therefore the supernatant from the adherent JEG-3 cells was removed and 50 µl/Well of the prepared antibody solution was added and incubated at 37° C. and 5% CO2 in a humidified atmosphere for 1 h. Human monocytes were added to the anti HLA-G antibodies pre-incubated JEG-3 cells with 2.5×10e4 human monocytes/Well in 50 µl primary cell culture medium and co-culture was incubated at 37° C. and 5% CO2 in a humidified atmosphere overnight (approx. 18-20 hours). On the next day a LPS stimulation with 50 ng/ml LPS was performed for 7 h and afterwards the supernatant of the co-culture was harvested. The concentration of TNF alpha of the co-culture supernatant was determined using the Human TNF alpha ELISA Ready-SET-Go!® from eBioscience (#88-7346-88).

The below table summarizes the functional characteristics of given HLA-G antibody candidates.

Functional anti-HLA-G antibodies are able to restore a suppressed immune response, i.e. restoration of LPS-induced TNFa production by Monocytes in co-culture with HLA-G-expressing cells.

| Donor | Antibody | HLA-G-0032 (#32) | HLA-G-0033 (#33) | HLA-G-0036 (#36) | HLA-G-0037 (#37) |
|---|---|---|---|---|---|
| 1 | | ++ | – | – | +++ |
| 2 | | + | – | – | ++ |
| 3 | | (+) | – | – | (+) |
| 4 | | (+) | – | – | ++ |
| 7 | | + | – | n.t. | +++ |
| 8 | | + | – | n.t. | ++ |

The invention claimed is:

1. An isolated antibody that binds to human HLA-G, wherein the antibody comprises (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

2. An isolated antibody that binds to human HLA-G, wherein the antibody comprises (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising the amino acid sequence of SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6.

3. An isolated antibody that binds to human HLA-G, wherein the antibody comprises a VH sequence of SEQ ID NO:7 and a VL sequence of SEQ ID NO:8 or a humanized variant of the VH and VL of the antibody thereof, wherein the humanized variant comprises (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

4. The anti-HLA-G antibody according to any one of claims 1 to 3, wherein the antibody is characterized independently by the following properties:

the anti-HLA-G antibody
a) does not cross-react with a modified human HLA-G ß2M MHC I complex comprising SEQ ID NO:26;
b) does not cross-react with human HLA-A2 ß2M MHC I complex comprising SEQ ID NO:21 and SEQ ID NO: 19;
c) does not cross-react with a mouse H2Kd ß2M MHC I complex comprising SEQ ID NO:27;
d) does not cross-react with rat RT1A ß2M MHC I complex comprising SEQ ID NO:29;
e) inhibits ILT2 binding to monomeric HLA-G ß2M MHC I complex;
f) inhibits ILT2 binding to monomeric HLA-G ß2M MHC I complex, by more than 50%;
g) inhibits ILT2 binding to monomeric, dimeric, trimeric HLA-G ß2M MHC I complex by more than 50%;
h) inhibits ILT2 binding to JEG3 cells;
i) wherein the antibody binds to JEG3 cells, and wherein the antibody inhibits ILT2 binding to JEG3 cells; or
j) wherein the antibody binds to human HLA-G ß2M MHC I complex, and wherein the antibody inhibits ILT2 binding to monomeric, dimeric, or trimeric HLA-G ß2M MHC I complex by more than 60% and inhibits ILT4 binding to dimeric or trimeric HLA-G ß2M MHC I complex by more than 50%.

5. The antibody of any one of claims 1-3, wherein the antibody is of IgG1 isotype.

6. The antibody of claim 5, wherein the antibody is of IgG1 isotype with mutations L234A, L235A and P329G (numbering according to the EU index of Kabat).

7. A pharmaceutical formulation comprising the antibody of claim 6 and a pharmaceutically acceptable carrier.

8. A pharmaceutical formulation comprising the antibody of any one of claims 1-3 and a pharmaceutically acceptable carrier.

9. An isolated antibody that binds to human HLA-G, wherein the antibody comprises a VH sequence of SEQ ID NO:7 and a VL sequence of SEQ ID NO:8.

* * * * *

SEQUENCE LISTING

<160> NUMBER OF SEQ ID NOS: 39

<210> SEQ ID NO 1
<211> LENGTH: 5
<212> TYPE: PRT
<213> ORGANISM: Rattus sp.

<400> SEQUENCE: 1

Ser Tyr Asp Met His
1               5

<210> SEQ ID NO 2
<211> LENGTH: 17
<212> TYPE: PRT
<213> ORGANISM: Rattus sp.

<400> SEQUENCE: 2

Trp Ile Tyr Pro Gly Asn Gly Asn Thr Lys Tyr Asn Gln Lys Phe Asn
1               5                   10                  15

Gly

<210> SEQ ID NO 3
<211> LENGTH: 12
<212> TYPE: PRT
<213> ORGANISM: Rattus sp.

<400> SEQUENCE: 3

Pro Thr Val Ala Thr Arg Tyr Asn Trp Phe Ala Tyr
1               5                   10

<210> SEQ ID NO 4
<211> LENGTH: 10
<212> TYPE: PRT
<213> ORGANISM: Rattus sp.

<400> SEQUENCE: 4

Ser Ala Ser Ser Ser Val Asn Tyr Met His
1               5                   10

<210> SEQ ID NO 5
<211> LENGTH: 7
<212> TYPE: PRT
<213> ORGANISM: Rattus sp.

<400> SEQUENCE: 5

Leu Thr Ser Asn Leu Ala Ser
1               5

<210> SEQ ID NO 6
<211> LENGTH: 10
<212> TYPE: PRT
<213> ORGANISM: Rattus sp.

<400> SEQUENCE: 6

Gln Gln Trp Ser Ser Asn Leu Pro Ile Thr
1               5                   10

<210> SEQ ID NO 7
<211> LENGTH: 121
<212> TYPE: PRT
<213> ORGANISM: Rattus sp.

<400> SEQUENCE: 7

Gln Val Gln Leu Gln Gln Ser Gly Ala Glu Leu Val Lys Pro Gly Ser

```
                1               5                  10                  15
            Ser Val Lys Ile Ser Cys Lys Ala Ser Gly Tyr Ser Phe Pro Ser Tyr
                                20                  25                  30

Asp Met His Trp Ile Lys Gln Gln Pro Gly Asn Gly Leu Glu Trp Ile
                            35                  40                  45

Gly Trp Ile Tyr Pro Gly Asn Gly Asn Thr Lys Tyr Asn Gln Lys Phe
                50                  55                  60

Asn Gly Lys Ala Ser Leu Thr Ala Asp Lys Ser Ser Thr Ala Tyr
            65                  70                  75                  80

Met Gln Leu Ser Ser Leu Thr Ser Glu Asp Ser Ala Val Tyr Phe Cys
                            85                  90                  95

Ala Lys Pro Thr Val Ala Thr Arg Tyr Asn Trp Phe Ala Tyr Trp Gly
                        100                 105                 110

Gln Gly Thr Leu Val Thr Val Ser Ser
                        115                 120

<210> SEQ ID NO 8
<211> LENGTH: 107
<212> TYPE: PRT
<213> ORGANISM: Rattus sp.

<400> SEQUENCE: 8

Gln Ile Val Leu Thr Gln Ser Pro Ala Leu Met Ser Ala Ser Pro Gly
            1               5                  10                  15

Glu Lys Val Thr Met Thr Cys Ser Ala Ser Ser Ser Val Asn Tyr Met
                            20                  25                  30

His Trp Tyr Gln Gln Lys Pro Arg Ser Ser Pro Lys Pro Trp Ile Tyr
                        35                  40                  45

Leu Thr Ser Asn Leu Ala Ser Gly Val Pro Ala Arg Phe Ser Gly Ser
                50                  55                  60

Gly Ser Gly Thr Ser Tyr Ser Leu Thr Ile Ser Thr Met Glu Ala Glu
            65                  70                  75                  80

Asp Ala Ala Thr Tyr Tyr Cys Gln Gln Trp Ser Ser Asn Leu Pro Ile
                            85                  90                  95

Thr Phe Gly Ser Gly Thr Lys Leu Glu Ile Lys
                        100                 105

<210> SEQ ID NO 9
<211> LENGTH: 5
<212> TYPE: PRT
<213> ORGANISM: Rattus sp.

<400> SEQUENCE: 9

Thr Tyr Ser Val Ser
            1               5

<210> SEQ ID NO 10
<211> LENGTH: 16
<212> TYPE: PRT
<213> ORGANISM: Rattus sp.

<400> SEQUENCE: 10

Ala Ile Trp Ser Gly Gly Ser Thr Asp Tyr Asn Ser Ala Leu Lys Ser
            1               5                  10                  15

<210> SEQ ID NO 11
<211> LENGTH: 12
<212> TYPE: PRT
<213> ORGANISM: Rattus sp.
```

<400> SEQUENCE: 11

Met Asn Asn Lys Phe Gly Tyr Trp Tyr Phe Asp Leu
1               5                   10

<210> SEQ ID NO 12
<211> LENGTH: 11
<212> TYPE: PRT
<213> ORGANISM: Rattus sp.

<400> SEQUENCE: 12

Arg Ala Ser Glu Thr Val Ser Thr Met Leu His
1               5                   10

<210> SEQ ID NO 13
<211> LENGTH: 7
<212> TYPE: PRT
<213> ORGANISM: Rattus sp.

<400> SEQUENCE: 13

Leu Ala Ser His Leu Glu Ser
1               5

<210> SEQ ID NO 14
<211> LENGTH: 9
<212> TYPE: PRT
<213> ORGANISM: Rattus sp.

<400> SEQUENCE: 14

Gln Gln Thr Trp Asn Asp Pro Leu Thr
1               5

<210> SEQ ID NO 15
<211> LENGTH: 120
<212> TYPE: PRT
<213> ORGANISM: Rattus sp.

<400> SEQUENCE: 15

Gln Val Gln Leu Lys Glu Ser Gly Pro Gly Leu Val Gln Pro Ser Gln
1               5                   10                  15

Thr Leu Ser Leu Thr Cys Ser Val Ser Gly Phe Ser Leu Thr Thr Tyr
            20                  25                  30

Ser Val Ser Trp Val Arg Gln Pro Pro Gly Lys Gly Leu Glu Trp Ile
        35                  40                  45

Gly Ala Ile Trp Ser Gly Gly Ser Thr Asp Tyr Asn Ser Ala Leu Lys
    50                  55                  60

Ser Arg Leu Arg Ile Ser Arg Asp Thr Ser Lys Ser Gln Val Leu Leu
65                  70                  75                  80

Lys Met Asn Ser Leu Gln Thr Glu Asp Arg Ala Met Tyr Phe Cys Val
                85                  90                  95

Arg Met Asn Asn Lys Phe Gly Tyr Trp Tyr Phe Asp Leu Trp Gly Pro
            100                 105                 110

Gly Thr Met Val Thr Val Ser Ser
        115                 120

<210> SEQ ID NO 16
<211> LENGTH: 106
<212> TYPE: PRT
<213> ORGANISM: Rattus sp.

<400> SEQUENCE: 16

Asp Thr Val Leu Thr Gln Ser Pro Thr Leu Ala Val Ser Pro Gly Glu
1               5                   10                  15

Lys Ile Thr Ile Ser Cys Arg Ala Ser Glu Thr Val Ser Thr Met Leu
            20                  25                  30

His Trp Tyr Gln Gln Lys Pro Gly Gln Gln Pro Lys Leu Leu Ile Ser
        35                  40                  45

Leu Ala Ser His Leu Glu Ser Gly Val Pro Ala Arg Phe Thr Gly Ser
    50                  55                  60

Gly Ser Gly Thr Asp Phe Thr Leu Thr Ile Asp Pro Val Glu Ala Asp
65                  70                  75                  80

Asp Thr Ala Thr Tyr Tyr Cys Gln Gln Thr Trp Asn Asp Pro Leu Thr
            85                  90                  95

Phe Gly Ser Gly Thr Lys Leu Glu Ile Lys
            100                 105

<210> SEQ ID NO 17
<211> LENGTH: 314
<212> TYPE: PRT
<213> ORGANISM: Homo sapiens

<400> SEQUENCE: 17

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
            85                  90                  95

Trp Met Ile Gly Cys Asp Leu Gly Ser Asp Gly Arg Leu Leu Arg Gly
        100                 105                 110

Tyr Glu Gln Tyr Ala Tyr Asp Gly Lys Asp Tyr Leu Ala Leu Asn Glu
    115                 120                 125

Asp Leu Arg Ser Trp Thr Ala Ala Asp Thr Ala Ala Gln Ile Ser Lys
130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
            165                 170                 175

Glu Met Leu Gln Arg Ala Asp Pro Pro Lys Thr His Val Thr His His
        180                 185                 190

Pro Val Phe Asp Tyr Glu Ala Thr Leu Arg Cys Trp Ala Leu Gly Phe
    195                 200                 205

Tyr Pro Ala Glu Ile Ile Leu Thr Trp Gln Arg Asp Gly Glu Asp Gln
210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Glu Pro Leu Met Leu
        260                 265                 270

```
Arg Trp Lys Gln Ser Ser Leu Pro Thr Ile Pro Ile Met Gly Ile Val
        275                 280                 285

Ala Gly Leu Val Val Leu Ala Val Val Thr Gly Ala Ala Val Ala
290                 295                 300

Ala Val Leu Trp Arg Lys Lys Ser Ser Asp
305                 310
```

<210> SEQ ID NO 18
<211> LENGTH: 274
<212> TYPE: PRT
<213> ORGANISM: Homo sapiens

<400> SEQUENCE: 18

```
Gly Ser His Ser Met Arg Tyr Phe Ser Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175

Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
210                 215                 220

Thr Gln Asp Val Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Leu Met Leu
            260                 265                 270

Arg Trp
```

<210> SEQ ID NO 19
<211> LENGTH: 99
<212> TYPE: PRT
<213> ORGANISM: Homo sapiens

<400> SEQUENCE: 19

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 20
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: modified human HLA-G (wherein the HLA-G
      specific amino acids have been replaced by HLA-A consensus amino
      acids (= degrafted HLA-G)ECD

<400> SEQUENCE: 20

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ala Ala Ser Pro Arg Met Glu Pro Arg
        35                  40                  45

Ala Pro Trp Val Glu Gln Glu Gly Pro Glu Tyr Trp Asp Glu Glu Thr
50                  55                  60

Arg Asn Thr Lys Ala His Ala Gln Thr Asp Arg Val Asn Leu Gly Thr
65                  70                  75                  80

Leu Arg Gly Cys Tyr Asn Gln Ser Glu Ala Gly Ser His Thr Leu Gln
                85                  90                  95

Trp Met Ile Gly Cys Asp Val Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
130                 135                 140

Arg Lys Cys Glu Ala Ala His Val Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Val Glu Leu Val Glu Thr Arg Pro Ala Gly Asp Gly Thr
225                 230                 235                 240

```
Phe Gln Lys Trp Ala Ala Val Val Pro Ser Gly Glu Gln Arg
                245                 250                 255

Tyr Thr Cys His Val Gln His Glu Gly Leu Pro Glu Pro Leu Thr Leu
            260                 265                 270

Arg Trp Lys
        275

<210> SEQ ID NO 21
<211> LENGTH: 341
<212> TYPE: PRT
<213> ORGANISM: Homo sapiens

<400> SEQUENCE: 21

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
```

```
                        325                 330                 335

Thr Ala Cys Lys Val
            340

<210> SEQ ID NO 22
<211> LENGTH: 275
<212> TYPE: PRT
<213> ORGANISM: Homo sapiens

<400> SEQUENCE: 22

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 23
<211> LENGTH: 275
<212> TYPE: PRT
<213> ORGANISM: Mus musculus

<400> SEQUENCE: 23

Gly Pro His Ser Leu Arg Tyr Phe Val Thr Ala Val Ser Arg Pro Gly
1               5                   10                  15

Leu Gly Glu Pro Arg Phe Ile Ala Val Gly Tyr Val Asp Asp Thr Gln
```

```
                20                  25                  30

Phe Val Arg Phe Asp Ser Asp Ala Asp Asn Pro Arg Phe Glu Pro Arg
         35                  40                  45

Ala Pro Trp Met Glu Gln Glu Gly Pro Glu Tyr Trp Glu Glu Gln Thr
     50                  55                  60

Gln Arg Ala Lys Ser Asp Glu Gln Trp Phe Arg Val Ser Leu Arg Thr
 65                  70                  75                  80

Ala Gln Arg Cys Tyr Asn Gln Ser Lys Gly Gly Ser His Thr Phe Gln
                 85                  90                  95

Arg Met Phe Gly Cys Asp Val Gly Ser Asp Trp Arg Leu Leu Arg Gly
            100                 105                 110

Tyr Gln Gln Phe Ala Tyr Asp Gly Arg Asp Tyr Ile Ala Leu Asn Glu
        115                 120                 125

Asp Leu Lys Thr Trp Thr Ala Ala Asp Thr Ala Ala Leu Ile Thr Arg
    130                 135                 140

Arg Lys Trp Glu Gln Ala Gly Asp Ala Glu Tyr Tyr Arg Ala Tyr Leu
145                 150                 155                 160

Glu Gly Glu Cys Val Glu Trp Leu Arg Arg Tyr Leu Glu Leu Gly Asn
                165                 170                 175

Glu Thr Leu Leu Arg Thr Asp Ser Pro Lys Ala His Val Thr Tyr His
            180                 185                 190

Pro Arg Ser Gln Val Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Gln Lys Trp Ala Ala Val Val Val Pro Leu Gly Lys Glu Gln Asn
                245                 250                 255

Tyr Thr Cys His Val His His Lys Gly Leu Pro Glu Pro Leu Thr Leu
            260                 265                 270

Arg Trp Lys
        275

<210> SEQ ID NO 24
<211> LENGTH: 274
<212> TYPE: PRT
<213> ORGANISM: Rattus sp.

<400> SEQUENCE: 24

Gly Ser His Ser Leu Arg Tyr Phe Tyr Thr Ala Val Ser Arg Pro Gly
 1               5                  10                  15

Leu Gly Glu Pro Arg Phe Ile Ala Val Gly Tyr Val Asp Asp Thr Glu
            20                  25                  30

Phe Val Arg Phe Asp Ser Asp Ala Glu Asn Pro Arg Met Glu Pro Arg
        35                  40                  45

Ala Arg Trp Met Glu Arg Glu Gly Pro Glu Tyr Trp Glu Gln Gln Thr
    50                  55                  60

Arg Ile Ala Lys Glu Trp Glu Gln Ile Tyr Arg Val Asp Leu Arg Thr
 65                 70                  75                  80

Leu Arg Gly Cys Tyr Asn Gln Ser Glu Gly Gly Ser His Thr Ile Gln
                85                  90                  95

Glu Met Tyr Gly Cys Asp Val Gly Ser Asp Gly Ser Leu Leu Arg Gly
            100                 105                 110
```

```
Tyr Arg Gln Asp Ala Tyr Asp Gly Arg Asp Tyr Ile Ala Leu Asn Glu
            115                 120                 125

Asp Leu Lys Thr Trp Thr Ala Asp Phe Ala Gln Ile Thr Arg
    130                 135                 140

Asn Lys Trp Glu Arg Ala Arg Tyr Ala Glu Arg Leu Arg Ala Tyr Leu
145                 150                 155                 160

Glu Gly Thr Cys Val Glu Trp Leu Ser Arg Tyr Leu Glu Leu Gly Lys
                165                 170                 175

Glu Thr Leu Leu Arg Ser Asp Pro Pro Glu Ala His Val Thr Leu His
            180                 185                 190

Pro Arg Pro Glu Gly Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Asn
                245                 250                 255

Tyr Thr Cys Arg Val Glu His Glu Gly Leu Pro Lys Pro Leu Ser Gln
            260                 265                 270

Arg Trp

<210> SEQ ID NO 25
<211> LENGTH: 440
<212> TYPE: PRT
<213> ORGANISM: Homo sapiens

<400> SEQUENCE: 25

Arg Ile Ile Pro Arg His Leu Gln Leu Gly Cys Gly Gly Ser Gly Gly
1               5                   10                  15

Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Gly Gly Gly Gly Ser Gly
    130                 135                 140

Ser His Ser Met Arg Tyr Phe Ser Ala Ala Val Ser Arg Pro Gly Arg
145                 150                 155                 160

Gly Glu Pro Arg Phe Ile Ala Met Gly Tyr Val Asp Asp Thr Gln Phe
                165                 170                 175

Val Arg Phe Asp Ser Asp Ser Ala Cys Pro Arg Met Glu Pro Arg Ala
            180                 185                 190

Pro Trp Val Glu Gln Glu Gly Pro Glu Tyr Trp Glu Glu Glu Thr Arg
        195                 200                 205
```

```
Asn Thr Lys Ala His Ala Gln Thr Asp Arg Met Asn Leu Gln Thr Leu
210                 215                 220

Arg Gly Cys Tyr Asn Gln Ser Glu Ala Ser His Thr Leu Gln Trp
225                 230                 235                 240

Met Ile Gly Cys Asp Leu Gly Ser Asp Gly Arg Leu Leu Arg Gly Tyr
                245                 250                 255

Glu Gln Tyr Ala Tyr Asp Gly Lys Asp Tyr Leu Ala Leu Asn Glu Asp
                260                 265                 270

Leu Arg Ser Trp Thr Ala Ala Asp Thr Ala Ala Gln Ile Ser Lys Arg
                275                 280                 285

Lys Cys Glu Ala Ala Asn Val Ala Glu Gln Arg Arg Ala Tyr Leu Glu
290                 295                 300

Gly Thr Cys Val Glu Trp Leu His Arg Tyr Leu Glu Asn Gly Lys Glu
305                 310                 315                 320

Met Leu Gln Arg Ala Asp Pro Pro Lys Thr His Val Thr His His Pro
                325                 330                 335

Val Phe Asp Tyr Glu Ala Thr Leu Arg Cys Trp Ala Leu Gly Phe Tyr
                340                 345                 350

Pro Ala Glu Ile Ile Leu Thr Trp Gln Arg Asp Gly Glu Asp Gln Thr
                355                 360                 365

Gln Asp Val Glu Leu Val Glu Thr Arg Pro Ala Gly Asp Gly Thr Phe
                370                 375                 380

Gln Lys Trp Ala Ala Val Val Pro Ser Gly Glu Glu Gln Arg Tyr
385                 390                 395                 400

Thr Cys His Val Gln His Glu Gly Leu Pro Glu Pro Leu Met Leu Arg
                405                 410                 415

Trp Gly Ser Gly Leu Asn Asp Ile Phe Glu Ala Gln Lys Ile Glu Trp
                420                 425                 430

His Glu His His His His His His
            435                 440

<210> SEQ ID NO 26
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: exemplary modified human HLA-G beta-2M MHC
      class I complex (wherein the HLA-G specific amino acids have been
      replaced by HLA-A consensus amino acids (= degrafted HLA-G)

<400> SEQUENCE: 26

Arg Ile Ile Pro Arg His Leu Gln Leu Gly Cys Gly Gly Ser Gly Gly
1               5                   10                  15

Gly Gly Ser Gly Gly Gly Gly Ser Ile Gln Arg Thr Pro Lys Ile Gln
                20                  25                  30

Val Tyr Ser Arg His Pro Ala Glu Asn Gly Lys Ser Asn Phe Leu Asn
                35                  40                  45

Cys Tyr Val Ser Gly Phe His Pro Ser Asp Ile Glu Val Asp Leu Leu
50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
```

```
                100             105                 110
Gln Pro Lys Ile Val Lys Trp Asp Arg Asp Met Gly Gly Gly Gly Ser
            115                 120                 125
Gly Gly Gly Gly Ser Gly Gly Gly Ser Gly Gly Gly Ser Gly
        130                 135             140
Ser His Ser Met Arg Tyr Phe Ser Ala Ala Val Ser Arg Pro Gly Arg
145                 150                 155                 160
Gly Glu Pro Arg Phe Ile Ala Met Gly Tyr Val Asp Asp Thr Gln Phe
                165                 170                 175
Val Arg Phe Asp Ser Asp Ala Ala Ser Pro Arg Met Glu Pro Arg Ala
            180                 185                 190
Pro Trp Val Glu Gln Glu Gly Pro Glu Tyr Trp Asp Glu Thr Arg
        195                 200                 205
Asn Thr Lys Ala His Ala Gln Thr Asp Arg Val Asn Leu Gly Thr Leu
    210                 215                 220
Arg Gly Cys Tyr Asn Gln Ser Glu Ala Gly Ser His Thr Leu Gln Trp
225                 230                 235                 240
Met Ile Gly Cys Asp Val Gly Ser Asp Gly Arg Leu Leu Arg Gly Tyr
                245                 250                 255
Glu Gln Tyr Ala Tyr Asp Gly Lys Asp Tyr Leu Ala Leu Asn Glu Asp
            260                 265                 270
Leu Arg Ser Trp Thr Ala Ala Asp Thr Ala Ala Gln Ile Ser Lys Arg
        275                 280                 285
Lys Cys Glu Ala Ala His Val Ala Glu Gln Arg Arg Ala Tyr Leu Glu
    290                 295                 300
Gly Thr Cys Val Glu Trp Leu Arg Arg Tyr Leu Glu Asn Gly Lys Glu
305                 310                 315                 320
Thr Leu Gln Arg Ala Asp Pro Pro Lys Thr His Val Thr His His Pro
                325                 330                 335
Val Ser Asp His Glu Ala Thr Leu Arg Cys Trp Ala Leu Gly Phe Tyr
            340                 345                 350
Pro Ala Glu Ile Thr Leu Thr Trp Gln Arg Asp Gly Glu Asp Gln Thr
        355                 360                 365
Gln Asp Val Glu Leu Val Glu Thr Arg Pro Ala Gly Asp Gly Thr Phe
    370                 375                 380
Gln Lys Trp Ala Ala Val Val Pro Ser Gly Glu Glu Gln Arg Tyr
385                 390                 395                 400
Thr Cys His Val Gln His Glu Gly Leu Pro Glu Pro Leu Thr Leu Arg
                405                 410                 415
Trp Lys Gly Gly Gly Leu Asn Asp Ile Phe Glu Ala Gln Lys Ile Glu
            420                 425                 430
Trp His Glu His His His His His
        435                 440

<210> SEQ ID NO 27
<211> LENGTH: 441
<212> TYPE: PRT
<213> ORGANISM: Mus musculus

<400> SEQUENCE: 27

Thr Tyr Gln Arg Thr Arg Ala Leu Val Gly Cys Gly Ser Gly Gly
1               5                   10                  15
Gly Gly Ser Gly Gly Gly Ser Ile Gln Lys Thr Pro Gln Ile Gln
            20                  25                  30
```

```
Val Tyr Ser Arg His Pro Pro Glu Asn Gly Lys Pro Asn Ile Leu Asn
        35                  40                  45

Cys Tyr Val Thr Gln Phe His Pro Pro His Ile Glu Ile Gln Met Leu
 50                  55                  60

Lys Asn Gly Lys Lys Ile Pro Lys Val Glu Met Ser Asp Met Ser Phe
 65                  70                  75                  80

Ser Lys Asp Trp Ser Phe Tyr Ile Leu Ala His Thr Glu Phe Thr Pro
                 85                  90                  95

Thr Glu Thr Asp Thr Tyr Ala Cys Arg Val Lys His Asp Ser Met Ala
            100                 105                 110

Glu Pro Lys Thr Val Tyr Trp Asp Arg Asp Met Gly Gly Gly Gly Ser
            115                 120                 125

Gly Gly Gly Gly Ser Gly Gly Gly Ser Gly Gly Gly Ser Gly
    130                 135                 140

Pro His Ser Leu Arg Tyr Phe Val Thr Ala Val Ser Arg Pro Gly Leu
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Asp Asn Pro Arg Phe Glu Pro Arg Ala
            180                 185                 190

Pro Trp Met Glu Gln Glu Gly Pro Glu Tyr Trp Glu Glu Gln Thr Gln
            195                 200                 205

Arg Ala Lys Ser Asp Glu Gln Trp Phe Arg Val Ser Leu Arg Thr Ala
210                 215                 220

Gln Arg Cys Tyr Asn Gln Ser Lys Gly Gly Ser His Thr Phe Gln Arg
225                 230                 235                 240

Met Phe Gly Cys Asp Val Gly Ser Asp Trp Arg Leu Leu Arg Gly Tyr
                245                 250                 255

Gln Gln Phe Ala Tyr Asp Gly Arg Asp Tyr Ile Ala Leu Asn Glu Asp
            260                 265                 270

Leu Lys Thr Trp Thr Ala Ala Asp Thr Ala Ala Leu Ile Thr Arg Arg
            275                 280                 285

Lys Trp Glu Gln Ala Gly Asp Ala Glu Tyr Tyr Arg Ala Tyr Leu Glu
290                 295                 300

Gly Glu Cys Val Glu Trp Leu Arg Arg Tyr Leu Glu Leu Gly Asn Glu
305                 310                 315                 320

Thr Leu Leu Arg Thr Asp Ser Pro Lys Ala His Val Thr Tyr His Pro
                325                 330                 335

Arg Ser Gln Val Asp Val Thr Leu Arg Cys Trp Ala Leu Gly Phe Tyr
            340                 345                 350

Pro Ala Asp Ile Thr Leu Thr Trp Gln Leu Asn Gly Glu Asp Leu Thr
            355                 360                 365

Gln Asp Met Glu Leu Val Glu Thr Arg Pro Ala Gly Asp Gly Thr Phe
370                 375                 380

Gln Lys Trp Ala Ala Val Val Val Pro Leu Gly Lys Glu Gln Asn Tyr
385                 390                 395                 400

Thr Cys His Val His His Lys Gly Leu Pro Glu Pro Leu Thr Leu Arg
                405                 410                 415

Trp Lys Gly Gly Gly Leu Asn Asp Ile Phe Glu Ala Gln Lys Ile Glu
            420                 425                 430

Trp His Glu His His His His His His
            435                 440
```

<210> SEQ ID NO 28
<211> LENGTH: 441
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: exemplary human HLA-G/ mouse H2Kd beta-2M MHC class I complex wherein the positions specific for human HLA-G are grafted onto the mouse H2Kd framework

<400> SEQUENCE: 28

```
Thr Tyr Gln Arg Thr Arg Ala Leu Val Gly Cys Gly Gly Ser Gly Gly
1               5                   10                  15

Gly Gly Ser Gly Gly Gly Ser Ile Gln Lys Thr Pro Gln Ile Gln
            20                  25                  30

Val Tyr Ser Arg His Pro Pro Glu Asn Gly Lys Pro Asn Ile Leu Asn
            35                  40                  45

Cys Tyr Val Thr Gln Phe His Pro Pro His Ile Glu Ile Gln Met Leu
        50                  55                  60

Lys Asn Gly Lys Lys Ile Pro Lys Val Glu Met Ser Asp Met Ser Phe
65                  70                  75                  80

Ser Lys Asp Trp Ser Phe Tyr Ile Leu Ala His Thr Glu Phe Thr Pro
                85                  90                  95

Thr Glu Thr Asp Thr Tyr Ala Cys Arg Val Lys His Asp Ser Met Ala
            100                 105                 110

Glu Pro Lys Thr Val Tyr Trp Asp Arg Asp Met Gly Gly Gly Gly Ser
        115                 120                 125

Gly Gly Gly Gly Ser Gly Gly Gly Ser Gly Gly Gly Gly Ser Gly
130                 135                 140

Pro His Ser Leu Arg Tyr Phe Val Thr Ala Val Ser Arg Pro Gly Leu
145                 150                 155                 160

Gly Glu Pro Arg Phe Ile Ala Val Gly Tyr Val Asp Asp Thr Gln Phe
                165                 170                 175

Val Arg Phe Asp Ser Asp Ser Ala Ser Pro Arg Phe Glu Pro Arg Ala
            180                 185                 190

Pro Trp Val Glu Gln Glu Gly Pro Glu Tyr Trp Glu Glu Gln Thr Gln
        195                 200                 205

Arg Ala Lys Ser Asp Glu Gln Trp Phe Arg Met Ser Leu Gln Thr Ala
210                 215                 220

Arg Gly Cys Tyr Asn Gln Ser Glu Ala Ser Ser His Thr Phe Gln Arg
225                 230                 235                 240

Met Phe Gly Cys Asp Leu Gly Ser Asp Gly Arg Leu Leu Arg Gly Tyr
                245                 250                 255

Gln Gln Phe Ala Tyr Asp Gly Arg Asp Tyr Ile Ala Leu Asn Glu Asp
            260                 265                 270

Leu Arg Ser Trp Thr Ala Ala Asp Thr Ala Ala Leu Ile Thr Lys Arg
        275                 280                 285

Lys Trp Glu Ala Ala Asn Asp Ala Glu Tyr Tyr Arg Ala Tyr Leu Glu
290                 295                 300

Gly Glu Cys Val Glu Trp Leu His Arg Tyr Leu Glu Asn Gly Lys Glu
305                 310                 315                 320

Met Leu Gln Arg Thr Asp Ser Pro Lys Ala His Val Thr His His Pro
                325                 330                 335

Val Phe Asp Tyr Glu Ala Thr Leu Arg Cys Trp Ala Leu Gly Phe Tyr
            340                 345                 350
```

```
Pro Ala Glu Ile Ile Leu Thr Trp Gln Leu Asn Gly Glu Asp Leu Thr
            355                 360                 365

Gln Asp Val Glu Leu Val Glu Thr Arg Pro Ala Gly Asp Gly Thr Phe
    370                 375                 380

Gln Lys Trp Ala Val Val Val Pro Ser Gly Lys Glu Gln Asn Tyr
385                 390                 395                 400

Thr Cys His Val Gln His Glu Gly Leu Pro Glu Pro Leu Met Leu Arg
                405                 410                 415

Trp Lys Gly Gly Gly Leu Asn Asp Ile Phe Glu Ala Gln Lys Ile Glu
                420                 425                 430

Trp His Glu His His His His His His
                435                 440

<210> SEQ ID NO 29
<211> LENGTH: 440
<212> TYPE: PRT
<213> ORGANISM: Rattus sp.

<400> SEQUENCE: 29

Ala Gln Phe Ser Ala Ser Ala Ser Arg Gly Cys Gly Gly Ser Gly Gly
1               5                   10                  15

Gly Gly Ser Gly Gly Gly Gly Ser Ile Gln Lys Thr Pro Gln Ile Gln
                20                  25                  30

Val Tyr Ser Arg His Pro Pro Glu Asn Gly Lys Pro Asn Phe Leu Asn
                35                  40                  45

Cys Tyr Val Ser Gln Phe His Pro Pro Gln Ile Glu Ile Glu Leu Leu
    50                  55                  60

Lys Asn Gly Lys Lys Ile Pro Asn Ile Glu Met Ser Asp Leu Ser Phe
65                  70                  75                  80

Ser Lys Asp Trp Ser Phe Tyr Ile Leu Ala His Thr Glu Phe Thr Pro
                85                  90                  95

Thr Glu Thr Asp Val Tyr Ala Cys Arg Val Lys His Val Thr Leu Lys
                100                 105                 110

Glu Pro Lys Thr Val Thr Trp Asp Arg Asp Met Gly Gly Gly Gly Ser
                115                 120                 125

Gly Gly Gly Gly Ser Gly Gly Gly Ser Gly Gly Gly Gly Ser Gly
                130                 135                 140

Ser His Ser Leu Arg Tyr Phe Tyr Thr Ala Val Ser Arg Pro Gly Leu
145                 150                 155                 160

Gly Glu Pro Arg Phe Ile Ala Val Gly Tyr Val Asp Asp Thr Glu Phe
                165                 170                 175

Val Arg Phe Asp Ser Asp Ala Glu Asn Pro Arg Met Glu Pro Arg Ala
                180                 185                 190

Arg Trp Met Glu Arg Glu Gly Pro Glu Tyr Trp Glu Gln Gln Thr Arg
                195                 200                 205

Ile Ala Lys Glu Trp Glu Gln Ile Tyr Arg Val Asp Leu Arg Thr Leu
    210                 215                 220

Arg Gly Cys Tyr Asn Gln Ser Glu Gly Gly Ser His Thr Ile Gln Glu
225                 230                 235                 240

Met Tyr Gly Cys Asp Val Gly Ser Asp Gly Ser Leu Leu Arg Gly Tyr
                245                 250                 255

Arg Gln Asp Ala Tyr Asp Gly Arg Asp Tyr Ile Ala Leu Asn Glu Asp
                260                 265                 270

Leu Lys Thr Trp Thr Ala Ala Asp Phe Ala Ala Gln Ile Thr Arg Asn
```

```
              275                 280                 285
Lys Trp Glu Arg Ala Arg Tyr Ala Glu Arg Leu Arg Ala Tyr Leu Glu
        290                 295                 300

Gly Thr Cys Val Glu Trp Leu Ser Arg Tyr Leu Glu Leu Gly Lys Glu
305                 310                 315                 320

Thr Leu Leu Arg Ser Asp Pro Pro Glu Ala His Val Thr Leu His Pro
                325                 330                 335

Arg Pro Glu Gly Asp Val Thr Leu Arg Cys Trp Ala Leu Gly Phe Tyr
            340                 345                 350

Pro Ala Asp Ile Thr Leu Thr Trp Gln Leu Asn Gly Glu Asp Leu Thr
        355                 360                 365

Gln Asp Met Glu Leu Val Glu Thr Arg Pro Ala Gly Asp Gly Thr Phe
    370                 375                 380

Gln Lys Trp Ala Ser Val Val Pro Leu Gly Lys Glu Gln Asn Tyr
385                 390                 395                 400

Thr Cys Arg Val Glu His Glu Gly Leu Pro Lys Pro Leu Ser Gln Arg
                405                 410                 415

Trp Gly Ser Gly Leu Asn Asp Ile Phe Glu Ala Gln Lys Ile Glu Trp
            420                 425                 430

His Glu His His His His His
        435                 440

<210> SEQ ID NO 30
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: exemplary human HLA-G/ rat RT1A beta-2M MHC
      class I complex wherein the positions specific for human HLA-G are
      grafted onto the rat RT1A framework

<400> SEQUENCE: 30

Ala Gln Phe Ser Ala Ser Ala Ser Arg Gly Cys Gly Gly Ser Gly Gly
1               5                   10                  15

Gly Gly Ser Gly Gly Gly Gly Ser Ile Gln Lys Thr Pro Gln Ile Gln
            20                  25                  30

Val Tyr Ser Arg His Pro Pro Glu Asn Gly Lys Pro Asn Phe Leu Asn
        35                  40                  45

Cys Tyr Val Ser Gln Phe His Pro Pro Gln Ile Glu Ile Glu Leu Leu
    50                  55                  60

Lys Asn Gly Lys Lys Ile Pro Asn Ile Glu Met Ser Asp Leu Ser Phe
65                  70                  75                  80

Ser Lys Asp Trp Ser Phe Tyr Ile Leu Ala His Thr Glu Phe Thr Pro
                85                  90                  95

Thr Glu Thr Asp Val Tyr Ala Cys Arg Val Lys His Val Thr Leu Lys
                100                 105                 110

Glu Pro Lys Thr Val Thr Trp Asp Arg Asp Met Gly Gly Gly Gly Ser
            115                 120                 125

Gly Gly Gly Gly Ser Gly Gly Gly Ser Gly Gly Gly Gly Ser Gly
        130                 135                 140

Ser His Ser Leu Arg Tyr Phe Tyr Thr Ala Val Ser Arg Pro Gly Leu
145                 150                 155                 160

Gly Glu Pro Arg Phe Ile Ala Val Gly Tyr Val Asp Asp Thr Glu Phe
                165                 170                 175
```

Val Arg Phe Asp Ser Asp Ser Ala Ser Pro Arg Met Glu Pro Arg Ala
            180                 185                 190

Pro Trp Val Glu Gln Glu Gly Pro Glu Tyr Trp Gln Gln Thr Arg
        195                 200                 205

Ile Ala Lys Glu Trp Glu Gln Ile Tyr Arg Met Asp Leu Gln Thr Leu
    210                 215                 220

Arg Gly Cys Tyr Asn Gln Ser Glu Ala Ser Ser His Thr Ile Gln Glu
225                 230                 235                 240

Met Tyr Gly Cys Asp Leu Gly Ser Asp Gly Arg Leu Leu Arg Gly Tyr
                245                 250                 255

Arg Gln Asp Ala Tyr Asp Gly Arg Asp Tyr Ile Ala Leu Asn Glu Asp
                260                 265                 270

Leu Arg Ser Trp Thr Ala Ala Asp Phe Ala Ala Gln Ile Thr Lys Arg
                275                 280                 285

Lys Trp Glu Ala Ala Asn Tyr Ala Glu Arg Leu Arg Ala Tyr Leu Glu
        290                 295                 300

Gly Thr Cys Val Glu Trp Leu His Arg Tyr Leu Glu Asn Gly Lys Glu
305                 310                 315                 320

Met Leu Gln Arg Ala Asp Pro Pro Glu Ala His Val Thr His His Pro
                325                 330                 335

Val Phe Asp Tyr Glu Ala Thr Leu Arg Cys Trp Ala Leu Gly Phe Tyr
                340                 345                 350

Pro Ala Glu Ile Ile Leu Thr Trp Gln Leu Asn Gly Glu Asp Leu Thr
            355                 360                 365

Gln Asp Val Glu Leu Val Glu Thr Arg Pro Ala Gly Asp Gly Thr Phe
    370                 375                 380

Gln Lys Trp Ala Ser Val Val Val Pro Ser Gly Lys Glu Gln Asn Tyr
385                 390                 395                 400

Thr Cys Arg Val Gln His Glu Gly Leu Pro Lys Pro Leu Met Leu Arg
                405                 410                 415

Trp Gly Ser Gly Leu Asn Asp Ile Phe Glu Ala Gln Lys Ile Glu Trp
                420                 425                 430

His Glu His His His His His His
        435                 440

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: linker and his-Tag

<400> SEQUENCE: 31

Gly Gly Gly Gly Ser Gly Gly Gly Ser Gly Ser Gly Leu Asn Asp
1               5                   10                  15

Ile Phe Glu Ala Gln Lys Ile Glu Trp His Glu His His His His
            20                  25                  30

His

<210> SEQ ID NO 32
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 32

Val Leu Asp Phe Ala Pro Pro Gly Ala
1               5

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 105
<212> TYPE: PRT
<213> ORGANISM: Homo sapiens

<400> SEQUENCE: 34

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 35
<211> LENGTH: 328
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 36
<211> LENGTH: 328
<212> TYPE: PRT
<213> ORGANISM: Homo sapiens

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Ala Ala Gly Gly Pro Ser Val Phe Leu Phe Pro Pro
                115                 120                 125
Lys Pro Lys Asp Thr Leu Met Ile Ser Arg Thr Pro Glu Val Thr Cys
                130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Gly Ala Pro Ile Glu Lys Thr Ile Ser Lys Ala Lys Gly
                210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 37
<211> LENGTH: 325
<212> TYPE: PRT
<213> ORGANISM: Homo sapiens

<400> SEQUENCE: 37

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
                100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
                325

<210> SEQ ID NO 38
<211> LENGTH: 122
<212> TYPE: PRT
<213> ORGANISM: Rattus sp.

<400> SEQUENCE: 38

Glu Val Gln Leu Val Glu Thr Gly Gly Gly Leu Val Gln Ser Gly Arg
1               5                   10                  15

Ser Leu Lys Leu Ser Cys Val Ala Ser Gly Phe Thr Phe Asn Asp Tyr
            20                  25                  30

Trp Met Thr Trp Thr Arg Gln Ala Pro Gly Lys Gly Leu Glu Trp Val
        35                  40                  45

Ala Ser Ile Thr Asn Ser Gly Gly Arg Thr Tyr Tyr Leu Asp Ser Val
50                  55                  60

Arg Gly Arg Phe Thr Ile Ser Arg Asp Asp Ala Gln Asn Thr Leu Tyr
65                  70                  75                  80

Leu Gln Met Asn Ser Leu Arg Ser Glu Asp Thr Ala Thr Tyr Tyr Cys
                85                  90                  95

Thr Lys Glu Arg Ile Tyr Leu Thr Ala Tyr Trp Phe Phe Asp Phe Trp
            100                 105                 110

Gly Pro Gly Thr Met Val Thr Val Ser Ser
        115                 120

<210> SEQ ID NO 39
<211> LENGTH: 106
<212> TYPE: PRT
<213> ORGANISM: Rattus sp.
```

```
<400> SEQUENCE: 39

Asp Thr Ile Leu Thr Gln Ser Pro Ala Leu Ala Val Ser Pro Gly Glu
1               5                   10                  15

Arg Val Thr Ile Ser Cys Arg Ala Ser Glu Ser Val Ser Thr Leu Ile
            20                  25                  30

His Trp Tyr Gln Gln Lys Pro Gly Gln Arg Pro Lys Leu Leu Ile Tyr
        35                  40                  45

Leu Ala Ser His Leu Glu Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Thr Ala Thr Tyr Tyr Cys Gln Gln Ser Trp Asn Glu Pro Arg Thr
                85                  90                  95

Phe Gly Gly Gly Thr Lys Leu Glu Leu Lys
            100                 105
```